United States Patent
Van Hoeven et al.

(10) Patent No.: US 12,427,116 B2
(45) Date of Patent: *Sep. 30, 2025

(54) NANOALUM PARTICLES CONTAINING A PEGYLATED LIPID SIZING AGENT

(71) Applicant: ACCESS TO ADVANCED HEALTH INSTITUTE, Seattle, WA (US)

(72) Inventors: Neal Van Hoeven, Seattle, WA (US); Traci Mikasa, Renton, WA (US); Christopher B. Fox, Sumner, WA (US); Anwar Ahniyaz, Stockholm (SE); Mark T. Orr, Seattle, WA (US); Amit Khandhar, Issaquah, WA (US)

(73) Assignee: ACCESS TO ADVANCED HEALTH INSTITUTE, Seattle, WA (US)

( * ) Notice: Subject to any disclaimer, the term of this patent is extended or adjusted under 35 U.S.C. 154(b) by 794 days.

This patent is subject to a terminal disclaimer.

(21) Appl. No.: 17/411,591

(22) Filed: Aug. 25, 2021

(65) Prior Publication Data
US 2022/0016042 A1    Jan. 20, 2022

Related U.S. Application Data

(63) Continuation of application No. 16/098,617, filed as application No. PCT/US2017/035314 on May 31, 2017, now Pat. No. 11,173,126.
(Continued)

(51) Int. Cl.
A61K 9/51     (2006.01)
A61K 9/1271   (2025.01)
(Continued)

(52) U.S. Cl.
CPC .......... *A61K 9/5115* (2013.01); *A61K 9/1271* (2013.01); *A61K 9/5138* (2013.01);
(Continued)

(58) Field of Classification Search
CPC ........................... A61K 9/1271; A61K 9/5115
See application file for complete search history.

(56) References Cited

U.S. PATENT DOCUMENTS

2014/0234422 A1    8/2014    Pasteur

FOREIGN PATENT DOCUMENTS

| CN | 103826658 | * | 5/2014 |
| CN | 103826658 A | | 5/2014 |

(Continued)

OTHER PUBLICATIONS

Dynamic Light Scattering: A practical guide and application in biomedical sciences; Biophys Rev, 6, 8(4): 409-427. (Year: 2016).*
(Continued)

*Primary Examiner* — Carlos A Azpuru
(74) *Attorney, Agent, or Firm* — Benjamin Keim; Newport IP, LLC

(57) ABSTRACT

Provided herein are nanoalum particles comprising an aluminum salt and a sizing agent, wherein the size of the particle ranges from about 1 nm to 450 nm. Such a nanoalum particles are stable and are amenable to a terminal sterilization step prior to vialing. Compositions comprising the nanoalum particles, and the making and using of the nanoalum particles are also provided.

23 Claims, 22 Drawing Sheets

Related U.S. Application Data

(60) Provisional application No. 62/344,347, filed on Jun. 1, 2016.

(51) Int. Cl.
  *A61K 39/39* (2006.01)
  *A61K 39/00* (2006.01)
  *B82Y 5/00* (2011.01)

(52) U.S. Cl.
  CPC .......... *A61K 9/5161* (2013.01); *A61K 9/5192* (2013.01); *A61K 39/39* (2013.01); *A61K 2039/55505* (2013.01); *B82Y 5/00* (2013.01)

(56) References Cited

FOREIGN PATENT DOCUMENTS

| | | |
|---|---|---|
| CN | 104055736 A | 9/2014 |
| JP | 2014520836 A | 8/2014 |
| WO | 2007/098186 A2 * | 8/2007 |

OTHER PUBLICATIONS

Communication pursuant to Article 94(3) EPC for related matter EPO Application No. 17729681.1, mailed Mar. 3, 2023, 5 pages.
Office Action for related Israel Patent Application No. 298227 mailed May 29, 2023, 4 pages.
Office Action for related Japan Patent Application No. 2022-100579, mailed Jun. 7, 2023, 13 pages (with translation).
Office Action for related Republic of Korea Patent Application No. 10-2022-7041252, mailed Aug. 28, 2023, 18 pages (with translation).
MX/a/2021/010105—Office Action, mailed Mar. 7, 2022, 8 pages. (English Translation).
JP 2018-558419—Decision of Refusal, mailed Feb. 18, 2022, 8 pages. (English Translation).
AU 2017273650—Examination Report, mailed Apr. 27, 2022, 4 pages.
AU 2017273650—Notice of Acceptance, mailed Aug. 5, 2022, 3 pages.
JP 2018-558419—Decision to Grant, mailed Aug. 29, 2022, 5 pages, with English translation.
KR 10-2018-7034581—Notice of Final Rejection, mailed Apr. 26, 2022, 11 pages, with English translation.
KR 10-2018-7034581—Notice of Allowance, mailed Aug. 26, 2022, 4 pages, with English translation.
MX MX/a/2021/010105—Granting Notification, mailed Apr. 22, 2022, 6 pages.
CN 201780033663.5, Second Office Action, mailed Aug. 27, 2021, 18 pages. (English Translation).
BR 112018074352, Office Action, mailed Sep. 22, 2021, pp. 4.
IL 262877—First Office Action, mailed Oct. 7, 2021, 8 pages, with machine translation.
KR 10-2018-7034581—Office Action, mailed Oct. 5, 2021, 12 pages, with machine translation.
Australian Office Action for related matter application No. 2022263559 dated Mar. 5, 2024, 6 pages.
Li, X., et al., 'Aluminum hydroxide nanoparticles show a stronger vaccine adjuvant activity than traditional aluminum hydroxide microparticles', J Control Release, 2014, vol. 10, No. 173, pp. 148-157.
Sun B. et al., 'Engineering an effective immune adjuvant by designed control of shape and crystallinity of aluminum oxyhydroxide nanoparticles', ACS Nano., 2013, vol. 7, No. 12, pp. 10834-10849.
Japan Decision to Grant a Patent for related matter application No. 2022-100579 dated Feb. 2, 2024, 2 pages.
Office Action for related matter Japanese patent application No. 2024-020137 issued Mar. 25, 2025, 11 page (with translation).

\* cited by examiner

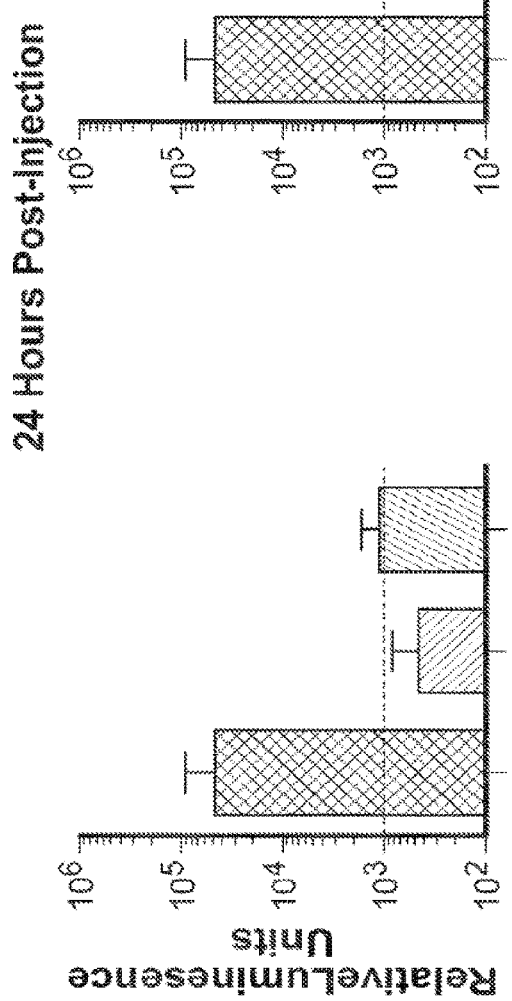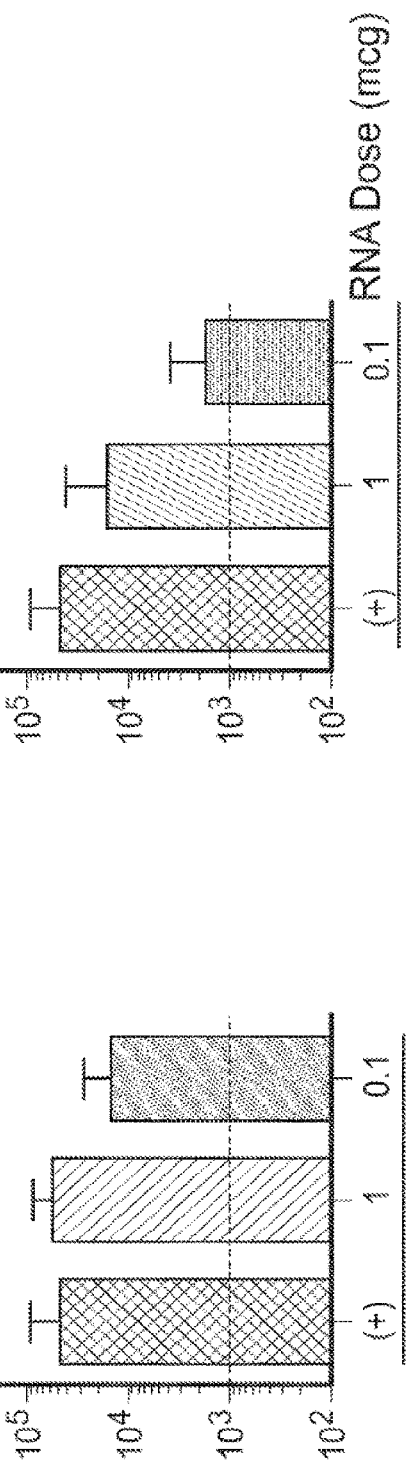
FIG. 7A  FIG. 7B  FIG. 7C  FIG. 7D

| Group | RNA Dose | Formulation |
|---|---|---|
| 1 | 10µg | Unformulated |
| 2 | 0.1µg | Unformulated |
| 3 | 0.1µg | Control Cationic Emulsion |
| 4 | 0.1µg | PAA Nanoalum |

NANOALUM PARTICLES CONTAINING A PEGYLATED LIPID SIZING AGENT

CROSS-REFERENCE TO RELATED APPLICATIONS

This application claims the benefit of U.S. Provisional Application No. 62/344,347, filed Jun. 1, 2016, which is hereby incorporated by reference in its entirety.

FIELD OF THE INVENTION

The present invention relates to the field of pharmaceutical and vaccine formulations. More specifically, embodiments described herein relate to nanoalum particles, compositions comprising the nanoalum particles, and methods of making and using the nanoalum particles.

BACKGROUND

Aluminum salts (collectively referred to as Alum) have been used in vaccines for over eight decades due to their good safety profile and their ability to induce an enhanced immune response to adsorbed vaccine antigens [1, 2]. As one of the few classes of adjuvants approved by the US FDA, aluminum salts have an established regulatory pathway as opposed to more novel adjuvant formulations [1]. When dispersed in an aqueous solution, aluminum salts form heterogeneous aggregate particulates of ~0.5-10 microns (μm) in size, which may make them difficult to characterize for quality control compared to formulations with monodisperse size populations such as oil-in-water emulsions. This complexity is compounded by the fact that there are multiple types of aluminum salts available with distinct properties, including aluminum phosphate, aluminum hydroxyphosphate sulfate, and aluminum oxyhydroxide.

Several studies have proposed that the average particle size of an adjuvant formulation is a critical factor that can affect the biological activity of the vaccine (1). Recently, novel synthetic approaches have been employed using aluminum salts to de novo manufacture new synthetic formulations containing alum nanoparticles. These synthetic nanoparticles have been described to generate a stronger immune response while decreasing inflammation at the injection site, when compared to microparticles [1, 4, 5]. Nevertheless, in each of these studies, a bottom-up synthetic approach was employed to manufacture the aluminum panicles, and no comparison was made to clinical aluminum salt adjuvants such as Alhydrogel®, making it difficult to interpret the value of the novel formulations versus the clinically approved material.

Additionally, from a regulatory perspective, clinical aluminum-based microparticles are not capable of being terminally sterilized by filtration through 0.45 or 0.20 micron filters, and are only sterilizable by radiation or autoclave; making their manufacture not amenable to a terminal sterilization step when combined with antigens or adjuvants. There exists a need to provide aluminum-based nanoparticles that display little to no aggregation, or reduced aggregation, and are capable of being terminally sterilized prior to being vialed.

BRIEF SUMMARY OF THE INVENTION

The present disclosure provides nanoalum particles, compositions comprising the nanoalum particles, and methods of making and using the nanoalum particles. The nanoalum particles are useful in the field of pharmaceuticals and/or vaccine formulations. Provided herein are compositions (including formulations) comprising a plurality of nanoalum particles comprising an aluminum salt and a sizing agent, wherein the size of the particles in the composition is less than 1 μm. The term nanoalum particle is used herein to denote that the particle comprises aluminum and has a size measured in nanometers, typically from 1 nm to about 450 nm. In some embodiments, the composition is for a terminal sterilization by filter for products according to FDA regulation (such as use of a ≤0.45 micron filter). In some embodiments, the size of the particles present in the composition ranges from about 1 nm to about 450 nm. In some embodiments, the average size of the particles in the composition ranges from about 1 nm to about 450 nm. In some embodiments, the average size of the particles in the composition ranges from about 1 nm to about 200 nm. Nanoalum compositions described here may be produced by processing or milling aluminum hydroxide in the presence of the sizing agent by standard techniques known in the art including, but not limited to, microfluidization, sonication, and high shear mixing. High shear mixing can be performed using a high shear mixer. Silverson is one company that produces high shear mixers that can be used in the present methods.

The nanoalum particles in the compositions are stable and display little to no aggregation, or reduced aggregation, and are amenable to a terminal sterilization step prior to vialing. The nanoalum particles provided herein are useful for the delivery of an agent, such as a polypeptide or a polynucleotide, to an individual. By way of example only, the nanoalum panicles provided herein are useful for the delivery of antigens and/or adjuvants to a host in order to generate an immune response.

The present disclosure provides for a nanoalum particle comprising: (a) an aluminum salt; and (b) a sizing agent; wherein the size of the particle ranges from about 1 nm to about 450 nm.

In certain embodiments, the average size of the panicles is the Z-average as determined by dynamic light scattering.

In certain embodiments, the aluminum salt is selected from the group consisting of aluminum hydroxide, aluminum hydroxide gel, $AlPO_4$, $AlO(OH)$, $Al(OH)(PO_4)$, and $KAl(SO_4)_2$.

In certain embodiments, the sizing agent is selected from sizing agents presented in Table 1. The sizing agent can be selected from the group consisting of PAA, PEG, and PEG linked to a lipid. The sizing agent can be selected from the group consisting of chitosan, dextran (e.g., dextran sulfate), or poly(allylamine). The sizing agent can be selected from the group consisting of PAA, PEG, PEG linked to a lipid, chitosan, dextran sulfate, or poly(allylamine).

In certain embodiments, the sizing agent is PEG linked to a phospholipid. In certain embodiments, the sizing agent is PEG and the average molecular weight of the PEG ranges from about 750 Daltons to about 5000 Daltons. In certain embodiments, the sizing agent is PEG linked to a lipid (optionally a phospholipid) and the average molecular weight of the PEG ranges from about 750 Daltons to about 5000 Daltons. In certain embodiments, the lipid is selected from the group consisting of DSPE, DPPE, and DMPE. In certain embodiments, the sizing agent is PAA and the average molecular weight of the PAA ranges from about 750 Daltons to about 7000 Daltons.

When the sizing agent is chitosan, it can be low molecular weight chitosan (e.g., a molecular weight of from about 15 kDa to about 190 kDa), medium molecular weight chitosan (e.g., a molecular weight of from about 190 kDa to about 700 kDa) or high molecular weight chitosan (e.g., a molecular weight of from about 700 kDa to about 1000 kDa). The degree of deactylation of chitosan (DDA) will vary depending on the method of purification and reaction conditions. The degree of deactylation of chitosan typically ranges from about 40% to about 90% with commercial chitosans typically having a DDA of about 70% to about 90%, however chitosans with DDAs greater than 90% or lower than 40% can be used in the present methods as can chitosans with DDAs from about 40% to about 90%, preferably from about 70% to about 90%. In some embodiments, at least one primary amine group on the C2 carbon of chitosan can be used as site for covalent conjugation. Accordingly, the term chitosan as used herein incudes chitosan conjugates, including, but not limited to, mannosylated chitosan or fluorescently labeled chitosan. Chitosan for use in the present methods is commercially available from many sources including SIGMA-ALDRICH™.

When the sizing agent is dextran, it can be any of the class 1, 2 or 3 dextrans having a molecular weight of equal to or greater than 1000 daltons. A particularly preferred dextran for use as a sizing agent is dextran sulfate. Dextran sulfate is typically sold as its sodium salt—accordingly, as used herein, the term dextran sulfate also includes salt forms thereof including its sodium salt forms. As with chitosan, when the sizing agent is dextran sulfate, it can be low molecular weight (e.g., 5000 daltons to 100 kDa), medium molecular weight (e.g., 100 kDa to 500 kDa) or high molecular weight dextran sulfate (e.g., 500 kDa to 1000 or even 2000 kDa). A preferred dextran sulfate has a molecular weight from about 20 kDa to about 80 kDa Poly(allylamine) is a water soluble cationic polymer with free primary amino groups that can be used as a sizing agent as described herein. Poly(allylamine) preferably has a molecular weight from about 5 kDa to about 100 kDa, most preferably about 5 kDa to about 50 kDa, most preferably from about 5 kDa to about 25 kDa. Either the free base form of poly(allylamine) can be used or any of its salt forms (e.g. hydrochloric acid salt). The skilled artisan would understand that poly(allylamine) polymers with molecular weights greater than 100 kDa can be used in the methods described herein, and, additionally, when a salt form of poly(allylamine) is used, its molecular weight will increase.

In certain embodiments, the nanoalum particle is in a liquid formulation which is filter-sterilized. In certain embodiments, the nanoalum particle is stable in a liquid formulation at about 0° C. to about 8° C. for at least about 1 month, at least about 6 months, or at least about 1 year. In certain embodiments, the nanoalum particle is stable in a liquid formulation at about 37° C. for at least about 1 month. In certain embodiments, the sizing agent is associated with the aluminum salt.

The present disclosure provides a method of making a nanoalum particle comprising subjecting an aluminum salt to a high energy source in the presence of a sizing agent, whereby a nanoalum particle is produced, and wherein the size of the nanoalum particle ranges from about 1 nm to about 450 nm.

As will be appreciated by skilled artisan, the nanoalum particles of the present invention can be made from larger particles of micrometer size. Accordingly, the present disclosure provides a method of making the described nanoalum particles from precursor aluminum salt particles that are 0.5 μm to 20 μm in size or 0.5 urn to 10 μm in size.

The present disclosure provides a method of making a nanoalum particle comprising (a) subjecting an aluminum salt to a high energy source to produce a nanoalum particle with a size ranging from about 1 nm to about 450 nm, and (b) mixing a sizing agent with the nanoalum particle within about 30 minutes after step (a).

In certain embodiments, the high energy source is generated from a microfluidizer, an extruder, a sonicator, high shear mixer (e.g., silverson mixer), or a homogenizer. Two or more high energy sources can be used. For example, the high energy source can be generated from a microfluidizer and a high shear mixer and the mixture comprising the aluminum salt and sizing agent can be passed through the microfluidizer for one or more passes (e.g., from one pass to about 30 or more passes). In certain embodiments, the high energy source is generated from a microfluidizer, and the mixture comprising the aluminum salt and sizing agent is passed through the microfluidizer from one pass to about 15 passes. In certain embodiments, the aluminum salt is selected from the group consisting of aluminum hydroxide, aluminum hydroxide gel, $AlPO_4$, $AlO(OH)$, $Al(OH)(PO_4)$, and $KAl(SO_4)_2$. In certain embodiments, the sizing agent is selected from the group consisting of PAA, PEG, and PEG linked to a lipid. Alternatively, the sizing agent can be selected from a sizing agent set forth in Table 1 or from chitosan, dextran, or poly(allylamine). In certain embodiments, the sizing agent is PEG and the average molecular weight of the PEG ranges from about 750 Daltons to about 5000 Daltons. In certain embodiments, the sizing agent is PEG linked to a lipid (optionally a phospholipid) and the average molecular weight of the PEG ranges from about 750 Daltons to about 5000 Daltons. In certain embodiments, the lipid is selected from the group consisting of DSPE, DPPE, and DMPE. In certain embodiments, the sizing agent is PAA and the average molecular weight of the PAA ranges from about 750 Daltons to about 7000 Daltons. In certain embodiments, the method further comprises filter-sterilizing the nanoalum particle. In certain embodiments, the ratio of aluminum salt to PEG is between about 2:1 to about 7.5:1. In embodiments wherein the sizing agent is chitosan or poly(allylamine), the aluminum salt will undergo surface modification via phosphate ligand exchange.

The present disclosure provides a nanoalum particle obtainable or produced by a method disclosed herein, wherein the size of the nanoalum particle ranges from about 1 nm to about 450 nm.

The present disclosure provides a composition comprising the nanoalum particle disclosed herein.

In certain embodiments, the composition further comprises a bioactive agent. In certain embodiments, the bioactive agent is associated with the nanoalum particle in the composition. In certain embodiments, more than about 75% of the bioactive agent is associated with the nanoalum particle in the composition as determined by gel electrophoresis. In certain embodiments, the bioactive agent is a polypeptide, a polynucleotide, an antigen, an adjuvant, a diagnostic agent, a therapeutic agent, or an organism. In certain embodiments, the bioactive agent is a polypeptide. In certain embodiments, the polypeptide is an antigen, a fusion protein, a full-length protein, a peptide, or a peptide mimetic. In certain embodiments, the antigen is a Rig I agonist. In certain embodiments, the bioactive agent is a polynucleotide. In certain embodiments, the polynucleotide is DNA. In certain embodiments, the DNA comprises a sequence encoding a polypeptide. In certain embodiments, the DNA is an oligonucleotide. In certain embodiments, the polynucleotide is RNA. In certain embodiments, the RNA is selected from the group consisting of replicon RNA, mRNA, (RNA, siRNA, shRNA, and microRNA. In certain embodiments, the RNA comprises a sequence encoding a polypeptide. In certain embodiments, the composition further comprises an adjuvant. In certain embodiments, the adjuvant is selected from the group consisting of a AS-2, monophosphoryl lipid A, 3-de-O-acylated monophosphoryl lipid A, UFA, QS21, CWS, TOM, AGPs, CpG-containing oligonucleotides, Toll-like receptor (TLR) agonists, Leif, saponins, saponin mimetics, biological and synthetic lipid A, imiquimod, gardiquimod, resiquimod, polyI:C, flagellin, GLA, SLA, STING, and combinations thereof.

In certain embodiments, the composition is a liquid formulation. In certain embodiments, the composition is capable of being filtered through a 0.20 micron-sized filter or a 0.45 micron-sized filter. In certain embodiments, the composition is capable of being terminally sterilized prior to vialing. In certain embodiments, the composition is stable at about 0° C. to about 8° C. for at least about 1 month, at least about 6 months, or at least about 1 year. In certain embodiments, the composition is stable at about 37° C. for at least about 1 month. In certain embodiments, the composition further comprises a liposome. In certain embodiments, the average size of the particles in the composition is from about 1 nm to about 450 nm.

The present disclosure provides a kit comprising a first vial containing the composition disclosed herein. In certain embodiments, the kit further comprises a second vial containing another agent.

The present disclosure provides a method of stimulating an immune response in a subject comprising administering the composition disclosed herein to a subject, whereby stimulating an immune response in the subject.

In certain embodiments, the immune response is a non-specific immune response. In certain embodiments, the immune response is an antigen-specific immune response. In certain embodiments, the immune response involves the activation of B-cells, activation of T cells, production of antibodies, or release of cytokines. In certain embodiments, the composition is used for monotherapy. In certain embodiments, the composition is used for the treatment of allergy, addiction, cancer, or autoimmunity. In certain embodiments, the route of administration of the composition is oral, intravenous, intradermal, transdermal, nasal, subcutaneous, or anal. In certain embodiments, the subject is a human. In certain embodiments, the subject is a non-human mammal. In certain embodiments, the non-human mammal is a dog, cat, cow, or horse.

The present disclosure provides a method of delivering a bioactive agent to a cell in a subject comprising administering to the subject a composition comprising (a) a nanoalum particle comprising an aluminum salt and a sizing agent, wherein the size of the particle ranges from about 1 nm to about 450 nm and (b) a bioactive agent, thereby delivering the bioactive agent to the cell in the subject.

In certain embodiments, the bioactive agent is delivered into the cell. In certain embodiments, the bioactive agent is an RNA comprising a sequence encoding a polypeptide and the polypeptide is expressed by the cell. In certain embodiments, the composition generates an immune response in the subject.

The present disclosure provides a method of making a composition comprising mixing the nanoalum particle disclosed herein with a bioactive agent.

The present disclosure provides a method of making a composition comprising the steps: (a) subjecting an aluminum salt to a high energy source in the presence of a sizing agent, whereby a nanoalum particle is produced, and wherein the size of the nanoalum particle ranges from about 1 nm to about 450 nm; and (b) mixing the nanoalum particle produced in step (a) with a bioactive agent.

The present disclosure provides a method of making a composition comprising the steps: (a) subjecting an aluminum salt to a high energy source to produce a nanoalum particle with a size ranging from about 1 nm to about 450 nm; (b) mixing a sizing agent with the nanoalum particle within about 30 minutes after step (a), and (c) mixing the nanoalum particle with a bioactive agent during or after step (b).

These and other aspects of the present invention will become evident upon reference to the following detailed description and attached drawings. In addition, various references are set forth herein which describe in more detail certain aspects of this invention, and are therefore incorporated by reference in their entireties.

BRIEF DESCRIPTION OF THE DRAWINGS

FIG. 1A demonstrates that nanoalum formulations processed or milled in the presence of PA A2000 as the sizing agent subjected to three or six passages at 30K PSI have average particle sizes of around 100 nm with polydispersity of around 0.25-0.3. Increasing the milling to 10-15 passages resulted in nanoalum formulations of approximately 78-87 nm with no increase in polydispersity FIG. 1B-C depicts particle diameter over time of nanoalum formulations with either PEG phospholipid (PEG 5000-DSPE at 2:1 ratio to alum) or PAA as the sizing agent. The formulations having initial particle sizes of approximately 78 nm were stored at 4° C. for up to one year and tested at indicated time points for particle size and polydispersity. Samples were taken in triplicate. FIG. 1D-F: Thermostability of Nanoalum Formulations. Nanoalum formulations of less than 100 nm particle size formulated with pegylated lipids of differing PEG lengths (5000, 2000 and 750) and or differing acyl chain lengths (18, 16 or 14 carbons) were evaluated for thermostability at 25° C., 37° C. or 60° C. for 0, 2 or 4 weeks. QG194 is PEG5000-DSPE; QG195 is PEG2000-DMPE; QG196 is PEG2000-DPPE; QG197 is PEG750-DSPE; QG198 is PEG2000-DSPE.

FIG. 3A shows the frequency of $CD4^+$T cells making each response specific to ID97. Serum was collected from immunized animals one week after immunization and assessed for ID97 binding antibody titers by ELISA for the IgG isotype (3B) and IgG1 (3C) and IgG2 subclasses (3D). The data demonstrates that nanoalum PAA augments Th1 responses. The legend for FIG. 3B is the same as for 3A and the legend for 3C is the same as that for 3D.

FIG. 7A-D: Expression of RNA replicon vectors formulated with nanoalum RNA is not due to the sizing agent in the nanoalum formulation. In FIG. 7A-D, the data grouped according to formulation and by dose of the replicon vector delivered (meg unformulated depicted as a +) 1 μg (meg), and 0.1 μg (meg) respectively) at 24 hours demonstrate that PAA alone (top right panel) does not deliver and/or induce an expressible level of an RNA replicon at doses of 0.1 or 1.0 μg whereas the same doses of the RNA replicon formulated or admixed either with the control cationic emulsion or PAA nanoalum demonstrates detectable luciferase expression.

FIG. 8A depicts the relative luminesence observed in animals injected with an mRNA encoding luciferase and imaged for the expression of the luciferase gene. The unformulated mRNA demonstrates detectable expression at both 1 μg and 1 μg, but not at 0.1 μg when accessed at 24 hours post injection (left group). However, both the control cationic formulation and the PAA nanoalum formulation (middle and far right groups) not only express equivalent levels of the mRNA encoded gene at all doses (10 μg, 1 μg, and 0.1 μg) when compared to each other, but they also demonstrate increased levels of expression (>30 fold) at the 1 μg dose compared to the unformulated mRNA and have detectable levels of expression at the 0.1 μg dose demonstrating dose sparing properties of the nanoalum formulation. FIG. 8B depicts the relative immunofluorescence of animals imaged for the expression of the mRNA 5 at days post injection. The unformulated mRNA demonstrates detectable expression of the mRNA encoded gene at 10 μg but not at the lower doses (1 μg and 0.1 μg) and the mRNA formulated in the control cationic formulation demonstrates no detectable expression at any of the doses delivered (10 μg, 1 μg, 0.1 μg) when assessed 5 days post injection (left group and middle). PAA Nanoalum formulation (far right groups) express >10 fold higher levels of the luciferase encoded by the mRNA at the 10 μg dose and shows detectable expression at the 1 μg dose that is roughly equivalent to the levels observed with 10 μg of unformulated mRNA, demonstrating dose sparing properties of the nanoalum formulation even at 5 days post delivery of the mRNA. FIG. 8C depicts the relative in vivo expression of the mRNA encoded luciferase gene at 6 hours, 24 hours and 5 days after admixing as unformulated, control cationic emulsions formulations or PAA nanoalums and injected in vivo. The data demonstrate that the animals that were immunized with mRNA formulated with nanoalum formulations have increased and relatively steady levels of expression of the mRNA encoded luciferase gene over five days (□) compared to either unformulated mRNA (•) or the control cationic emulsion formulated mRNA (▲) which had a rapid decline in expression.

FIG. 9C-E are scatter plots of the data directly comparing the control cationic formulation, PAA nanoalum, and unformulated replicon respectively. RNA when administered immediately after admix with the replicon RNA (T=0, left panel 9C), administered 4 hours after admixing and storage at 4° C. (T=1 h, middle panel 9D) or admixed and stored for 24 hours (T=24 h, right panel 9E) at 4° C. Gene expression is measured at day 5 post administration to the animals by relative luminesence units. Luciferase expression levels demonstrate that the nanoalum formulated RNA is stable when admixed as a single vial formulation at 4° C. for up to 24 hours compared to unformulated RNA.

FIG. 10A-D demonstrate that immunization with 100 fold lower doses of EMCH RNA formulated with control cationic emulsion or PAA nanoalum generates approximately equivalent percentages of CD4+ CD44 high CD154. IFN γ, IL-2 or TNFα cytokine producing T cells as 10 μg of unformulated RNA compared to little or no cytokine induction following administration of 0.1 μg of unformulated RNA replicon. FIG. 10E: The hallmark of protective Leishmaniasis immune response includes the presence of polyfunctional antigen specific T cells that secrete multiple cytokines. CD4+ CD44 high T cells were further analyzed for polyfunctional T cells responses. The data demonstrate that mice immunized with 100 ng of EMCH RNA replicon formulated with PAA nanoalum (hatched bar) or the formulated with the control cationic emulsion (diagonal slashed bar) had equivalent numbers of triple positive CD44 high IFN-γ+IL-2+TNFα CD4+ T cells to the 10 μg unformulated RNA (solid black bar) immunized animals. Double positive cells expressing IFN-γ and IL-2 or IL-2 and TNFα were also present. The data demonstrate PAA nanoalum formulations are capable of delivering RNA that is expressed at a level sufficient to generate relevant antigen specific immune responses.

FIG. 11A demonstrates that nanoalum formulations elicit antigen specific IgG1 antibody titers indicative of a Th2 bias. FIG. 11B demonstrates that nanoalum formulations plus the TLR4 agonist, SLA, elicit antigen specific IgG2c antibody titers indicative of a Th1 bias FIG. 12A-C demonstrates that mice immunized with PEG nanoalum formulations comprising either PEGylated phospholipid sizing agents with differing PEG lengths or the same PEG length linked to phospholipids of differing acyl chain lengths and admixed with TB fusion peptide ID93 plus the TLR4 agonist SLA elicit antigen specific immune responses.

FIG. 13A demonstrates the effect of the number of microfluidization passes at 30,000 psi on hydrodynamic size of nanoalum synthesized using AdjuPhos® precursor and 120 kDa chitosan with 75-85% DD. 13B demonstrates the hydrodynamic diameter and PDI of nanoalum manufactured using AdjuPhos® adjuvant as precursor and varying amounts of 120 kDa chitosan with 75-85% DD. Samples were microfluidized at 30,000 psi for 22 discrete passes.

FIG. 14-B.

FIG. 15A provides the zeta potential of native Alhydrogel® adjuvant before and after treatment with PBS buffer containing 67 mM phosphate. FIG. 15B demonstrates the particle diameter (Z-average) and size distribution of Alhydrogel®-derived nanoalum (0.2% w/v Al or 2 mgAl/ml) stabilized with various amounts of chitosan. Size data were collected immediately after microfluidization and before sterile filtration.

DETAILED DESCRIPTION

Figure 1A:
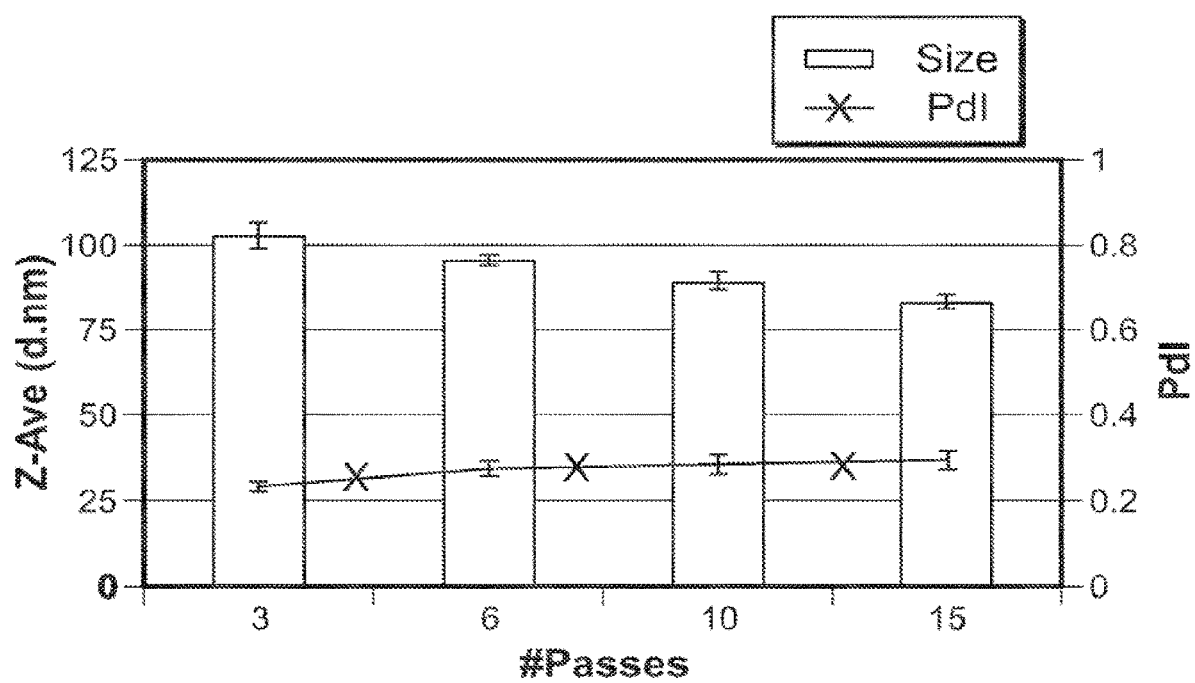
FIGS. 1A-F: Nanoalum Formulations with PAA and PEG Sizing Agents and Stability Analysis of Nanoalum Formulations.

The present disclosure described herein provides nanoalum particles, compositions comprising the nanoalum particles, and methods of making and using the nanoalum particles.

I. Definitions

The following terms have the following meanings unless otherwise indicated. Any undefined terms have their art recognized meanings.

In the present description, the terms "about" and "consisting essentially of" mean±20% of the indicated range, value, or structure, unless otherwise indicated. In some embodiments, the terms "about" and "consisting essentially of" mean±15%; ±10%; or ±5% of the indicated range, value, or structure, unless otherwise indicated.

The use of the alternative (e.g., "or") should be understood to mean either one, both, or any combination thereof of the alternatives.

As used herein, the terms "include," "have" and "comprise" are used synonymously, which terms and variants thereof are intended to be construed as non-limiting.

As used herein and in the appended claims, the singular forms "a," "an," and "the" include plural reference unless the context clearly indicates otherwise.

The term "bioactive agent" as used herein refers to any material to be delivered by the nanoalum formulations of the present disclosure and include without limitation macromolecules, peptides, proteins, peptidomimetics, nucleic acids, oligonucleotides, deoxyribonucleotides, ribonucleotides, mRNA, RNAi, RigI, replicon RNA, adjuvants including TLR agonists (for example TLR2, TLR3, TLR4, TLR 7, TLR8, and TLR9 agonists), saponins, whole viral particles, viral fragments, cellular fragments. Also included within the term bioactive agent are, for example, aptamers, carbohydrates, conjugated carbohydrates and virus-like particles.

The term "macromolecule" as used herein refers to large molecules exemplified by, but not limited to, peptides, proteins, oligonucleotides and polynucleotides of biologic or synthetic origin. Also included within the term macromolecule are, for example, carbohydrates.

The terms "polypeptide", "peptide", and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the an which includes peptidomimetic compounds which are derived from peptides and proteins by structural modification using unnatural amino acids.

The term "isolated" means the molecule has been removed from its natural environment.

"Purified" means that the molecule has been increased in purity, such that it exists in a form that is more pure than it exists in its natural environment and/or when initially synthesized and/or amplified under laboratory conditions. Purity is a relative term and does not necessarily mean absolute purity. In some embodiments, purified can mean 99%, 98%, 97%, 96%, 95%, 90%, 85%, or 80% more pure than it exists in its natural environment and/or when initially synthesized and/or amplified under laboratory conditions.

A "polynucleotide" or "nucleic acid," as used interchangeably herein, refers to polymers of nucleotides of any length, include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. A polynucleotide may comprise modified nucleotides, such as methylated nucleotides and their analogs. If present, modification to the nucleotide structure may be imparted before or after assembly of the polymer. The polynucleotides of the present disclosure include ribonucleotides (for example RNA, RNAi, tRNA, and mRNA as terms well known in the art) and deoxyribonucleotides (DNA) know in the art and may be single or double stranded molecules.

"Oligonucleotide," as used herein, generally refers to short, generally single stranded, generally synthetic polynucleotides that are generally, but not necessarily, less than about 200 nucleotides in length. The terms "oligonucleotide" and "polynucleotide" are not mutually exclusive. The description above for polynucleotides is equally and fully applicable to oligonucleotides. Examples include Rig I agonists.

A "replicon" as used herein includes any genetic element, for example, a plasmid, cosmid, bacmid, phage or virus that is capable of replication largely under its own control. A replicon may be either RNA or DNA and may be single or double stranded.

An "individual" or a "subject" is any mammal. Mammals include, but are not limited to humans, primates, farm animals, sport animals, pets (such as cats, dogs, horses), and rodents.

"Alkyl" is a straight or branched saturated hydrocarbon. For example, an alkyl group can have 1 to 30 carbon atoms (i.e., ($C_1$-$C_{30}$)alkyl) or 1 to 20 carbon atoms (i.e., ($C_1$-$C_{20}$)alkyl) or 1 to 10 carbon atoms (i.e., ($C_1$-$C_{10}$)alkyl) or 1 to 8 carbon atoms (i.e., ($C_1$-$C_8$)alkyl) or 1 to 6 carbon atoms (i.e., ($C_1$-$C_6$)alkyl) or 1 to 4 carbon atoms (i.e., ($C_1$-$C_4$)alkyl). This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), neopentyl (($CH_3$)$_3$CCH$_2$—), and n-hexyl ($CH_3(CH_2)_5$—).

"Halo" or "halogen" refers to fluoro, chloro, bromo, and iodo.

"Hydroxy" or "hydroxyl" refers to the group —OH.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like.

"Carboxyl ester" or "carboxy ester" refers to the groups —C(O)O-alkyl and —C(O)O-substituted alkyl, wherein alkyl and substituted alkyl are as defined herein.

II. General Techniques

The practice of the present disclosure will employ, unless otherwise indicated, conventional techniques of molecular biology, recombinant DNA, biochemistry and chemistry, which are within the skill of the art. Such techniques are explained fully in the literature. See, e.g., Molecular Cloning A Laboratory Manual, 2nd Ed., Sambrook et al., ed., Cold Spring Harbor Laboratory Press: (1989); DNA Cloning, Volumes I and II (D. N. Glover ed., 1985); Oligonucleotide Synthesis (M. J. Gait ed., 1984); Mullis et al., U.S. Pat. No. 4,683,195; Nucleic Acid Hybridization (B. D. Hames & S. J. Higgins eds. 1984); B. Perbal, A Practical Guide To Molecular Cloning (1984); the treatise, Methods In Enzymology (Academic Press, Inc., N.Y.); and in Ausubel et al., Current Protocols in Molecular Biology, John Wiley and Sons, Baltimore, Maryland (1989).

III. Nanoalum Particles

The nanoalum particles provided herein comprise an aluminum salt (interchangeably referred to as an alum) and a sizing agent, wherein the size of the particle ranges from about 1 nm to 450 nm. Discussion of the aluminum salts and sizing agents are provided below.

A. Aluminum Salts

The compositions described herein can comprise an aluminum salt, which can be referred to herein as alum. Suitable aluminum salts include aluminum hydroxide, aluminum trihydrate, aluminum oxyhydroxide, aluminum phosphate, aluminum hydroxyphosphate, aluminum hydroxyphosphate sulfate, and potassium aluminum sulfate. Aluminum salts can also be referred to by the formulae: $Al(OH)_3$, $AlH_3O_3$, $AlH_6O_3$, $AlO(OH)$, $Al(OH)(PO_4)$, and $KAl(SO_4)_2$. The skilled artisan will appreciate that aluminum hydroxyphosphate is nonstoichiometric and although it is represented herein as $Al(OH)(PO_4)$, the ratio of surface hydroxyls to phosphates vary depending on the manufacturing conditions and as such is more accurately represented by the formula: $Al(OH)_x(PO_4)_y$.

Aluminum salts used as co-adjuvants are advantageous because they have a good safety record, augment antibody responses, stabilize antigens, and are relatively simple for large-scale production. (Edelman 2002 Mol. Biotechnol. 21:129-148; Edelman, R. 1980 Rev. Infect. Dis. 2:370-383.)

In certain embodiments, the aluminum salt is Alhydrogel®, an aluminum hydroxide or aluminum oxyhydroxide. Alhydrogel® has an overall positive charge and can readily adsorb negatively charged moieties. Alhydrogel® can also be referred to as Amphojel; Aluminum hydroxide gel; Hydrated alumina; Aluminum trihydroxide; or Alugelibye.

In certain embodiments, the aluminum salt is AdjuPhos®, an aluminum phosphate. AdjuPhos® has an overall negative charge and can readily adsorb positively charged moieties.

The skilled artisan will appreciate that in embodiments wherein the aluminum salt and sizing agent to be used have the same surface charge, it is desirable to subject the aluminum salt to surface modification such that its charge can be reversed thereby allowing for attraction between the sizing agent and the aluminum salt. As an example, when the aluminum salt has a cationic surface charge (e.g., ALO(OH)) and the sizing agent has a cationic surface charge (e.g., chitosan, poly(allylamine)), ligand exchange (e.g., phosphate ligand exchange) acts to change the surface charge of the aluminum salt to anionic thereby allowing for interaction between the sizing agent and the aluminum salt.

B. Sizing Agents

In some embodiments, the size of the nanoalum particle is maintained because the sizing agent reduces, blocks, or retards the aggregation of the processed or milled aluminum salt, when compared to a nanoalum comprising an aluminum salt in the absence of a sizing agent.

In some embodiments the sizing agent is added during the processing aluminum salt by high energy input such as sonication or microfluidization to achieve the desired nanoalum particle size. In some embodiments the sizing agent is added after processing aluminum salt by high energy input such as sonication or microfluidization to achieve the desired nanoalum particle size. In some embodiments when the sizing agent is added after processing aluminum salt to achieve the desired nanoalum particle size by high energy input such as sonication or microfluidization the sizing agent is added immediately after processing or about 0.5 minutes, 0.5-1.0 minute, 1.0-1.5 minutes, 1.5-2.0 minutes, 2.0-2.5 minutes, 2.5-3.0 minutes, 3.0-3.5 minutes, 3.5-4.0 minutes, 4.0-4.5 minutes, 4.5-5.0 minutes, 5.05-5.5 minutes, 5.5-6.0 minutes, 6.0-6.5 minutes, 6.5-7.0 minutes, 7.0-7.5 minutes, 7.5-8.0 minutes, 8.0-8.5 minutes, 8.5-9.0 minutes, about 10 minutes, about 12 minutes, about 14 minutes, about 16 minutes, about 18 minutes, about 20 minutes, about 22 minutes, about 24 minutes, about 26 minutes, about 28 minutes, about 30 minutes after processing aluminum salt to achieve the desired nanoalum particle size.

In some embodiments, the sizing agent is one that changes the surface properties of the aluminum salt. In some embodiments, the sizing agent is one that stabilizes the size of the aluminum salt.

In some embodiments, the sizing agent is one that stabilizes or protects a bioactive agent. Examples of bioactive agents include, but are not limited to an antigen, adjuvant, TLR agonist, peptide mimetic, peptide, polypeptide, protein, nucleotide, polynucleotide, RNA, DNA, whole viral genome, and whole virus. The bioactive agent can be delivered by the nanoalum formulations of the present disclosure. In some embodiments, the sizing agent protects or shields the bioactive agent from oxidation. In some embodiments, the sizing agent protects or shields the bioactive agent from heat stress, which can include factors of heat temperature and time. In some embodiments the sizing agent protects or shields the bioactive agent from cold stress, which can include factors of cold temperature and time. In some embodiments, the sizing agent protects or shields the bioactive agent from degradation. In some embodiments, the sizing agent is one that shields or protects the bioactive agent to be delivered by the nanoalum formulations of the present disclosure from degradation or inactivation when exposed to serum or blood components. In some embodiments the sizing agent protects or shields the bioactive agent such that the agent may be formulated with the nanoparticles as a stable single vial formulation.

In some embodiments, the presence of the sizing agent reduces, blocks, or retards the aggregation or re-aggregation of the aluminum salt by at least 5%, at least 10%, at least 20%, at least 25%, at least 30%, at least 40%, at least 50%, at least 60%, at least 70%, at least 75%, at least 80%, at least 90%, or even blocks the aggregation or re-aggregation of the aluminum salt by nearly 100% as compared to a nanoalum particle formed in the absence of the sizing agent.

In the nanoalum particles provided herein, the sizing agent is associated with the aluminum salt. In some embodiments, the sizing agent is directly bound to the aluminum salt. In some embodiments the sizing agent is adsorbed to the nanoalum particle. In some embodiments, the sizing agent is associated with the aluminum salt by ligand-exchange. In some embodiments, the sizing agent is associated with the aluminum salt by charge/electrostatic interactions. In some embodiments, the sizing agent is associated with the aluminum salt via a phosphate head group found on the sizing agent. In some embodiments, the sizing agent is further linked to a lipid. In some embodiments, the sizing agent is further linked to a phospholipid.

Table 1 provides a non-limiting list of sizing agents for inclusion in the nanoalum particles provided herein.

TABLE 1

| Acronym | Name | Structure |
|---|---|---|
| PEG | Polyethylene glycol | H—(O—CH$_2$—CH$_2$)$_n$—OH |
| PAA | Polyacrylic acid | *(structure)* |
| PCL | Polycaprolactone | *(structure)* |
| PLA | Poly(lactic) acid | *(structure)* |
| PLGA | Poly(lactic-co-glycolic acid) | *(structure)* |

TABLE 1-continued
| Acronym | Name | Structure |
|---|---|---|
| PVA | Polyvinyl alcohol | 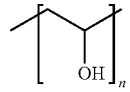 |
| PVP | Polyvinyl pyrrolidone | 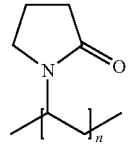 |
| Kollidon ® SR | Polymer matrix combined with PVP | 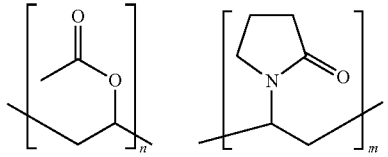 |
| Chitosan | Chitosan | 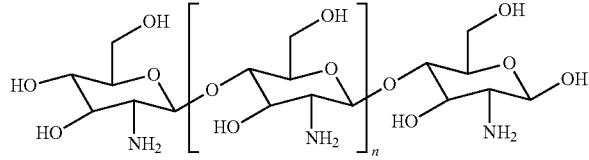 |
| Alginate | Alginate | 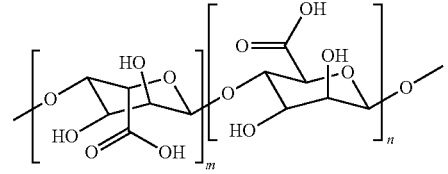 |
| Hyaluronic acid | Hyaluronic acid | 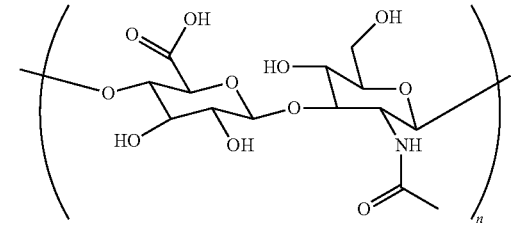 |
| PLGA-PEG-PLGA | ReGEL | 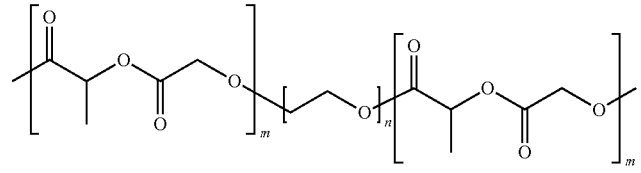 |
| PEG-PLGA-PEG | PEG-PLGA-PEG | 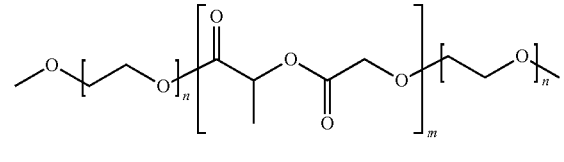 |
| Poloxamer | Poloxamer | 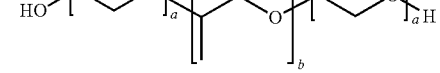 |

TABLE 1-continued

Sizing Agents

| Acronym | Name | Structure |
|---|---|---|
| Polyoxazoline | Polyoxazoline | 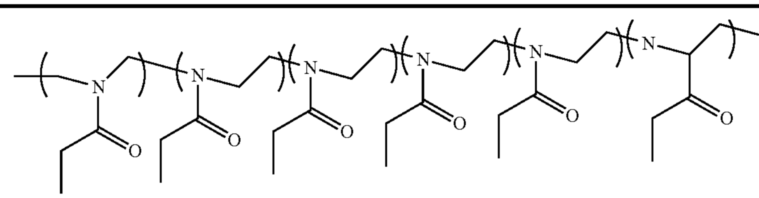 |
| PPE | Polyphosphates | 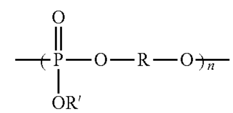 |
| Poly(lysine) | Poly(lysine) | 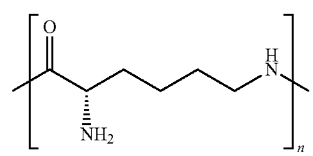 |
| PEI | Polyethyleneimine | 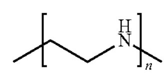 |
| Polyphospahzenes | Polyphospahzenes | 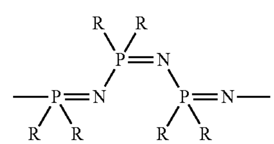 |
| Dextran sulfate (sodium salt) | Dextran sulfate | 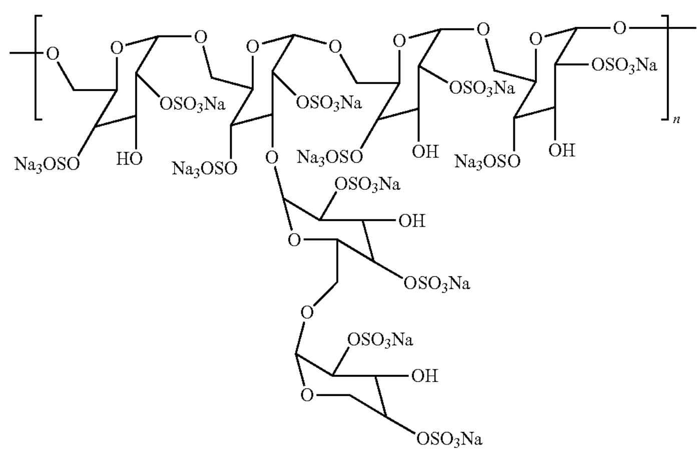 |
| Poly(allylamine) (Free base form) | Poly(allylamine) | 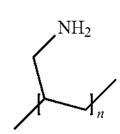 |

In some embodiments, the sizing agent is polyacrylic acid (PAA). In some embodiments, the average molecular weight of the PAA ranges from about 500 to 7000; 1000 to 7000; 1500 to 7000; 2000 to 7000; 2500 to 7000; 3000 to 7000; 3500 to 7000; 4000 to 7000; 4500 to 7000; 5000 to 7000; 5500 to 7000; 6000 to 7000; or 6500 to 7000. In some embodiments, the average molecular weight of the PAA ranges from about 500 to 1000; 500 to 1500; 500 to 2000; 500 to 2500, 500 to 3000; 500 to 3500; 500 to 4000, 500 to 4500, 500 to 5000, 500 to 5500; 500 to 6000; 500 to 6500, or 500 to 7000. In some embodiments, the average molecular weight of the PAA ranges from about 1000 to 3000 or 1500 to 2500. In some embodiments, the average molecular weight of the PAA is about 7000, 6500, 6000, 5500, 5000, 4500, 4000, 3500, 3000, 2500, 2400, 2300, 2200, 2100, 2000, 1900, 1800, 1700, 1600, 1500, 1400, 1300, 1250, 1200, 1100, 1000, or 500. In some embodiments, the average molecular weight of the PAA is about 5000, 2000, 1250, 1200, or 1000. In some embodiments, the average molecular weight of the PAA is about 2000.

In some embodiments, the sizing agent is polyethylene glycol (PEG). In some particular embodiments, the average molecular weight of the PEG or PEG length ranges from about 500 Daltons to about 6000 Daltons. In some particular embodiments, the average molecular weight of the PEG or PEG length ranges from about 750 Daltons to about 5000 Daltons. In some embodiments, the average molecular weight of the PEG or PEG length ranges from about 750 to 1000; 750 to 1500; 750 to 2000; 750 to 2500, 750 to 3000; 750 to 3500; 750 to 4000; 750 to 4500; or 750 to 5000 Daltons. In some embodiments, the average molecular weight of the PEG or PEG length ranges from about 4500 to 5000, 4000 to 5000; 3500 to 5000; 3000 to 5000; 2500 to 5000; 2000 to 5000, 1500 to 5000; 1000 to 5000; or 750 to 5000 Daltons. In some embodiments, the average molecular weight of the PEG or PEG length ranges from about 500 to 1000; 500 to 750; or 750 to 1000 Daltons. In some embodiments, the average molecular weight of the PEG or PEG length ranges from about 1500 to 2500; 1500 to 2000, or 2000 to 2500 Daltons. In some embodiments, the average molecular weight of the PEG or PEG length ranges from about 4500 to 5500; 4500 to 5000; or 5000 to 5500 Daltons. In one exemplary embodiment, the sizing agent is PEG750. In one exemplary embodiment, the sizing agent is PEG2000. In one exemplary embodiment, the sizing agent is PEG5000.

C. Lipids Linked to the Sizing Agent

In some embodiments, the sizing agent is further linked to a lipid or phospholipid. Table 2 provides a non-limiting list of lipids which can be linked to the sizing agent. In one exemplary embodiment, the sizing agent is PEG, and the PEG is linked to DSPE. In a certain embodiment, the sizing agent is PEG, and the PEG is linked to DPPE. In a certain embodiment, the sizing agent is PEG, and the PEG is linked to DMPE.

In certain embodiments, the lipid is a phospholipid or a quaternary ammonium salt lipid. In certain embodiments, the lipid is a phospholipid that is a phosphatidylcholine or a phosphoglyceride. In certain embodiments, the lipid comprises any of the following moieties:

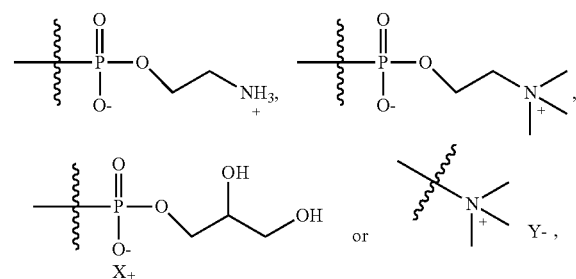

wherein $X^-$ is an alkali metal counterion and $Y^+$ is a halide counterion.

In certain embodiments, the surfactant is a poloxamer:

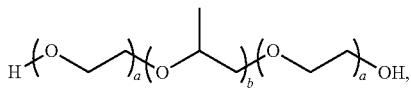

wherein a is 2-130 and b is 15-67.

In certain embodiments, the lipid comprises a $C_{10\text{-}20}$ alkyl chain. In certain embodiments, the lipid comprises a $C_{12\text{-}18}$ alkyl chain.

In certain embodiments, the lipid is anionic. In certain embodiments, the lipid is cationic. In certain embodiments, the lipid is overall neutrally charged. In certain embodiments, the lipid is a zwitterion.

In certain embodiments, suitable lipids are shown in Table 2.

TABLE 2

| Lipids | |
|---|---|
| Polysorbate 80 | (structure shown; w + x + y + z = 20) |
| Poloxamer 188 | (structure shown; a = 80 and b = 27) |
| DLPC | (structure shown) |

TABLE 2-continued
| Lipids |
|---|
| DMPC 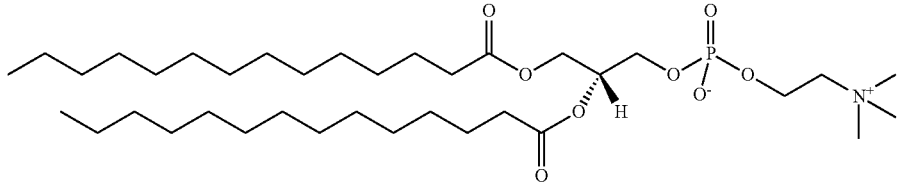 |
| DPPC 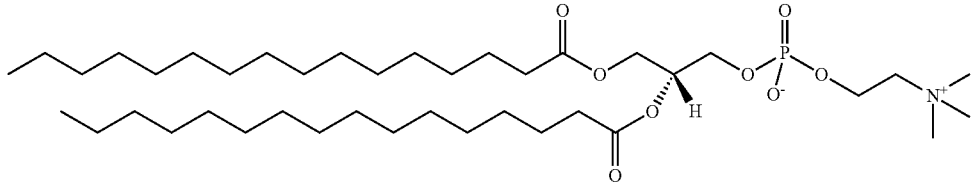 |
| DSPC 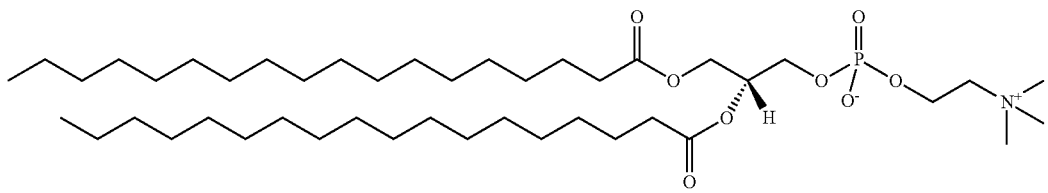 |
| DOPC 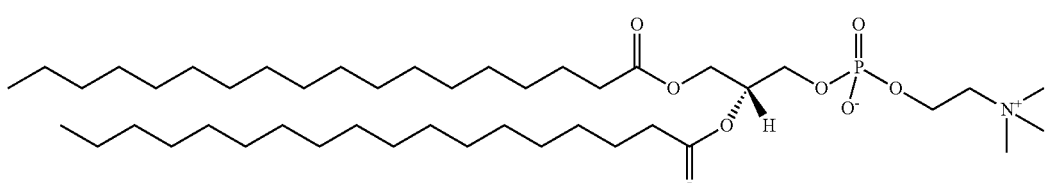 |
| POPC 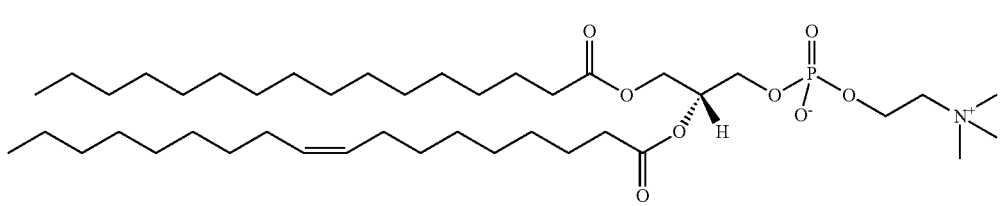 |
| DLPG 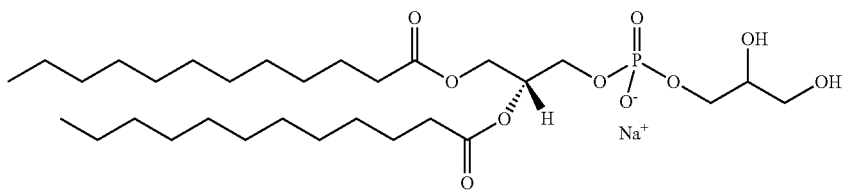 |
| DMPG 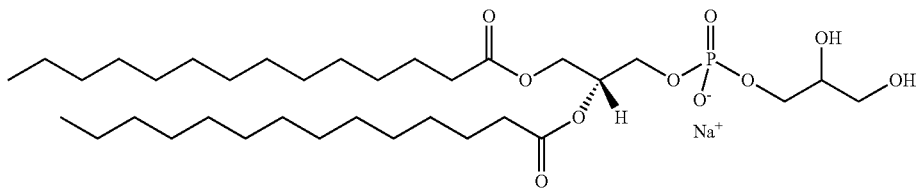 |
| DPPG 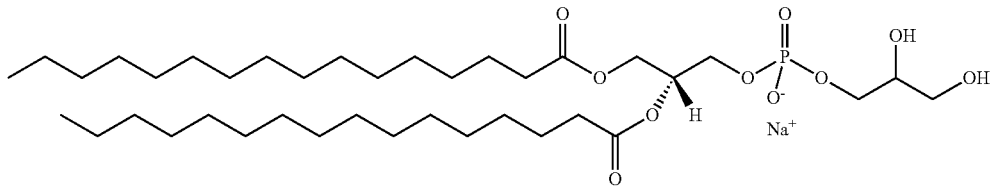 |

TABLE 2-continued

Lipids

DSPG: [structure of 1,2-distearoyl-sn-glycero-3-phosphoglycerol, sodium salt]

DOPG: [structure of 1,2-dioleoyl-sn-glycero-3-phosphoglycerol, sodium salt]

DSTAP: [structure of 1,2-distearoyl-3-trimethylammonium-propane, chloride salt]

DPTAP: [structure of 1,2-dipalmitoyl-3-trimethylammonium-propane, chloride salt]

DSPE: [structure of 1,2-distearoyl-sn-glycero-3-phosphoethanolamine]

DPPE: [structure of 1,2-dipalmitoyl-sn-glycero-3-phosphoethanolamine]

DMPE: [structure of 1,2-dimyristoyl-sn-glycero-3-phosphoethanolamine]

DLPE: [structure of 1,2-dilauroyl-sn-glycero-3-phosphoethanolamine]

In certain embodiments, the lipid is Poloxamer 188.

In certain embodiments, the lipid is selected from DLPG, DMPG, DPPG, DSPG, DOPG, DSTAP, and DPTAP. In certain embodiments, the lipid is selected from DLPG, DMPG, DPPG, DSPG, and DOPG. In certain embodiments, the lipid is selected from DSTAP and DPTAP In certain embodiments, the lipid is DSPG. In certain embodiments, the lipid is DSTAP.

In certain embodiments, the lipid is DPTAP.

In certain embodiments, the lipid is selected from DSPG, DSTAP, and Poloxamer 188.

In certain embodiments, the lipid is selected from DLPC, DMPC, DPPC, DSPC, DOPC, and POPC. In certain embodiments, the lipid is selected from DLPC, DSPC, and DOPC.

In certain embodiments the lipid is DSPG. In an exemplary embodiment, the sizing agent PEG is linked to DSPE in the nanoalum particle.

In certain embodiments the lipid is DPPE. In an exemplary embodiment, the sizing agent PEG is linked to DPPE in the nanoalum particle.

In certain embodiments the lipid is DMPE. In an exemplary embodiment, the sizing agent PEG is linked to DMPE in the nanoalum particle.

In certain embodiments, the lipid is DLPE. In an exemplary embodiment, the sizing agent PEG is linked to DLPE in the nanoalum particle.

D. Methods or Making a Nanoalum Particle

Provided herein is a nanoalum particle comprising an aluminum salt and a sizing agent, wherein the size of the nanoalum particle ranges from about 1 nm to 450 nm. The present disclosure provides methods for preparing such nanoalum particles.

The method for making a nanoalum particle comprises subjecting an aluminum salt to a high energy source or high energy sheer force in the presence of a sizing agent, whereby the size of the aluminum salt is reduced and a nanoalum particle is produced, and wherein the size of the nanoalum particle ranges from about 1 nm to 450 nm.

In certain embodiments, the alum is processed or milled in the presence of the sizing agent or that the sizing agent is added to the milled alum at least seconds, minutes, or hours after processing. In some embodiments, the alum is processed and immediately lyophilized or dried and the sizing agent is added upon reconstitution or within seconds, minutes, hours of reconstitution. Processing or milling occurs using standard techniques known in the art including sonication, high shear mixing (e.g., silverson mixing) and microfluidization. Another standard technique known in the an that can be used in the present methods is high pressure homogenization.

In some embodiments the high energy source provides at least 5000 PSI, at least 10,000 PSI, at least 15,000 PSI at least 20,000 PSI, at least 25,000 PSI, at least 30,000 PSI, at least 35,000 PSI, at least 40,000 PSI, at least 45,000 PSI, or at least 50,000 PSI. In some embodiments the high energy source provides about 5000 to 50000; 5000 to 10000; 5000 to 15000; 5000 to 20000; 5000 to 25000; 5000 to 30000; 5000 to 35000, 5000 to 40000; 5000 to 45000; or 5000 to 50000 PSI. In some embodiments the high energy source provides about 45000 to 50000; 40000 to 50000; 35000 to 50000, 30000 to 50000; 25000 to 50000, 20000 to 50000; 15000 to 50000; 10000 to 50000; or 5000 to 50000 PSI. In some embodiments the high energy source provides about 25000 to 35000; 25000 to 30000; or 30000 to 35000 PSI. In some embodiments the high energy source provides about 30000 PSI.

In some embodiments, the high energy source is a high shear source.

In some embodiments the high energy source is a microfluidizer. Microfluidization is used to describe a process in which compositions are exposed to high shear force. In some embodiments of the present disclosure, the compositions are processed by an instrument or a device known as a MICROFLUIDIZER®.

In some embodiments the high energy source is an extruder.

In some embodiments the high energy source is a sonicator.

In some embodiments the high energy source is a homogenizer.

In some embodiments the aluminum salt and the sizing agent are subjected to least 1, 2, 3, 4, 5, 6, 7, 8, 9, 10, 15, 20, 25, 30, 50, or 100 passes of the high shear force. In some embodiments the aluminum salt and the sizing agent are subjected to 1-5, 6-10, 11-15, 16-20, 21-30, 31-40, 41-50, 51-60, 61-70, 71-80, 81-90, or 91-100 passes of the high shear force. In some embodiments the aluminum salt and the sizing agent are subjected to 3, 6, or 10 passes of the high shear force.

In some embodiments, the method for making the nanoalum particles of the present disclosure is performed at 0° C., at 4° C., at 25° C., at 30° C., at 50° C., or at 60° C. In some embodiments, the method for making the nanoalum particles of the present disclosure is performed at 0-4, 5-10, 11-15, 16-20, 21-25, 26-30, 31-35, 36-40, 41-45, 46-50, 51-55, or 56-60° C. In some embodiments, the method for making the nanoalum particles of the present disclosure is performed at 14° C.

In some embodiments, the starting concentration of the aluminum salt is 10 mg/ml. In some embodiments, the starting concentration of the aluminum salt is 4 mg/ml. In some embodiments, the starting concentration of the aluminum salt is 2 mg/ml. In some embodiments, the starting concentration of the aluminum salt is 0.5 to 10 mg/ml, 1 to 10 mg/ml, 0.5 to 5 mg/ml; 1 to 5 mg/ml; 0.5 to 4 mg/ml; 0.5 to 3 mg/ml; or 0.5 to 3 mg/ml.

In some embodiments, the starting size of the aluminum salt is 1 μm. In some embodiments, the starting size of the aluminum salt is 0.5 to 5 μm; 0.5 to 4 μm; 0.5 to 3 μm; 0.5 to 2 μm; or 0.5 to 1 μm.

In some embodiments, a nanoalum particle described herein is produced by milling or processing according to methods described herein in the presence of a sizing agent, and has an average particle size of 1-450 nm. In certain embodiments, a synthetic nanoalum may include synthetic alum as has been described in the art which is de novo synthesized to produce the appropriate alum particle size to which a sizing agent of the present disclosure has been added to create a stable aqueous nanoalum formulation. Nanoalum particles of the formulation may be mixed with pharmaceutically acceptable excipients known in the art to produce nanoalum compositions or formulations.

As used herein, the terms "milling," "sizing," or "processing" refers to a process of treating a solution of alum in order to achieve nano size particles. The process includes processing an alum composition (including formulation) via high energy source or input to reduce the aggregation of the alum particles as measured by a reduced average particle size below 0.52-10 μm. Suitable examples of energy input to achieve nanoalum compositions include, but are not limited to, high shear mixing (such as ultrasonication or high shear mixing with a Silverson high shear mixer), extrusion, homogenization and microfluidization. In some embodiments, high shear mixing is performed at 1000, 2000, 5000, or 10,000 rpms for 1 minute, 2 minutes, 5 minutes, or 10 minutes. In some embodiments, the microfluidizer is a Microfluidics M110P (Newton, MA), equipped with a diamond F12Y interaction chamber followed by a ceramic H30Z auxiliary processing module. In some embodiments, the alum compositions are microfluidized at pressures of 3,000 PSI 5,000 PSI, 10,000 PSI, 15,000 PSI, or 30,000 PSI. In some embodiments, the solution of alum is processed by a microfluidizer with a recirculation water water temperature of 60° C., 40° C., 20° C. or 4° C. to achieve nanoalum compositions. In some embodiments, the solution of alum is milled or processed at least about 1, 3, 6, 10, 15, 20, or 30 passages to reproducibly achieve nanoparticles of the present disclosure having an average particle size of 1-450 nm in size. In some embodiments, the solution of alum is microfluidized for up to 10 passages at 30,000 PSI with a recirculating 4° C. water to prevent temperature increase during processing. In some embodiment, the solution of alum is processed in the presence of the sizing agent. In some embodiments, the ratio of the sizing agent to alum is 30:1, 20:1, 15:1, 10:1, 7.5:1, 4:1, 3:1, 2:1, 1.5:1, 0.5:1, or 0.25:1. In some embodiments, the ratio of the sizing agent to alum is 7.5:1, 4:1, 3:1, 2:1 or 1:1.

It is understood that certain variables can be controlled in a method of preparing a nanoalum particle of the embodiments. Certain variables include, but are not limited to, the sizing agent, the type of high energy source, the pressure exerted by the high energy source, the number of passes of the mixture through the high energy source, the temperature at which the process takes place, the concentration of sizing agent, the point in the method wherein the sizing agent is added to the aluminum, and the ratio of the aluminum salt to the sizing agent by weight.

TABLE 3

Effect of PEG Lengths or Molecular Weight and Milling Process on Sizing Agent

| PEG Length | Sizing Agent mg/ml | *Ratio Alum:Sizing Agent | Z-Ave (d · nm) ± Error | | | PdI ± Error | | | Comments |
|---|---|---|---|---|---|---|---|---|---|
| | | | 3 P | 6 P | 10 P | 3 P | 6 P | 10 P | |
| PEG5000 | 4 | 1:1 | 329 ± 4.3 | 287 ± 5.6 | 514 ± 9.3 | 0.4 ± 0.012 | 0.39 ± 0.009 | 0.31 ± 0.009 | |
| | 4 | 1:1 | 333 ± 3.7 | 288 ± 4 | 260 ± 2.8 | 0.45 ± 0.013 | 0.37 ± 0.053 | 0.3 ± 0.001 | Silverson (5 k, 5') |
| | 4 | 1:1 | 304 ± 8.9 | 349 ± 3.8 | 214 ± 0.2 | 0.41 ± 0.038 | 0.5 ± 0.008 | 0.28 ± 0.007 | 60° C. water bath |
| | 4 | 1:1 | 368 ± 16 | 296 ± 5.9 | 376 ± 5.3 | 0.48 ± 0.006 | 0.32 ± 0.006 | 0.37 ± 0.059 | 20° C.-110 P |
| | 4 | 1:1 | 218 ± 4.5 | 203 ± 6.7 | 192 ± 4.9 | 0.32 ± 0.04 | 0.35 ± 0.014 | 0.27 ± 0.016 | 40° C.-110 P |
| | 3 | 1:1 | 244 ± 10 | 184 ± 4.6 | 340 ± 3 | 0.37 ± 0.008 | 0.3 ± 0.033 | 0.51 ± 0.031 | 20° C.-110 P |
| | 4 | 1:1 | 261 ± 14.7 | 227 ± 8.4 | 401 ± 8.6 | 0.42 ± 0.038 | 0.38 ± 0.05 | 0.59 ± 0.101 | 40° C.-110 P |
| | 4 | 1:1 | 395 ± 24.2 | 541 ± 16.9 | 995 ± 46.9 | 0.52 ± 0.02 | 0.57 ± 0.039 | 0.71 ± 0.075 | 4° C.-110 P |
| | 6 | 1:1.5 | 106 ± 3.9 | 102 ± 2 | 100 ± 1.9 | 0.26 ± 0.009 | 0.25 ± 0.005 | 0.24 ± 0.027 | 4° C.-110 P |
| | 8 | 1:2 | 81 ± 1.7 | 73 ± 0.5 | 68 ± 0.4 | 0.18 ± 0.015 | 0.17 ± 0.012 | 0.16 ± 0.007 | 4° C.-110 P |
| | 8 | 1:2 | 79 ± 1.7 | 72 ± 1.2 | 69 ± 1.3 | 0.14 ± 0.015 | 0.16 ± 0.032 | 0.15 ± 0.009 | 4° C.-110 P |
| | 8 | 1:2 | 79 ± 2 | 72 ± 1.7 | 67 ± 1.6 | 0.14 ± 0.012 | 0.15 ± 0.016 | 0.15 ± 0.009 | 4° C. 110 P |
| | 8 | 1:2 | LP** 130 – 120 | | | | | | 4° C. 110 P |
| | 8 | 1:2 | 1-10 μm ***Microfluidize lipid alone bench top mix with alum | | | | | | 4° C. 110 P |
| PEG2000 | 1.9 | ~1:0.5 | 901 ± 24 | 875 ± 10 | 907 ± 64 | 0.2 ± 0.011 | 0.25 ± 0.011 | 0.37 ± 0.078 | 4° C. 110 P |
| | 3.8 | ~1:1 | 2472 ± 68.2 | 1999 ± 88 | 1709 ± 13.8 | 0.24 ± 0.076 | 0.24 ± 0.026 | 0.31 ± 0.015 | 4° C. 110 P |
| | 6 | 1:1.5 | 1755 ± 43.2 | 2020 ± 137.3 | 1974 ± 90 | 0.38 ± 0.01 | 0.22 ± 0.162 | 0.1 ± 0.063 | 4° C. 110 P |
| | 8 | 1:2 | 1742 ± 192.7 | 2106 ± 94 | 2318 ± 241.3 | 0.3 ± 0.129 | 0.48 ± 0.057 | 0.55 ± 0.066 | 4° C. 110 P |
| | 10 | 1:2.5 | 78 ± 0.2 | 75 ± 0.2 | 77 ± 0.5 | 0.21 ± 0.002 | 0.19 ± 0.004 | 0.17 ± 0.004 | 4° C. 110 P |
| PEG750 | 1 | 1:0.25 | 1206 ± 8 | 1025 ± 24 | 1005 ± 55 | 0.2 ± 0.031 | 0.22 ± 0.08 | 0.27 ± 0.087 | 4° C. 110 P |
| | 2 | 1:0.5 | 910 ± 73 | 1080 ± 26.7 | 1086 ± 56.8 | 0.42 ± 0.084 | 0.26 ± 0.04 | 0.31 ± 0.111 | 4° C. 110 P |
| | 4 | 1:1 | 2080 ± 13.3 | 986 ± 37.2 | 1909 ± 120.7 | 0.15 ± 0.016 | 0.58 ± 0.019 | 0.55 ± 0.082 | 4° C. 110 P |
| | 10 | 1:2.5 | 530 ± 44.1 | 454 ± 0.4 | 741 ± 43.4 | 0.85 ± 0.207 | 0.91 ± 0.017 | 0.8 ± 0.047 | 4° C. 110 P |
| | 20 | 1:5 | 102 ± 1.1 | 91 ± 1.2 | 79 ± 0.7 | 0.24 ± 0.003 | 0.24 ± 0.006 | 0.24 ± 0.006 | 4° C. 110 P |
| | 30 | 1:7.5 | 100 ± 1.9 | 86 ± 0.6 | 80 ± 1 | 0.23 ± 0.009 | 0.24 ± 0.006 | 0.24 ± 0.013 | 4° C. 110 P |
| PAA2000 | 4.8 | *1:3 | | | 76.33 ± | | | | 4° C. 110 P |

*Alum is a 4 mg/ml solution except for PAA in which the alum is 1.6 mg/ml.
Bolded Sizing Agent mg/ml, Ratio Alum:Sizing Agent and Z-Ave (d · nm) ± Error) values in Table 3 represent conditions which produce nanoalums of the present disclosure.

It is understood that certain variables and combinations thereof can be involved in a method of preparing a nanoalum particle of the embodiments, such as shown in Table 3.

In certain embodiments, for the method of preparing a nanoalum particle, where the sizing agent is PEG5000, the method may have any one or more of the following features:

a) the type of high energy source is microfluidizer;
b) the pressure exerted by the high energy source is about 30 k psi;
c) the number of passes of the mixture through the high energy source is 1 to 10, such as 3, 6, or 10 passes;
d) the temperature at which the process takes place is about 4° C.;
e) the concentration of alum is about 4 mg/ml
f) the concentration of sizing agent is about 8 mg/ml; and
g) the ratio of the aluminum salt to the sizing agent is about 1:2.

In one variation, the method conforms to at least one of features (a)-(g). In another variation, the method conforms to two or more (and in certain variations, all) of features (a)-(g) (g). In a particular variation, the method conforms to feature (a). In another variation, the method conforms to features (a), (b), and (c). In another variation, the method conforms to features (a), (b), (c), and (d). In another variation, the method conforms to features (a), (b), (c), (d), and (e). In another variation, the method conforms to features (a), (b), (c), (d), and (f). In another variation, the method conforms to features (a), (b), (c). (d), and (g).

In certain embodiments, for the method of preparing a nanoalum particle, where the sizing agent is PEG2000, the method may have any one or more of the following features:
 a) the type of high energy source is microfluidizer;
 b) the pressure exerted by the high energy source is about 30 k psi;
 c) the number of passes of the mixture through the high energy source is 1 to 10, such as 3, 6, or 10 passes;
 d) the temperature at which the process takes place is about 4° C.;
 e) the concentration of alum is 4 mg/ml;
 f) the concentration of sizing agent is about 10 mg/ml; and
 g) the ratio of the aluminum salt to the sizing agent is about 1:2.5.

In one variation, the method conforms to at least one of features (a)-(g). In another variation, the method conforms to two or more (and in certain variations, all) of features (a)-(g). In a particular variation, the method conforms to feature (a). In another variation, the method conforms to features (a), (b), and (c). In another variation, the method conforms to features (a), (b), (c), and (d). In another variation, the method conforms to features (a), (b), (c), (d), and (e). In another variation, the method conforms to features (a), (b), (c), (d), and (f). In another variation, the method conforms to features (a), (b), (c), (d), and (g).

In certain embodiments, for the method of preparing a nanoalum particle, where the sizing agent is PEG750, the method may have any one or more of the following features.
 a) the type of high energy source is microfluidizer;
 b) the pressure exerted by the high energy source is about 30 k psi;
 c) the number of passes of the mixture through the high energy source is 1 to 10, such as 3, 6, or 10 passes;
 d) the temperature at which the process takes place is about 4° C.;
 e) the concentration of alum is 4 mg/ml;
 f) the concentration of sizing agent is about 30 mg/ml; and
 g) the ratio of the aluminum salt to the sizing agent is about 1:7.5.

In one variation, the method conforms to at least one of features (a)-(g). In another variation, the method conforms to two or more (and in certain variations, all) of features (a)-(g). In a particular variation, the method conforms to feature (a). In another variation, the method conforms to features (a), (b), and (c). In another variation, the method conforms to features (a), (b), (c), and (d). In another variation, the method conforms to features (a), (b), (c), (d), and (e). In another variation, the method conforms to features (a), (b), (c), (d), and (f). In another variation, the method conforms to features (a), (b), (c), (d), and (g).

In certain embodiments, for the method of preparing a nanoalum particle, where the sizing agent is PEG750, the method may have any one or more of the following features:
 a) the type of high energy source is microfluidizer;
 b) the pressure exerted by the high energy source is about 30 k psi;
 c) the number of passes of the mixture through the high energy source is 1 to 10, such as 3, 6, or 10 passes;
 d) the temperature at which the process takes place is about 4° C.;
 e) the concentration of alum is 4 mg/ml;
 f) the concentration of sizing agent is about 20 mg/ml; and
 g) the ratio of the aluminum salt to the sizing agent is about 1:5

In one variation, the method conforms to at least one of features (a)-(f). In another variation, the method conforms to two or more (and in certain variations, all) of features (a)-(f). In a particular variation, the method conforms to feature (a). In another variation, the method conforms to features (a), (b) and (c). In another variation, the method conforms to features (a), (b), (c), and (d). In another variation, the method conforms to features (a), (b), (c), (d), and (e). In another variation, the method conforms to features (a), (b), (c), (d), and (f). In another variation, the method conforms to features (a), (b), (c), (d), and (g).

In certain embodiments, for the method of preparing a nanoalum particle, where the sizing agent is PAA, the method may have any one or more of the following features:
 a) the type of high energy source is microfluidizer;
 b) the pressure exerted by the high energy source is about 30 k psi;
 c) the number of passes of the mixture through the high energy source is 1 to 10, such as 3, 6, or 10 passes;
 d) the temperature at which the process takes place is about 4° C.;
 e) the concentration of alum is 1.6 mg/ml;
 f) the concentration of sizing agent is about 4.8 mg/ml; and
 g) the ratio of the aluminum salt to the sizing agent is about 1:3.

In one variation, the method conforms to at least one of features (a)-(f). In another variation, the method conforms to two or more (and in certain variations, all) of features (a)-(f). In a particular variation, the method conforms to feature (a). In another variation, the method conforms to features (a), (b), and (c). In another variation, the method conforms to features (a), (b), (c), and (d). In another variation, the method conforms to features (a), (b), (c), (d), and (e). In another variation, the method conforms to features (a), (b), (c), (d), and (f). In another variation, the method conforms to features (a), (b), (c), (d), and (g).

TABLE 4

Acyl Chain Length Effect on Lipid Affect Sizing Agent

| PEG Length | Sizing Agent mg/ml | *Ratio Alum:Sizing Agent | Z-Ave (d · nm) ± Error | | | PdI ± Error | | |
|---|---|---|---|---|---|---|---|---|
| | | | 3 P | 6 P | 10 P | 3 P | 6 P | 10 P |
| DSPE- | 4 | 1:1 | 329 ± 4.3 | 287 ± 5.6 | 514 ± 9.3 | 0.4 ± 0.012 | 0.39 ± 0.009 | 0.31 ± 0.009 |
| 18C | 4 | 1:1 | 333 ± 3.7 | 288 ± 4 | 260 ± 2.8 | 0.45 ± 0.013 | 0.37 ± 0.053 | 0.3 ± 0.001 |
| PEG5000 | 4 | 1:1 | 395 ± 24.2 | 541 ± 16.9 | 995 ± 46.9 | 0.52 ± 0.02 | 0.57 ± 0.039 | 0.71 ± 0.075 |
| | 6 | 1:1.5 | 106 ± 3.9 | 102 ± 2 | 100 ± 1.9 | 0.26 ± 0.009 | 0.25 ± 0.005 | 0.24 ± 0.027 |
| | 8 | 1:2 | 81 ± 1.7 | 73 ± 0.5 | 68 ± 0.4 | 0.18 ± 0.015 | 0.17 ± 0.012 | 0.16 ± 0.007 |

TABLE 4-continued

Acyl Chain Length Effect on Lipid Affect Sizing Agent

| PEG Length | Sizing Agent mg/ml | *Ratio Alum:Sizing Agent | Z-Ave (d · nm) ± Error | | | PdI ± Error | | |
|---|---|---|---|---|---|---|---|---|
| | | | 3 P | 6 P | 10 P | 3 P | 6 P | 10 P |
| | 8 | 1:2 | 79 ± 1.7 | 72 ± 1.2 | 69 ± 1.3 | 0.14 ± 0.015 | 0.16 ± 0.032 | 0.15 ± 0.009 |
| | 8 | 1:2 | 79 ± 2 | 72 ± 1.7 | 67 ± 1.6 | 0.14 ± 0.012 | 0.15 ± 0.016 | 0.15 ± 0.009 |
| DSPE-18C PEG2000 | 1.9 | ~1:0.5 | 901 ± 24 | 875 ± 10 | 907 ± 64 | 0.2 ± 0.011 | 0.25 ± 0.011 | 0.37 ± 0.078 |
| | 3.8 | ~1:1 | 2472 ± 68.2 | 1999 ± 88 | 1709 ± 13.8 | 0.24 ± 0.076 | 0.24 ± 0.026 | 0.31 ± 0.015 |
| | 6 | 1:1.5 | 1755 ± 43.2 | 2020 ± 137.3 | 1974 ± 90 | 0.38 ± 0.01 | 0.22 ± 0.162 | 0.1 ± 0.063 |
| | 8 | 1:2 | 1742 ± 192.7 | 2106 ± 94 | 2318 ± 241.3 | 0.3 ± 0.129 | 0.48 ± 0.057 | 0.55 ± 0.066 |
| | 10 | 1:2.5 | 78 ± 0.2 | 75 ± 0.2 | 77 ± 0.5 | 0.21 ± 0.002 | 0.19 ± 0.004 | 0.17 ± 0.004 |
| DPPE-16C PEG5000 | 1 | 1:0.25 | 409 ± 14.1 | 371 ± 10.3 | 412 ± 6.6 | 0.32 ± 0.03 | 0.32 ± 0.02 | 0.36 ± 0.02 |
| | 2 | 1:0.5 | 365 ± 16 | 312 ± 14.7 | 322 ± 9.6 | 0.44 ± 0.05 | 0.5 ± 0.03 | 0.45 ± 0.06 |
| | 3 | 1:0.75 | 130 ± 8.2 | 126 ± 2.3 | 141 ± 1.6 | 0.32 ± 0.04 | 0.35 ± 0.01 | 0.35 ± 0.04 |
| | 4 | 1:1 | 76 ± 0.2 | 74 ± 0.1 | 73 ± 0.3 | 0.1 ± 0.013 | 0.1 ± 0.008 | 0.09 ± 0.005 |
| | 4 | 1:1 | 84 ± 1 | 81 ± 0.3 | 81 ± 0.7 | 0.14 ± 0.004 | 0.12 ± 0.009 | 0.14 ± 0.006 |
| | 4 | 1:1 | 79 ± 0.5 | 77 ± 0.27 | 78 ± 0.22 | 0.1 ± 0.004 | 0.11 ± 0.007 | 0.12 ± 0.006 |
| | 8 | 1:2 | 74 ± 0.6 | 70 ± 0.3 | 67 ± 0.3 | 0.09 ± 0.015 | 0.11 ± 0.017 | 0.1 ± 0.021 |
| | 8 | 1:2 | 77 ± 0.5 | 81 ± 2.1 | 70 ± 1.1 | 0.1 ± 0.004 | 0.2 ± 0.019 | 0.09 ± 0.016 |
| | 8 | 1:2 | 75 ± 0.4 | 71 ± 0.4 | 68 ± 0.2 | 0.09 ± 018 | 0.1 ± 0.023 | 0.09 ± 0.006 |
| DPPE-16C PEG2000 | 1.9 | ~1:0.5 | 1217 ± 91.3 | 117 ± 84.8 | 1191 ± 44.8 | 0.11 ± 0.056 | 0.2 ± 0.021 | 0.2 ± 0.019 |
| | 4 | 1:1 | 1463 ± 92.9 | 1739 ± 272.7 | 1668 ± 125.3 | 0.34 ± 0.047 | 0.21 ± 0.029 | 0.46 ± 0.249 |
| | 8 | 1:2 | 413 ± 115. | 1299 ± 158.2 | 2005 ± 424.1 | 0.41 ± 0.102 | 0.52 ± 0.05 | 0.56 ± 0.109 |
| | 10 | 1:2.5 | 91 ± 1.5 | 92 ± 1.2 | 97 ± 1.1 | 0.22 ± 0.013 | 0.18 ± 0.011 | 0.17 ± 0.015 |
| DMPE-14C Peg 2000 | 1.9 | ~1:0.5 | 1282 ± 31.1 | 1492 ± 51 | 956 ± 3.9 | 0.41 ± 0.081 | 0.08 ± 0.051 | 0.47 ± 0.018 |
| | 4 | 1:1 | 1135 ± 157.7 | 1421 ± 56 | 1288 ± 86.6 | 0.37 ± 0.05 | 0.35 ± 0.036 | 0.33 ± 0.03 |
| | 6 | 1:1.5 | 2928 ± 73.8 | 2405 ± 240.6 | 3644 ± 469.6 | 0.47 ± 0.137 | 0.33 ± 0.234 | 0.54 ± 0.313 |
| | 8 | 1:2 | 145 ± 6.1 | 254 ± 15.4 | 812 ± 98.3 | 0.2 ± 0.004 | 0.28 ± 0.005 | 0.62 ± 0.024 |
| | 8 | 1:2 | 295 ± 19.5 | 872 ± 112.3 | 1659 ± 143.3 | 0.3 ± 0.016 | 0.56 ± 0.041 | 0.46 ± 0.075 |
| | 10 | 1:25 | 78 ± 0.2 | 75 ± 0.2 | 77 ± 0.5 | 0.210 ± .002 | 0.19 ± 0.004 | 0.170 ± .004 |

*Alum is a 4 mg/ml solution.
Bolded Sizing Agent mg/ml, Ratio Alum:Sizing Agent and Z-Ave (d · nm) ± Error) values in Table 3 represent conditions which produce nanoalums of the present disclosure.

It is understood that certain variables and combinations thereof can be involved in a method of preparing a nanoalum particle of the embodiments, such as shown in Table 4.

In certain embodiments, for the method of preparing a nanoalum particle, where the sizing agent is PEG5000 with DSPE-18C, the method may have any one or more of the following features:
a) the type of high energy source is microfluidizer;
b) the pressure exerted by the high energy source is about 30 k psi;
c) the number of passes of the mixture through the high energy source is 1 to 10, such as 3, 6, or 10 passes;
d) the concentration of sizing agent is about 8 mg/ml; and
e) the ratio of the aluminum salt to the sizing agent is about 1:2.

In one variation, the method conforms to at least one of features (a)-(e). In another variation, the method conforms to two or more (and in certain variations, all) of features (a)-(e). In a particular variation, the method conforms to feature (a). In another variation, the method conforms to features (a), (b), and (c). In another variation, the method conforms to features (a), (b), (c), and (d). In another variation, the method conforms to features (a), (b), (c), and (e).

In certain embodiments, for the method of preparing a nanoalum particle, where the sizing agent is PEG2000 with DSPE-18C, the method may have any one or more of the following features:
a) the type of high energy source is microfluidizer;
b) the pressure exerted by the high energy source is about 30 k psi;
c) the number of passes of the mixture through the high energy source is 1 to 10, such as 3, 6, or 10 passes;
d) the concentration of siring agent is about 10 mg/ml; and
e) the ratio of the aluminum salt to the sizing agent is about 1:2.5.

In one variation, the method conforms to at least one of features (a)-(e). In another variation, the method conforms to two or more (and in certain variations, all) of features (a)-(e). In a particular variation, the method conforms to feature (a). In another variation, the method conforms to features (a), (b), and (c). In another variation, the method conforms to features (a), (b), (c), and (d). In another variation, the method conforms to features (a), (b), (c), and (e).

In certain embodiments, for the method of preparing a nanoalum particle, where the siring agent is PEG5000 with DPPE-16C. the method may have any one or more of the following features:
a) the type of high energy source is microfluidizer;
b) the pressure exerted by the high energy source is about 30 k psi;
c) the number of passes of the mixture through the high energy source is 1 to 10, such as 3, 6, or 10 passes;
d) the concentration of sizing agent is about 1 mg/ml to about 8 mg/ml, such as 4 or 8 mg/ml; and
e) the ratio of the aluminum salt to the sizing agent is about 1:1 or 1:2.

In one variation, the method conforms to at least one of features (a)-(e). In another variation, the method conforms to two or more (and in certain variations, all) of features (a)-(e). In a particular variation, the method conforms to feature (a). In another variation, the method conforms to features (a), (b), and (c). In another variation, the method conforms to features (a), (b), (c), and (d). In another variation, the method conforms to features (a), (b), (c), and (e).

In certain embodiments, for the method of preparing a nanoalum particle, where the sizing agent is PEG2000 with DPPE-16C, the method may have any one or more of the following features:

a) the type of high energy source is microfluidizer;
b) the pressure exerted by the high energy source is about 30 k psi;
c) the number of passes of the mixture through the high energy source is 1 to 10, such as 3, 6, or 10 passes;
d) the concentration of sizing agent is about 10 mg/ml; and
e) the ratio of the aluminum salt to the sizing agent is about 1:2.5.

In one variation, the method conforms to at least one of features (a)-(e). In another variation, the method conforms to two or more (and in certain variations, all) of features (a)-(e). In a particular variation, the method conforms to feature (a). In another variation, the method conforms to features (a), (b), and (c). In another variation, the method conforms to features (a), (b), (c), and (d). In another variation, the method conforms to features (a), (b), (c), and (e).

In certain embodiments, for the method of preparing a nanoalum particle, where the sizing agent is PEG2000 with DMPE-14C, the method may have any one or more of the following features:
a) the type of high energy source is microfluidizer;
b) the pressure exerted by the high energy source is about 30 k psi;
c) the number of passes of the mixture through the high energy source is 1 to 10, such as 3, 6, or 10 passes;
d) the concentration of sizing agent is about 10 mg/ml; and
e) the ratio of the aluminum salt to the sizing agent is about 1:25.

In one variation, the method conforms to at least one of features (a)-(e). In another variation, the method conforms to two or more (and in certain variations, all) of features (a)-(e). In a particular variation, the method conforms to feature (a). In another variation, the method conforms to features (a), (b), and (c). In another variation, the method conforms to features (a), (b), (c), and (d). In another variation, the method conforms to features (a), (b), (c), and (e).

In certain embodiments, for the method of preparing a nanoalum particle, where the sizing agent is chitosan and the aluminum salt is Al(OH)(PO$_4$) (e.g., AdjuPhos®), the method may have any combination of the following features:
a) the type of high energy source is a high shear mixer followed by a microfluidizer;
b) the pressure exerted by the high energy source is about 30 k psi;
c) the number of passes of the mixture through the microfluidizer is 1-30, preferably from 10 to 30;
d) the high shear mixer mixes at about 5,000 rpm
e) the concentration of alum is about 2 mg aluminum/ml
f) the concentration of sizing agent is about 2 mg/ml; and
g) the mass ratio of the aluminum salt to the sizing agent is about 1:1
h) the sizing agent is low molecular weight chitosan.

In certain embodiments, for the method of preparing a nanoalum particle, where the sizing agent is dextran (e.g., dextran sulfate sodium salt) and the aluminum salt is AlO(OH) (e.g., Alhydrogel®), the method may have any combination of the following features:
a) the type of high energy source is a high shear mixer followed by a microfluidizer;
b) the pressure exerted by the high energy source is about 30 k psi;
c) the number of passes of the mixture through the microfluidizer is 1-30, preferably from 10 to 30;
d) the high shear mixer mixes at about 5,000 rpm
e) the concentration of alum is about 2 mg aluminum/ml
f) the concentration of sizing agent is about 0.5 mg/ml (e.g., 0.44 mg/ml); and
g) the mass ratio of the aluminum salt to the sizing agent is about 4.5:1
h) the sizing agent is low molecular weight dextran sulfate sodium salt.

In certain embodiments, for the method of preparing a nanoalum particle, where the sizing agent is chitosan and the aluminum salt is AlO(OH) (e.g., Alhydrogel®), the method may have any combination of the following features:
a) the type of high energy source is a high shear mixer followed by a microfluidizer;
b) the pressure exerted by the high energy source is about 30 k psi;
c) the number of passes of the mixture through the microfluidizer is 1-30, preferably from 10 to 30;
d) the high shear mixer mixes at about 5,000 rpm
e) the concentration of alum is about 2 mg aluminum/ml
f) the concentration of sizing agent is about 1 mg/ml; and
g) the mass ratio of the aluminum salt to the sizing agent is about 2:1
h) the sizing agent is low molecular weight chitosan.
i) prior to mixing the aluminum salt and the sizing agent, the aluminum salt is subject to ligand exchange (e.g., phosphate ligand exchange)

In certain embodiments, for the method of preparing a nanoalum particle, where die sizing agent is poly(allylamine) and the aluminum salt is AlO(OH) (e.g., Alhydrogel®), the method may have any combination of the following features:
a) the type of high energy source is a high shear mixer followed by a microfluidizer;
b) the pressure exerted by the high energy source is about 30 k psi;
c) the number of passes of the mixture through the microfluidizer is 1-30, preferably from 10 to 30;
d) the high shear mixer mixes at about 5,000 rpm
e) the concentration of alum is about 2 mg aluminum/ml
f) the concentration of sizing agent is about 0.5 mg/ml; and
g) the mass ratio of the aluminum salt to the sizing agent is about 4:1
h) the sizing agent is about 15 kDa
i) prior to mixing the aluminum salt and the sizing agent, the aluminum salt is subject to ligand exchange (e.g., phosphate ligand exchange).

E. Size of Nanoalum Particles

As provided herein, the size of the nanoalum particle comprising an aluminum salt and a sizing agent ranges from about 1 nm to 450 nm.

In some embodiments the size of the nanoalum particle ranges from about 50 nm to 75 nm. In some embodiments the size of the nanoalum particle ranges from about 50 nm to 100 nm. In some embodiments the size of the nanoalum particle ranges from about 50 nm to 150 nm. In some embodiments the size of the nanoalum particle ranges from about 50 nm to 200 nm. In some embodiments the size of the nanoalum particle ranges from about 50 nm to 300 nm. In some embodiments the size of the nanoalum particle ranges from about 50 nm to 400 nm. In some embodiments the size of the nanoalum particle ranges from about 50 nm to 450 nm. In some embodiments the size of the nanoalum particle ranges from about 20 nm to 100 nm. In some embodiments the size of the nanoalum particle ranges from about 20 nm to 50 nm. In some embodiments the size of the nanoalum particle ranges from about 10 nm to 200 nm. In some embodiments the size of the nanoalum particle ranges from about 10 nm to 100 nm. In some embodiments the size of the nanoalum particle ranges from about 10 nm to 50 nm. In some embodiments the size of the nanoalum particle is about 1 nm, is about 5 nm, is about 10 nm, is about 15 nm, is about 20 nm, is about 25 nm, is about 30 nm, is about 35 nm, is about 40 nm, is about 45 nm, is about 50 nm, is about 55 nm, is about 60 nm, is about 65 nm, is about 70 nm, is about 75 nm, is about 80 nm, is about 85 nm, is about 90 nm, is about 95 nm, is about 100 nm, is about 105 nm, is about 110 nm, is about 115 nm, is about 120 nm, is about 125 nm, is about 130 nm, is about 135 nm, is about 140 nm, is about 145 nm, is about 150 nm, is about 155 nm, is about 160 nm, is about 165 nm, is about 170 nm, is about 175 nm, is about 180 nm, is about 185 nm, is about 190 nm, is about 195 nm, is about 200 nm, is about 210 nm, is about 220 nm, is about 240 nm, is about 250 nm, is about 260 nm, is about 280 nm, is about 200 nm, is about 300 nm, is about 320 nm, is about 340 nm, is about 350 nm, is about 360 nm, is about 380 nm, is about 400 nm, is about 420 nm, is about 440 nm, or is about 450 nm. In some embodiments, the size of the nanoalum particle is no greater than about 1 nm, no greater than about 5 nm, no greater than about 10 nm, no greater than about 15 nm, no greater than about 20 nm, no greater than about 25 nm, no greater than about 30 nm, no greater than about 35 nm, no greater than about 40 nm, no greater than about 45 nm, no greater than about 50 nm, no greater than about 55 nm, no greater than about 60 nm, no greater than about 65 nm, no greater than about 70 nm, no greater than about 75 nm, no greater than about 80 nm, no greater than about 85 nm, no greater than about 90 nm, no greater than about 95 nm, no greater than about 100 nm, no greater than about 105 nm, no greater than about 110 nm, no greater than about 115 nm, no greater than about 120 nm, no greater than about 125 nm, no greater than about 130 nm, no greater than about 135 nm, no greater than about 140 nm, no greater than about 145 nm, no greater than about 150 nm, no greater than about 155 nm, no greater than about 160 nm, no greater than about 165 nm, no greater than about 170 nm, no greater than about 175 nm, no greater than about 180 nm, no greater than about 185 nm, no greater than about 190 nm, no greater than about 195 nm, no greater than about 199 nm, no greater than about 210 nm, no greater than about 230 nm, no greater than about 250 nm, no greater than about 270 nm, no greater than about 290 nm, no greater than about 310 nm, no greater than about 330 nm, no greater than about 350 nm, no greater than about 370 nm, no greater than about 390 nm, no greater than about 410 nm, no greater than about 430 nm, no greater than about 440 nm, or no greater than about 449 nm, or no greater than about 450 nm.

In some embodiments, the nanoalum particle is capable of being filtered through at least a 0.45 micron filter. In some embodiments, the nanoalum particle is capable of being filtered through a 0.45 micron or smaller pore size filter. In some embodiments, the nanoalum particle is capable of being filtered through a 0.45 micron filter. In some embodiments, the nanoalum particle is capable of being filtered through a 0.20 micron filter. In some embodiments, the nanoalum particle is capable of being filtered through a 0.22 micron filter.

F. Stability

In some embodiments provided herein, the 1-450 nm size of the nanoalum particle comprising an aluminum salt and a sizing agent is stable, in that the nanoalum particle's size of less than 450 nm is maintained, and in that the aluminum salt exhibits reduced aggregation, or no aggregation, when compared to an aluminum salt in the absence of a sizing agent.

In some embodiments, "stable" refers to a nanoalum formulation or composition comprised of nanoalum particles which does not "aggregate" displays little to no aggregation, or reduced aggregation and or demonstrates little to no overall increase in average particle size or polydispersity of the formulation over time compared to the initial particle size.

The stability of the nanoalum particle can be measured by techniques familiar to those of skill in the art. In some embodiments, the stability is observed visually. Visual inspection can include inspection for particulates, flocculence, or aggregates. In some embodiments, the stability is determined by the size of the nanoalum particle. For example, the size can be assessed by known techniques in the art, including but not limited to, x-ray and laser diffraction, dynamic light scattering (DLS), CryoEM, or Malvern Zetasize. In some embodiments, the size of the nanoalum particle refers to the Z-average diameter. In some embodiments, the stability is determined by assessing the % aggregation of the aluminum salts in the nanoalum particle. In some embodiments, the stability is assessed by the ability of the nanoalum particle to pass through a filter of a particular size, for example through a 0.20, 0.22, or 0.45 micron filter. In some embodiments, stability is determined by pH. In some embodiments, stability is determined by measurement of the polydispersity index (PdI), for example with the use of the dynamic light scattering (DLS) technique.

In some embodiments, the Z-average diameter of the nanoparticle increases less than 50%, less than 40%, less than 30%, less than 25%, less than 20%, less than 15%, less than 12%, less than 10%, less than 7%, less than 5%, less than 3%, less than 1% over time period assayed. In some embodiments, the polydispersity index (PdI) of the nanoparticle increases less than 50%, less than 40%, less than 30%, less than 25%, less than 20%, less than 15%, less than 12%, less than 10%, less than 7%, less than 5% less than 3%, less than 1% over time period assayed.

In some embodiments, the nanoalum particle is stable at 0-8° C. In some embodiments, the nanoalum particle is stable at 0° C., 1° C., 2° C., 3° C., 4° C., 5° C., 6° C., 7° C., or 8° C. for at least 1 minute, for at least 5 minutes, for at least 10 minutes, for at least 15 minutes, for at least 20 minutes, for at least 25 minutes, for at least 30 minutes, for at least 35 minutes, for at least 40 minutes, for at least 45 minutes, for at least 50 minutes, for at least 55 minutes, for at least 1 hour, for at least 2 hours, for at least 6 hours, for at least 12 hours, for at least 18 hours, for at least 24 hours, for at least 48 hours, for at least 72 hours, for at least 1 week, for at least 2 weeks, for at least 3 weeks, for at least 1 month, for at least 2 months, for at least 3 months, for at least 4 months, for at least 5 months, for at least 6 months, for at least 7 months, for at least 8 months, for at least 9 months, for at least 10 months, for at least 11 months, for at least 1 year, for at least 2 years, or for at least 5 years.

In some embodiments, the nanoalum particle is stable at 20-30° C. In some embodiments, the nanoalum particle is stable at 25° C. for at least 1 minute, for at least 5 minutes, for at least 10 minutes, for at least 15 minutes, for at least 20 minutes, for at least 25 minutes, for at least 30 minutes, for at least 35 minutes, for at least 40 minutes, for at least 45 minutes, for at least 50 minutes, for at least 55 minutes, for at least 1 hour, for at least 2 hours, for at least 6 hours, for at least 12 hours, for at least 18 hours, for at least 24 hours, for at least 48 hours, for at least 72 hours, for at least 1 week, for at least 2 weeks, for at least 3 weeks, for at least 1 month, for at least 2 months, for at least 3 months, for at least 4 months, for at least 5 months, for at least 6 months, for at least 7 months, for at least 8 months, for at least 9 months, for at least 10 months, for at least 11 months, for at least 1 year, for at least 2 years, or for at least 5 years.

In some embodiments, the nanoalum particle is stable at 35-40° C. In some embodiments, the nanoalum particle is stable at 35° C., 36° C., 37° C., 38° C., 39° C., or 40° C. for at least 1 minute, for at least 5 minutes, for at least 10 minutes, for at least 15 minutes, for at least 20 minutes, for at least 25 minutes, for at least 30 minutes, for at least 35 minutes, for at least 40 minutes, for at least 45 minutes, for at least 50 minutes, for at least 55 minutes, for at least 1 hour, for at least 2 hours, for at least 6 hours, for at least 12 hours, for at least 18 hours, for at least 24 hours, for at least 48 hours, for at least 72 hours, for at least 1 week, for at least 2 weeks, for at least 3 weeks, for at least 1 month, for at least 2 months, for at least 3 months, for at least 4 months, for at least 5 months, for at least 6 months, for at least 7 months, for at least 8 months, for at least 9 months, for at least 10 months, for at least 11 months, for at least 1 year, for at least 2 years, or for at least 5 years.

In some embodiments, the nanoalum particle is stable at 57-62° C. In some embodiments, the nanoalum particle is stable at 57° C., 58° C., 59° C., 60° C., 61° C., or 62° C. for at least 1 minute, for at least 5 minutes, for at least 10 minutes, for at least 15 minutes, for at least 20 minutes, for at least 25 minutes, for at least 30 minutes, for at least 35 minutes, for at least 40 minutes, for at least 45 minutes, for at least 50 minutes, for at least 55 minutes, for at least 1 hour, for at least 2 hours, for at least 6 hours, for at least 12 hours, for at least 18 hours, for at least 24 hours, for at least 48 hours, for at least 72 hours, for at least 1 week, for at least 2 weeks, for at least 3 weeks, for at least 1 month.

In one exemplary embodiment, the nanoalum particle is stable at 4° C. for at least 2 years. In one exemplary embodiment, the nanoalum particle is stable at 4° C. for at least 4 years. In one exemplary embodiment, the nanoalum particle is stable at 4° C. for at least 5 years. In one exemplary embodiment, the nanoalum particle is stable at 25° C. for at least one month. In one exemplary embodiment, the nanoalum particle is stable at 37° C. for at least two weeks. In one exemplary embodiment, the nanoalum particle is stable at 60° C. for at least two weeks.

In some embodiments, the nanoalum particle is stable after 1-4 freeze thaws. In some embodiments, the nanoalum particle is stable after 1, after 2, after 3, or after 4 freeze thaws.

IV. Nanoalum Particle Compositions

Provided herein are compositions comprising nanoalum panicles, wherein the nanoalum particles comprise an aluminum salt and a sizing agent, and wherein the size of the nanoalum panicles are about 1 nm-450 nm in size. In some embodiments the average size of the nanoalum composition ranges from about 50 nm to 75 nm. In some embodiments the average size of the nanoalum composition ranges from about 50 nm to 100 nm. In some embodiments the average size of the nanoalum composition ranges from about 50 nm to 150 nm. In some embodiments the average size of the nanoalum composition ranges from about 50 nm to 200 nm. In some embodiments the average size of the nanoalum composition ranges from about 50 nm to 300 nm. In some embodiments the average size of the nanoalum composition ranges from about 50 nm to 400 nm. In some embodiments the average size of the nanoalum composition ranges from about 50 nm to 450 nm. In some embodiments the average size of the nanoalum composition ranges from about 20 nm to 100 nm. In some embodiments the average size of the nanoalum composition ranges from about 20 nm to 50 nm. In some embodiments the average size of the nanoalum composition ranges from about 10 nm to 200 nm. In some embodiments the average size of the nanoalum composition ranges from about 10 nm to 100 nm. In some embodiments the average size of the nanoalum composition ranges from about 10 nm to 50 nm. In some embodiments the average size of the nanoalum composition is about 1 nm, is about 5 nm, is about 10 nm, is about 15 nm, is about 20 nm, is about 25 nm, is about 30 nm, is about 35 nm, is about 40 nm, is about 45 nm, is about 50 nm, is about 55 nm, is about 60 nm, is about 65 nm, is about 70 nm, is about 75 nm, is about 80 nm, is about 85 nm, is about 90 nm, is about 95 nm, is about 100 nm, is about 105 nm, is about 10 nm, is about 115 nm, is about 120 nm, is about 125 nm, is about 130 nm, is about 135 nm, is about 140 nm, is about 145 nm, is about 150 nm, is about 155 nm, is about 160 nm, is about 165 nm, is about 170 nm, is about 175 nm, is about 180 nm, is about 185 nm, is about 190 nm, is about 195 nm, is about 200 nm, is about 210 nm, is about 220 nm, is about 240 nm, is about 250 nm, is about 260 nm, is about 280 nm, is about 200 nm, is about 300 nm, is about 320 nm, is about 340 nm, is about 350 nm, is about 360 nm, is about 380 nm, is about 400 nm, is about 420 nm, is about 440 nm, or is about 450 nm. In some embodiments, the average size of the nanoalum composition is no greater than about 1 nm, no greater than about 5 nm, no greater than about 10 nm, no greater than about 15 nm, no greater than about 20 nm, no greater than about 25 nm, no greater than about 30 nm, no greater than about 33 nm, no greater than about 40 nm, no greater than about 45 nm, no greater than about 50 nm, no greater than about 55 nm, no greater than about 60 nm, no greater than about 65 nm, no greater than about 70 nm, no greater than about 75 nm, no greater than about 80 nm, no greater than about 85 nm, no greater than about 90 nm, no greater than about 95 nm, no greater than about 100 nm, no greater than about 105 nm, no greater than about 10 nm, no greater than about 115 nm, no greater than about 120 nm, no greater than about 125 nm, no greater than about 130 nm, no greater than about 135 nm, no greater than about 140 nm, no greater than about 145 nm, no greater than about 150 nm, no greater than about 155 nm, no greater than about 160 nm, no greater than about 165 nm, no greater than about 170 nm, no greater than about 175 nm, no greater than about 180 nm, no greater than about 185 nm, no greater than about 190 nm, no greater than about 195 nm, no greater than about 199 nm, no greater than about 210 nm, no greater than about 230 nm, no greater than about 250 nm, no greater than about 270 nm, no greater than about 290 nm, no greater than about 310 nm, no greater than about 330 nm, no greater than about 350 nm, no greater than about 370 nm, no greater than about 390 nm, no greater than about 410 nm, no greater than about 430 nm, no greater than about 440 nm, or no greater than about 449 nm as measured by DLS.

In some embodiments, the compositions are filterable and terminally sterilizable prior to vialing. In some embodiments, the composition is capable of being filtered through a 0.45 micron filter. In some embodiments, the composition is capable of being filtered through a 0.20 micron filter. In some embodiments, the composition is capable of being filtered through a 0.22 micron filter.

In some embodiments, the compositions are maintained as aqueous formulations. In some embodiments, the compositions are maintained as lyophilized formulations. In some embodiments, the compositions are maintained as spray-dried formulations.

In some embodiments, the composition comprises a nanoalum and an emulsion. In some embodiments the emulsion of the composition is a water in oil emulsion. In some embodiments the emulsion of the composition is a picketing emulsion. In some embodiments the emulsion of the composition is an oil-in-water emulsion. In some embodiments the oil of the emulsion is a biodegradable oil. In further embodiments the oils is a squalene. In other embodiment the oil is a synthetic biodegradable oil.

Liposomes and liposome derived nanovesicles known in the art [8] and may be used with the nanoalums of the present disclosure. In some embodiments, the composition comprises a liposome containing the nanoalum particles. In some embodiments the composition comprises a nanoalum and a liposome wherein the liposome is a cationic liposome. In some embodiments the composition comprises a nanoalum and a liposome wherein the liposome is an anionic liposome. In some embodiments the composition comprises a nanoalum and a liposome wherein the liposome is a neutral liposome. In some embodiments the composition comprises a nanoalum and a liposome wherein the liposome is an archaeosome. In some embodiments the composition comprises a nanoalum and a liposome wherein the liposome is virosome.

A. Bioactive Agents

In some embodiments, the composition further comprises one or more bioactive agents, for example the bioactive agent can be a polypeptide, a polynucleotide, an antigen, an adjuvant, a diagnostic agent, a therapeutic agent, an organism, a virus, a viral genome. In some embodiments, the composition comprises two or more bioactive agents. In some embodiments, the bioactive agent is associated with the nanoalum particle. In some embodiments, the bioactive agent is associated with the nanoalum particle by ligand exchange and/or by an electrostatic (charge-based) interaction. In some embodiments, at least 25%, at least 40%, at least 50%, at least 65%, at least 70%, at least 75%, at least 80%, at least 85%, at least 90%, at least 95%, at least 97%, at least 99%, of the bioactive agent present in the composition is associated with nanoalum particles. In some embodiments, the percent association of the bioactive agent with the nanoalum particle is determined by gel electrophoresis or UV spectroscopy. One exemplary method of determining the percent association is demonstrated in the examples.

i. Macromolecules

In some embodiments, the bioactive agent is a macromolecule. A macromolecule can include, but is not limited to, a polynucleotide, a polypeptide, or an antigen. In some embodiments, the macromolecule is naturally occurring. In some embodiments, the macromolecule is synthetic. In some embodiments, the macromolecule is labeled or tagged.

a. Polynucleotides

Proteins, protein subunits and inactivated pathogen are efficient stimulators of antibody responses (humoral immunity) and have been successfully developed as successful vaccines for a number of infectious diseases where humoral immunity is a strong correlate of protection. However for some chronic infectious diseases or cancer, in addition to a humoral response, a classic cellular or cytolytic T cell response may be required. Classically generation of cellular immune responses occurs from endogenous or intracellular presentation of antigens in the context of major histocompatibility molecules. This has led researchers to theorize that the delivery of nucleic acids to encode intracellular antigens may lead to more successful vaccination strategies for chronic infection and cancer. RNA vaccines are particularly attractive for nucleic acid delivery based, theoretically, on the ability of the protein transcribed by the RNA to be more efficiently presented in the context of the major histocompatibility molecules of the host. Delivery of RNA vaccines in the art include, for example, delivery of messenger RNA and replicating RNA constructs expressed from alphavirus constructs, both of which rely on delivery and expression of the RNA encoded protein in the cell. As promising as this approach seems in theory, to date in practice, the development of RNA vaccines has been limited by the cost of producing RNA, the relative inefficient delivery of RNA in vivo, the instability of naked RNA, and the relative in vivo level of expression of the RNA. Simply, all these limitations may be attributed to the lack of efficient delivery of RNA in vivo. Recently numerous strategies have been employed to address these limitations including incorporation of chemically modified nucleotides, modification of the RNA structure including ARCA cap and elongated poly(A) tails, and evaluation of delivery strategies for the RNA ranging from naked RNA to cationic lipids and polymeric delivery vehicles (1-5). Perhaps the most well studied formulations for delivery of RNA are the cationic emulsions comprised of the cationic lipid, DOTAP, DOTAP, sorbitan trioleate, polysorbate and squalene (5). It has been demonstrated that these cationic liposomes self-assemble into synthetic lipid nanoparticles with the RNA encapsulated in the core of the particle. While these cationic liposomes have demonstrated the ability to deliver RNA vaccines and induce immune responses, the manufacture of these formulations is rather complex and expensive. What is needed in the art is a stable, inexpensive and amenable to large scale manufacture including terminal sterilization formulation for delivery of polynucleotides including RNA and DNA.

In some embodiments the bioactive agent is a polynucleotide. A polynucleotide includes, but is not limited to a DNA, an RNA, an aptamer, and an oligonucleotide. In some embodiments the polynucleotide is DNA. In some embodiments the polynucleotide is RNA. In some embodiments, the DNA or RNA is single stranded or double stranded. In some embodiments the polynucleotide is a non-coding RNA. In some embodiments the polynucleotide is a coding RNA. In some embodiments the RNA is selected from the group consisting of replicon RNA, mRNA, tRNA, si RNA, shRNA, Rig I and microRNA.

In some embodiments, the polynucleotide encodes a polypeptide. In some embodiments, the polynucleotide encodes a polypeptide that is an antigen or comprises an antigen as further described below. In some embodiments, the polypeptide encoded by the polynucleotide is a fusion protein. In some embodiments, the polypeptide encoded by the polynucleotide is ID93.

In one specific embodiment, the nanoparticle comprises a PEG sizing agent, and the agent is an RNA.

In one specific embodiment, the nanoparticle comprises a PAA sizing agent, and the agent is an RNA.

1. Recombinant Expression Constructs

According to certain herein disclosed embodiments, the compositions described herein may contain at least one recombinant expression construct which comprises a promoter operably linked to a nucleic acid sequence encoding a polypeptide. In certain further embodiments the recombinant expression construct is present in a viral vector, such as an adenovirus, adeno-associated virus, herpesvirus, lentivirus, poxvirus or retrovirus vector. Compositions and methods for making and using such expression constructs and vectors are known in the art, for the expression of polypeptide antigens as provided herein, for example, according to Ausubel et a). (Eds.), Current Protocols in Molecular Biology, 2006 John Wiley & Sons, NY. Non-limiting examples of recombinant expression constructs generally can be found, for instance, in U.S. Pat. Nos. 6,844,192; 7,037,712; 7,052,904; 7,001,770; 6,106,824; 5,693,531; 6,613,892; 6,875,610, 7,067,310; 6,218,186; 6,783,981; 7,052,904; 6,783,981; 6,734,172; 6,713,068; 5,795,577 and 6,770,445 and elsewhere, with teachings that can be adapted to the expression of polypeptide antigens as provided herein, for use in certain presently disclosed embodiments.

2. Alternate Internucleoside Linkage and Nucleic Acid Analogs

In some embodiments the polynucleotides comprise alternate internucleoside linkages or nucleic acid analogs. For example, in one embodiment, the polynucleotide comprises phosphorodithioate, or a phosphorothioate bonds, although phosphodiester and other internucleotide bonds are within the scope of the present disclosure including oligonucleotides with mixed internucleotide linkages. Methods for producing phosphorothioate oligonucleotides or phosphorodithioate are described in U.S. Pat. Nos. 5,666,153, 5,278,302 and WO95/26204.

3. Replicons

In some embodiments, the polynucleotide is a replicon. In some embodiments, the replicon is a plasmid, cosmid, bacmid, phage or virus that is capable of replication largely under its own control. In some embodiments, the replicon is RNA or DNA. In some embodiments, the replicon is single or double stranded. In some embodiments, the replicon is derived from an RNA virus.

b. Polypeptides

In some embodiments the bioactive agent is a polypeptide. Thus in these embodiments, the compositions described comprise the nanoalum particles provided herein, and further comprise a polypeptide. In some embodiments the polypeptide is a full length protein or a fragment thereof. In some embodiments the polypeptide is a peptide. In some embodiments, the polypeptide is a fusion protein. In some particular embodiments, the fusion protein is capable of eliciting an immune response upon administration to an individual. In some embodiments, the polypeptide is an antigen, as further described below.

c. Antigens

In some embodiments the bioactive agent is an antigen. In some embodiments the antigen is a polypeptide encoded by a polynucleotide. In some embodiments the antigen is a polypeptide encoded by a polynucleotide. In some embodiments the antigen is a DNA polynucleotide delivered the nanoalum formulations of the present disclosure that encodes a polypeptide. In some embodiments the antigen is an RNA polynucleotide delivered the nanoalum formulations of the present disclosure that encodes the polypeptide. Thus in some embodiments, the compositions described comprise any one of the nanoalum particles provided herein, and further comprise an antigen wherein the antigen of the nanoalum particle is provided as a polypeptide or polynucleotide.

In some embodiments the antigen is involved in, or derived from, an allergy, cancer, or infectious disease.

In some embodiments the compositions described herein are useful for vaccination purposes, and are provided as vaccine formulations (vaccine compositions).

An antigen may be any target epitope, molecule (including a biomolecule), molecular complex (including molecular complexes that contain biomolecules), subcellular assembly, cell or tissue against which elicitation or enhancement of immunoreactivity in a subject is desired. Frequently, the term antigen will refer to a polypeptide antigen of interest. However, antigen, as used herein, may also refer to a recombinant construct which encodes a polypeptide antigen of interest (e.g., an expression construct). In certain embodiments the antigen may be, or may be derived from, or may be immunologically cross-reactive with, an infectious pathogen and/or an epitope, biomolecule, cell or tissue that is associated with infection, cancer, autoimmune disease, allergy, asthma, or any other condition where stimulation of an antigen-specific immune response would be desirable or beneficial.

Accordingly, certain embodiments contemplate an antigen that is derived from at least one infectious pathogen such as a bacterium, a virus or a fungus, including an Actinobacterium such as *M. tuberculosis* or *M. leprae* or another *mycobacterium*, a bacterium such as a member of the genus *Salmonella, Neisseria, Borrelia, Chlamydia* or *Bordetella*; a virus such as a herpes simplex virus, a human immunodeficiency virus (HIV), a feline immunodeficiency virus (FIV), cytomegalovirus. Varicella Zoster Virus, hepatitis virus, Epstein Barr Virus (EBV), respiratory syncytial virus, human papilloma virus (HPV) and a cytomegalovirus; HIV such as HIV-1 or HIV-2; a fungus such as *Aspergillus, Blastomyces. Coccidioides* and Pneumocysti or a yeast, including *Candida* species such as *C. albicans, C. glabrata, C. krusei, C. lusitaniae, C. tropicalis* and *C. parapsilosis*; a parasite such as a protozoan, for example, a *Plasmodium* species including *P. falciparum, P. vivax, P. malariae* and *P. ovale*; or another parasite such as one or more of *Acanthamoeba, Entamoeba histolytica. Angiostrongylus, Schistosoma mansonii, Schistosoma haematobium, Schistosoma japonicum, Cryptosporidium, Ancylostoma, Entamoeba histolytica. Entamoeba coli. Entamoeba dispar. Entamoeba hartmanni, Entamoeba polecki, Wucherena bancrofti, Giardia*, and *Leishmania*.

For example, in certain embodiments, antigens are derived from *Borrelia* sp., the antigens may include nucleic acid, pathogen derived antigen or antigenic preparations, recombinantly produced protein or peptides, and chimeric fusion proteins. One such antigen is OspA. The OspA may be a full mature protein in a lipidated form by virtue of its biosynthesis in a host cell (Lipo-OspA) or may alternatively be a non-lipidated derivative. Such non-lipidated derivatives include the non-lipidated NS1-OspA fusion protein which has the first 81 N-terminal amino acids of the non-structural protein (NS1) of the influenza virus, and the complete OspA protein, and another, MDP-OspA is a non-lipidated form of OspA carrying 3 additional N-terminal amino acids.

In certain embodiments the antigen is derived from a virus such as from HIV-1, (such as tat, nef, gp120 or gp160), human herpes viruses, such as gD or derivatives thereof or Immediate Early protein such as ICP27 from HSV1 or HSV2, cytomegalovirus ((esp. Human)(such as gB or derivatives thereof), Rotavirus (including live-attenuated viruses), Epstein Barr virus (such as gp350 or derivatives thereof). Varicella Zoster Virus (such as gpl, II and IE63), or from a hepatitis virus such as hepatitis B virus (for example Hepatitis B Surface antigen or a derivative thereof), hepatitis A virus, hepatitis C virus and hepatitis E virus, or from other viral pathogens, such as paramyxoviruses: Respiratory Syncytial virus (such as F and G proteins or derivatives thereof), parainfluenza virus, measles virus, mumps virus, human papilloma viruses (for example HPV6, 11, 16, 18, etc.), flaviviruses (e.g., yellow fever virus, dengue virus, tick-borne encephalitis virus, Japanese encephalitis virus. West Nile virus, Zika virus, Powassan virus) or influenza virus (whole live or inactivated virus, split influenza virus, grown in eggs or MDCK cells, or whole flu virosomes (as described by Gluck, Vaccine, 1992, 10, 915-920) or purified or recombinant proteins thereof, such as HA, NP, NA, or M proteins, or combinations thereof).

In certain other embodiments, the antigen is derived from one or more bacterial pathogens such as *Neisseria* spp, including N. gonorrhea and *N. meningitidis* (for example capsular polysaccharides and conjugates thereof, transferrin-binding proteins, lactoferrin binding proteins, PilC, adhesins); *S. pyogenes* (for example M proteins or fragments thereof, C5A protease, lipoteichoic acids), *S. agalactiae, S. mutans: H. ducreyi; Moraxella* spp, including *M. catarrhalis*, also known as *Branhamella catarrhal* is (for example high and low molecular weight adhesins and invasins); *Bordetella* spp, including *B. pertussis* (for example pertactin, pertussis toxin or derivatives thereof, filamentous hemagglutinin, adenylate cyclase, fimbriae), *B. parapertussis* and *B. bronchiseptica; Mycobacterium* spp., including *M. tuberculosis* (for example ESAT6, Antigen 85A, -B or -C), *M. bovis, M. leprae, M. avium, M. paratuberculosis, M. smegmatis; Legionella* spp, including *L. pneumophila; Escherichia* spp, including enterotoxic *E. coli* (for example colonization factors, heat-labile toxin or derivatives thereof, heat-stable toxin or derivatives thereof), enterohemorragic *E. coli*, enteropathogenic *E. coli* (for example shiga toxin-like toxin or derivatives thereof); *Vibrio* spp, including *V. cholera* (for example cholera toxin or derivatives thereof); *Shigella* spp, including *S. sonnei, S. dysenteriae, S. flexnerii; Yersinia* spp, including *Y. enterocolitica* (for example a Yop protein), *Y. pestis, Y. pseudotuberculosis; Campylobacter* spp, including *C. jejuni* (for example toxins, adhesins and invasins) and *C. coli; Salmonella* spp, including *S. typhi, S. paratyphi. S. choleraesuis, S. enteritidis; Listeria* spp, including *L. monocytogenes, Helicobacter* spp, including *H. pylori* (for example urease, catalase, vacuolating toxin), *Pseudomonas* spp, including *P. aeruginosa; Staphylococcus* spp., including *S. aureus, S. epidermidis; Enterococcus* spp., including *E. faecalis, E. faecium; Clostridium* spp., including *C. tetani* (for example tetanus toxin and derivative thereof), *C. botulinum* (for example botulinum toxin and derivative thereof); *C. difficile* (for example *Clostridium* toxins A or B and derivatives thereof); *Bacillus* spp., including *B. anthracis* for example botulinum toxin and derivatives thereof), *Corynebacterium* spp., including *C. diphtheriae* (for example diphtheria toxin and derivatives thereof); *Borrelia* spp., including *C. B. burgdorferi* (for example OspA, OspC, DbpA, DbpB), *B. garinii* (for example OspA, OspC, DbpA, DbpBX B. afzelii* (for example OspA, OspC, DbpA, DbpB), *B. andersonii* (for example OspA, OspC, DbpA, DbpB), *B. hermsii; Ehrlichia* spp., including *E. equi* and the agent of the Human Granulocytic Ehrlichiosis; *Rickettsia* spp, including *R. rickettsii; Chlamydia* spp. including *C. trachomatis* (for example MOMP, heparin-binding proteins), *C. pneumoniae* (for example MOMP, heparin-binding proteins), *C. psittaci; Leptospira* spp., including *L. interrogans; Treponema* spp., including *T. pallidum* (for example the rare outer membrane proteins), *T. denticola, T. hyodysenteriae*; or other bacterial pathogens.

In certain other embodiments, the antigen is derived from one or more parasites (See, e.g., John, D. T. and Petri, W. A., Markell and Voge's Medical Parasitdogy—9th Ed., 2006, WB Saunders, Philadelphia; Bowman, D. D., Georgis' Parasitology for Veterinarians-8th Ed., 2002, WB Saunders, Philadelphia) such as *Plasmodium* spp., including *P. falciparum; Toxoplasma* spp, including *T. gondii* (for example SAG2, SAG3, Tg34); *Entamoeba* spp., including *E. histolytica; Babesia* spp., including *B. microti; Trypanosoma* spp., including *T. cruzi, Giardia* spp, including *G. lamblia; Leshmania* spp., including *L. major, Pneumocystis* spp., including *P. carinii; Trichomonas* spp., including *T. vaginalis*; or from a helminth capable of infecting a mammal, such as: (i) nematode infections (including, but not limited to, *Enterobius vermicularis, Ascaris lumbricoides, Trichuris trichiura, Necator americanus, Ancylostoma duodenale, Wuchereria bancrofti, Brugia malayi, Onchocerca volvulus. Dracanculus medinensis, Trichinella spiralis*, and *Strongyloides stercoralis*); (ii) trematode infections (including, but not limited to, *Schistosoma mansoni. Schistosoma haematobium. Schistosoma japonicum, Schistosoma mekongi, Opisthorchis sinensis. Paragonimus* sp, *Fasciola hepatica. Fasciola magna. Fasciola gigantica*); and (iii) cestode infections (including, but not limited to, *Taenia saginata* and *Taenia solium*). In certain embodiments, the antigen is derived from *Schisostoma* spp., *Schistosoma mansonii, Schistosoma haematobium*, and/or *Schistosoma japonicum*, or derived from yeast such as *Candida* spp., including *C. albicans; Cryptococcus* spp., including *C. neoformans*.

Other specific antigens are derived from *M. tuberculosis*, for example Th Ra12, Tb H9, Tb Ra35, Tb38-1, Erd 14, DPV, MTL MSL, mTTC2 and hTCC1 (WO 99/51748). Proteins for *M. tuberculosis* also include fusion proteins and variants thereof where at least two, three, or four or more, polypeptides of *M. tuberculosis* are fused into a larger protein. Certain fusions include Ra12-TbH9-Ra35, Erd14-DPV-MTI, DPV-MTI-MSL, Erd14DPV-MTI-MSL-mTCC2, Erd14-DPV-MTI-MSL, DPV-MTI-MSL-mTCC2, TbH9-DPV-MTI (WO 99151748). Other antigens that may be used include antigens, combination of antigens, and fusion proteins described in US 2010/0129391 and WO 2008/124647 In one exemplary embodiment, the fusion protein is ID93. In one exemplary embodiment, the fusion protein is ID91.

Other specific antigens are derived from *Leishmania*, for example *Leishmania* polypeptides and polynucleotides of the present disclosure may be prepared or isolated using any of a variety of procedures and using any of a variety of *Leishmania* species including, but not limited to, *L. donovani, L. chagasi, L. infantum, L. major, L. amazonensis, L. braziliensis, L. panamensis, L. mexicana, L. tropics*, and *L. guyanensis*. Such species are available, for example, from the American Type Culture Collection (ATCC), Rockville, MD. Proteins for *Leishmania* also include fusion proteins and variants thereof where at least two, three, or four or more, polypeptides of *Leishmania* are fused into a larger protein as described in WO2009/012166, WO 2014/160987, WO 2014/160985, In one exemplary embodiment, the fusion protein is EMCH as described herein.

Other specific antigens are derived from *Chlamydia*, and include for example the High Molecular Weight Protein (HWMP) (WO 99/17741), ORF3 (EP 366 412), and putative membrane proteins (Pmps). Other *Chlamydia* antigens can be selected from the group described in WO 99128475. Certain antigens may be derived from *Streptococcus* spp, including *S. pneumoniae* (for example capsular polysaccharides and conjugates thereof, PsaA, PspA, streptolysin, choline-binding proteins) and the protein antigen Pneumolysin (Biochem Biophys Acta, 1989, 67, 1007; Rubins et al., Microbial Pathogenesis, 25, 337-342), and mutant detoxified derivatives thereof (WO 90/06951; WO 99/03884). Other bacterial vaccines comprise antigens derived from *Haemophilus* spp., including *H. influenzae* type B (for example PRP and conjugates thereof), non typeable *H. influenzae*, for example OMP26, high molecular weight adhesins, P5, P6, protein D and lipoprotein D, and fimbrin and fimbrin derived peptides (U.S. Pat. No. 5,843,464) or multiple copy variants or fusion proteins thereof.

Other specific antigens fare derived from Hepatitis B. Derivatives of Hepatitis B Surface antigen are well known in the art and include, inter alia, those PreS1, Pars2 S antigens set forth described in European Patent applications EP-A414 374; EP-A-0304 578, and EP 198474. In one aspect antigen is HIV-1 gp120, especially when expressed in CHO cells. In a further embodiment, the antigen is gD2t.

In other embodiments, the antigen is derived from the Human Papilloma Virus (HPV) considered to be responsible for genital warts (HPV 6 or HPV 11 and others), and the HPV viruses responsible for cervical cancer (HPV 16, HPV18 and others). Particular antigens include L1 particles or capsomers, and fusion proteins comprising one or more antigens selected from the HPV 6 and HPV 11 proteins E6, E7, L1, and L2. Certain forms of fusion protein include L2E7 as disclosed in WO 96/26277, and proteinD(1/3)-E7 disclosed in OB 9717953.5 (PCT/EP98/05285). Additional possible antigens include HPV 16 or 18 antigens. For example, L1 or L2 antigen monomers, or L1 or L2 antigens presented together as a virus like particle (VLP) or the L1 alone protein presented alone in a VLP or capsomer structure. Such antigens, virus like particles and capsomer are per se known. See for example WO94/00152, WO94/20137, WO94/05792, and WO93/02184.

In other embodiments, the antigen is a fusion protein. Fusion proteins may be included alone or as fusion proteins such as E7, E2 or F5 for example; particular embodiments include a VLP comprising L1E7 fusion proteins (WO 96/11272). Particular HPV 16 antigens comprise the early proteins E6 or F7 in fusion with a protein D carrier to form Protein D-E6 or E7 fusions from HPV 16, or combinations thereof; or combinations of E6 or E7 with L2 (WO 96/26277). Alternatively the HPV 16 or 18 early proteins E6 and E7, may be presented in a single molecule, for example a Protein D-E6/E7 fusion. Compositions may optionally contain either or both E6 and E7 proteins front HPV 18, for example in the form of a Protein D-E6 or Protein D-E7 fusion protein or Protein D E6/E7 fusion protein. Compositions may additionally comprise antigens from other HPV strains, for example from strains HPV 31 or 33.

Antigens may also be derived from parasites that cause Malaria. For example, antigens from *Plasmodia falciparum* include RTS,S and TRAP. RTS is a hybrid protein comprising substantially all the C-terminal portion of the circumsporozoite (CS) protein of *P. falciparum* linked via four amino acids of the preS2 portion of Hepatitis B surface antigen to the surface (S) antigen of hepatitis B virus Its full structure is disclosed in the International Patent Application No. PCT/EP92/02591, published as WO 93/10152 claiming priority from UK patent application No. 9124390.7. When expressed in yeast RTS is produced as a lipoprotein particle, and when it is co-expressed with the S antigen from HBV it produces a mixed particle known as RTS,S.

TRAP antigens are described in the International Patent Application No. PCT/GB89/00895 published as WO 90/01496. An embodiment of the present disclosure is a Malaria vaccine wherein the antigenic preparation comprises a combination of the RTS,S and TRAP antigens. Other plasmodia antigens that are likely candidates to be components of a multistage Malaria vaccine are *P. faciparum* MSP1, AMA1, MSP3, EBA, GLURP, RAP1, RAP2, Sequestrin, PfEMP1, Pf332, LSA1, LSA3, STARP, SALSA, PfEXP1, Pfs25, Pfs28, PFS27125, Pfs16, Pfs48/45, Pfs230 and their analogues in *Plasmodium* spp.

In one embodiment, the antigen is derived from a cancer cell, as may be useful for the immunotherapeutic treatment of cancers. For example, the antigen may be a tumor rejection antigen such as those for prostate, breast, colorectal, lung, pancreatic, renal or melanoma cancers. Exemplary cancer or cancer cell-derived antigens include MAGE 1, 3 and MAGE 4 or other MAGE antigens such as those disclosed in WO99/40188, PRAME, BAGE, Lage (also known as NY Eos 1) SAGE and HAGE (WO 99/53061) or GAGE (Robbins and Kawakami, 1996 Current Opinions in Immunology 8, pps 628-636; Van den Eynde et al., International Journal of Clinical & Laboratory Research (1997 & 1998); Correale et al (1997), Journal of the National Cancer Institute 89, p. 293. These non-limiting examples of antigens are expressed in a wide range of tumor types such as melanoma, lung carcinoma, sarcoma and bladder carcinoma. See, e.g., U.S. Pat. No. 6,544,518.

Other tumor-specific antigens are include, but are not restricted to, tumor-specific or tumor-associated gangliosides such as GM2, and GM3 or conjugates thereof to earner proteins; or a self peptide hormone such as whole length Gonadotrophin hormone releasing hormone (GnRH, WO 95/20600), a short 10 amino acid long peptide, useful in the treatment of many cancers. In another embodiment prostate antigens are used, such as Prostate specific antigen (PSA), PAP, PSCA (e.g., Proc. Nat. Acad. Sci USA 95(4) 1735-1740 1998), PSMA or, in one embodiment an antigen known as Prostase. (e.g., Nelson, et al., Proc. Natl. Acad. Sci. USA (1999) 96: 3114-3119; Ferguson, et al. Proc. Natl. Acad. Sci. USA 1999. 96, 3114-3119; WO 98/12302; U.S. Pat. No. 5,955,306, WO 98/20117, U.S. Pat. Nos. 5,840,871 and 5,786,148; WO 00/04149. Other prostate specific antigens are known from WO 98/137418, and WO/004149. Another is STEAP (PNAS 96 14523 14528 7-12 1999).

Other tumor associated antigens useful in the context of the present disclosure include: Plu-1 (J Biol. Chem 274 (22) 15633-15645, 1999), HASH-1, HasH-2, Cripto (Salomon et al Bioessays 199, 21:61-70. U.S. Pat. No. 5,654,140) and Criptin (U.S. Pat. No. 5,981,215). Additionally, antigens particularly relevant for vaccines in the therapy of cancer also comprise tyrosinase and survivin.

In other embodiments, the agents used in the compositions of the present disclosure include antigens associated with respiratory diseases, such as those caused or exacerbated by bacterial infection (e.g. pneumococcal), for the prophylaxis and therapy of conditions such as chronic obstructive pulmonary disease (COPD). COPD is defined physiologically by the presence of irreversible or partially reversible airway obstruction in patients with chronic bronchitis and/or emphysema (Am J Respir Crit Care Med. 1995 November; 152(5 Pt 2):S77-121). Exacerbations of COPD are often caused by bacterial (e.g. pneumococcal) infection (Clin Microbiol Rev. 2001 April; 14(2):336-63).

ii. Adjuvants

In some embodiments the agent is an adjuvant, and thus the compositions comprising any of the nanoalum particles described herein comprise an adjuvant, either in the presence or absence of antigen.

In some embodiments, the adjuvant is selected from the group consisting of a AS-2, monophosphoryl lipid A, 3-de-O-acylated monophosphoryl lipid A, IFA, QS21, CWS, TOM, AGPs, CpG-containing oligonucleotides, Toll-like receptor (TLR) agonists, Leif, saponins, saponin mimetics, biological and synthetic lipid A, imiquimod, gardiquimod, resiquimod, polyI:C, flagellin, GLA, SLA, STING, and combinations thereof.

In one exemplary embodiment the adjuvant is GLA. In one exemplary embodiment the adjuvant is SLA.

a. TLR Agonists

As described herein, certain embodiments of the present disclosure contemplate comprising the nanoalum particles as described herein, and further include one or more toll-like receptor agonists (TLR agonist). Toll-like receptors (TLR) include cell surface transmembrane receptors of the innate immune system that confer early-phase recognition capability to host cells for a variety of conserved microbial molecular structures such as may be present in or on a large number of infectious pathogens, (e.g., Armant et al., 2002 *Genome Biol.* 3(8):reviews3011-3011. 6; Fearon et al., 1996 *Science* 272:50; Medzhitov et al., 1997 *Curr. Opin. Immunol.* 9:4; Luster 2002 *Curr. Opin. Immunol.* 14:129; Lien et al. 2003 *Nat. Immunol.* 4:1162; Medzhitov, 2001 *Nat. Rev. Immunol.* 1:135; Takeda et al., 2003 *Ann Rev Immunol.* 21:335; Takeda et al. 2005 *Int. Immunol.* 17:1; Kaisho et al., 2004 *Microbes Infect.* 6:1388, Datta et al., 2003 *J. Immunol.* 170:4102).

Induction of TLR-mediated signal transduction to potentiate the initiation of immune responses via the innate immune system may be effected by TLR agonists, which engage cell surface TLR. For example, lipopolysaccharide (LPS) may be a TLR agonist through TLR2 or TLR4 (Tsan et al., 2004 *J. Leuk Biol.* 76:514; Tsan et al., 2004 *Am. J. Physiol. Cell Phsiol.* 286:C739; Lin et al., 2005 *Shock* 24:206); poly(inosine-cytidine) (polyI:C) may be a TLR agonist through TLR3 (Salem et al., 2006 Vaccine 24:5119); CpG sequences (oligodeoxynucleotides containing unmethylated cytosine-guanosine or "CpG" dinucleotide motifs, e.g., CpG 7909, Cooper et al., 2005 *AIDS* 19:1473; CpG 10101 Bayes et al. Methods Find Exp Clin Pharmacol 27:193; Vollmer et al. Expert Opinion on Biological Therapy 5:673; Vollmer et al., 2004 Antimicrob. Agents Chemother. 48:2314; Deng et al., 2004 *J. Immunol.* 173:5148) may be TLR agonists through TLR9 (Andaloussi et al., 2006 Glia 54:526, Chen et al., 2006 *J. Immunol.* 177:2373); peptidoglycans may be TLR2 and/or TLR6 agonists (Soboll et al., 2006 Biol. Reprod. 75:131; Nakao et al., 2005 *J. Immunol.* 174:1566); 3M003 (4-amino-2-(ethoxymethyl)-α,α-dimethyl-6,7,8,9-tetrahydro-1H-imidazo[4,5-c]quinoline-1-ethanol hydrate, Mol. Wt. 318 Da from 3M Pharmaceuticals, St. Paul, MN, which is also a source of the related compounds 3M001 and 3M002; Gorden et al., 2005 *J. Immunol.* 174:1259) may be a TLR7 agonist (Johansen 2005 Clin. Exp. Allerg. 35:1591) and/or a TLR8 agonist (Johansen 2005); flagellin may be a TLR5 agonist (Feuillet et al., 2006 Proc. Nat. Acad. Sci. USA 103:12487); and hepatitis C antigens may act as TLR agonists through TLR7 and/or TLR9 (Lee et al., 2006 Proc. Nat. Acad. Sci. USA 103:1828; Horsmans et al., 2005 Hepatol. 42:724). Other TLR agonists are known (e.g., Schirmbeck et al., 2003 *J. Immunol.* 171:5198) and may be used according to certain of the presently described embodiments.

b. TLR7/8 Agonists

Provided herein are TLR7/8 agonists that can be used in the compositions described herein. As used herein, a "TLR7/8 agonist" refers to an agonist that affects its biological activities through its interaction with TLR7, TLR8, or both. Such biological activities include, but are not limited to, induction of TLR7 and/or TLR8 mediated signal transduction to potentiate the inhibition of immune responses via the innate immune system.

c. TLR4 Agonists

Provided herein are TLR4 agonists that can be used in the compositions described herein. In certain embodiments, a TLR4 agonist used in the compositions herein comprises a glucopyranosyl lipid adjuvant (GLA), such as those described in U S Patent Publication Nos. US2007/021017, US2009/045033, US2010/037466, and US 2010/0310602, the contents of which are incorporated herein by reference in their entireties.

For example, in certain embodiments, the TLR4 agonist is a synthetic GLA adjuvant having the following structure of Formula (IV):

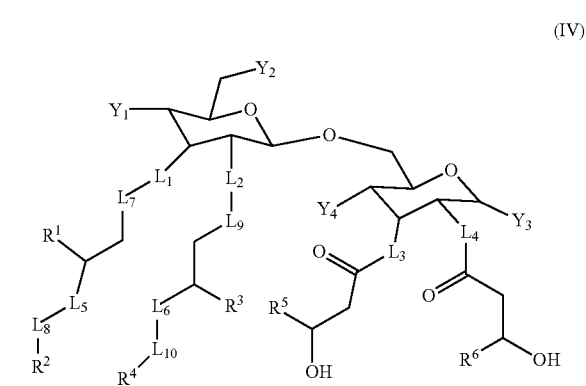

(IV)

or a pharmaceutically acceptable salt thereof, wherein:
$L_1$, $L_2$, $L_3$, $L_4$, $L_5$, and $L_6$ are the same or different and independently —O—, —NH— or —(CH$_2$)—;
$L_7$, $L_8$, $L_9$ and $L_{10}$ are the same or different and independently absent or —C(=O)—;
$Y_1$ is an acid functional group;
$Y_2$ and $Y_3$ are the same or different and independently —OH, —SH, or an acid functional group;
$Y_4$ is —OH or —SH;
$R_1$, $R_3$, $R_5$ and $R_6$ are the same or different and independently $C_{8-13}$ alkyl; and
$R_2$ and $R_4$ are the same or different and independently $C_{6-11}$ alkyl.

In some embodiments of the synthetic GLA structure, $R^1$, $R^3$, $R^5$ and $R^6$ are $C_{10}$ alkyl; and $R^2$ and $R^4$ are $C_8$ alkyl. In certain embodiments, $R^1$, $R^3$, $R^5$ and $R^6$ are $C_{11}$ alkyl; and $R^2$ and $R^4$ are $C_9$ alkyl.

For example, in certain embodiments, the TLR4 agonist is a synthetic GLA adjuvant having the following structure of Formula (V):

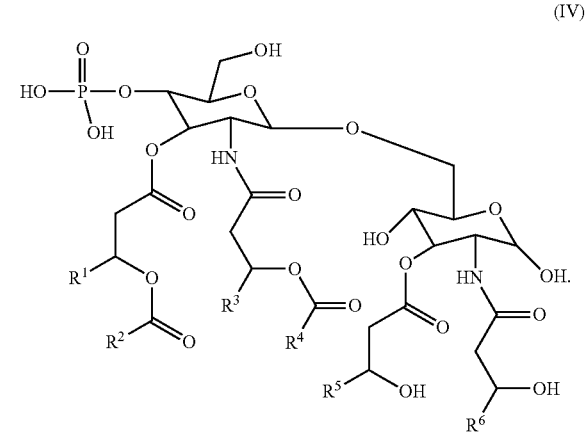

(IV)

In a specific embodiment, R1, R3, R5 and R6 are C11-C20 alkyl; and R2 and R4 are C12-C20 alkyl.

In another specific embodiment, the GLA has the formula set forth above wherein R1, R3, R5 and R6 are C11 alkyl; and R2 and R4 are C13 alkyl.

In another specific embodiment, the GLA has the formula set forth above wherein R1, R3, R5 and R6 are C10 alkyl; and R2 and R4 are C8 alkyl.

In another specific embodiment, the GLA has the formula set forth above wherein $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$, alkyl; and $R^2$ and $R^4$ are $C_9$ alkyl.

In certain embodiments, the TLR4 agonist is a synthetic GLA adjuvant having the following structure of Formula (V):

(VI)

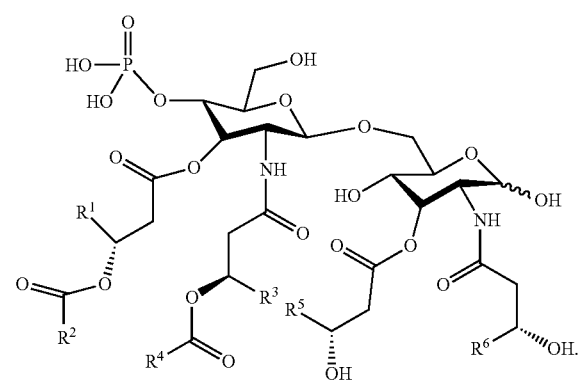

In certain embodiments of the above GLA structure, R1, R3, R5 and R6 are C11-C20 alkyl; and R2 and R4 are C9-C20 alkyl. In certain embodiments, R1, R3, R5 and R6 are C11 alkyl; and R2 and R4 are C9 alkyl.

In certain embodiments, the TLR4 agonist is a synthetic GLA adjuvant having the following structure of Formula (VI):

(VII)

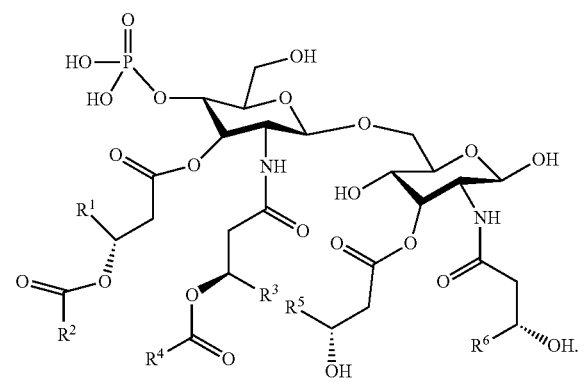

In certain embodiments of the above GLA structure, R1, R3, R5 and R6 are C11-C20 alkyl; and R2 and R4 are C9-C20 alkyl. In certain embodiments, R1, R3, R5 and R6 are C11 alkyl; and R2 and R4 are C9 alkyl.

In certain embodiments, the TLR4 agonist is a synthetic GLA adjuvant having the following structure of Formula (VII):

(VIII)

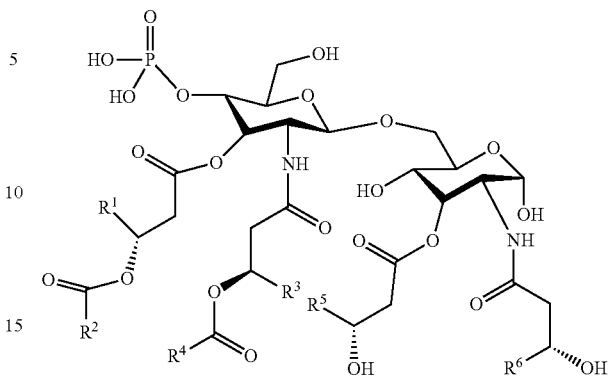

In certain embodiments of the above GLA structure, $R^1$, $R^3$, $R^5$ and $R^6$ are $C_{11}$-$C_{20}$ alkyl; and $R^2$ and $R^4$ are $C_9$-$C_{20}$ alkyl. In certain embodiments. $R^1$, $R^3$, $R^5$ and $R^6$ are $C_{11}$-$C_{20}$ alkyl; and $R^2$ and $R^4$ are $C_9$ alkyl.

In certain embodiments, the TLR4 agonist is a synthetic GLA adjuvant having the following structure (SLA):

(SLA)

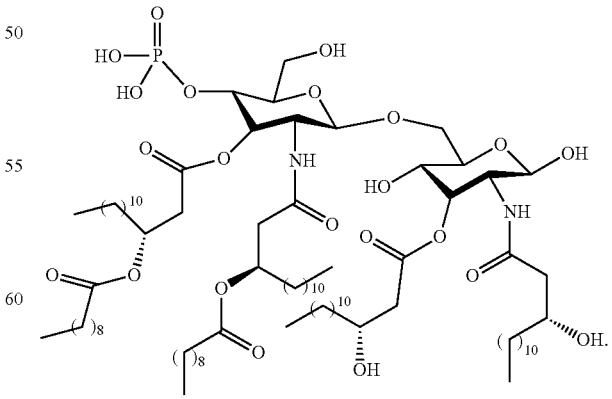

In certain embodiments, the TLR4 agonist is a synthetic GLA adjuvant having the following structure:

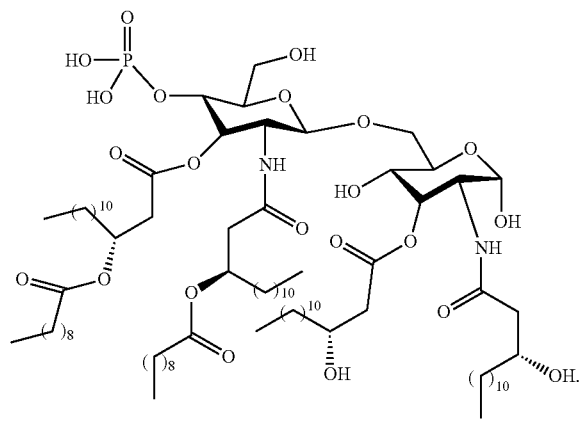

In another embodiment, an attenuated lipid A derivative (ALD) is incorporated into the compositions described herein. ALDs are lipid A-like molecules that have been altered or constructed so that the molecule displays lesser or different of the adverse effects of lipid A. These adverse effects include pyrogenicity, local Shwarzman reactivity and toxicity as evaluated in the chick embryo 50% lethal dose assay ($CELD_{50}$). ALDs useful according to the present disclosure include monophosphoryl lipid A (MLA) and 3-deacylated monophosphoryl lipid A (3D-MLA). MLA and 3D-MLA are known and need not be described in detail herein. See for example U.S. Pat. No. 4,436,727 issued Mar. 13, 1984, assigned to Ribi ImmunoChem Research, Inc., which discloses monophosphoryl lipid A and its manufacture. U.S. Pat. No. 4,912,094 and reexamination certificate B1 U.S. Pat. No. 4,912,094 to Myers, et al., also assigned to Ribi ImmunoChem Research, Inc., embodies 3-deacylated monophosphoryl lipid A and a method for its manufacture. Disclosures of each of these patents with respect to MLA and 3D-MLA are incorporated herein by reference.

In the TLR4 agonist compounds above, the overall charge can be determined according to the functional groups in the molecule. For example, a phosphate group can be negatively charged or neutral, depending on the ionization state of the phosphate group.

d. CpG Nucleotides

In one embodiment the adjuvant is an immunostimulatory oligonucleotide containing unmethylated CpG dinucleotides (e.g., U.S. Pat. No. 6,544,518). Immunostimulatory oligonucleotides containing unmethylated CpG dinucleotides ("CpG") are known as being adjuvants. In some embodiments, the CpG oligonucleotides of the present disclosure can contain two or more dinucleotide CpG motifs separated by at least three, at least four, at least five, or at least six or more nucleotides.

Examples of CpG oligonucleotides sequences are disclosed in the following publications; for certain herein disclosed embodiments the sequences can contain phosphorothioate modified internucleotide linkages:

CPG 7909: Cooper et al., "CPG 7909 adjuvant improves hepatitis B virus vaccine seroprotection in antiretroviral-treated HIV-infected adults." *AIDS*, 2005 Sep. 23; 19(14): 1473-9.

CpG 10101: Bayes et al., "Gateways to clinical trials." *Methods Find. Exp. Clin. Pharmacol.* 2005 April; 27(3):193-219.

Vollmer J., "Progress in drug development of immunostimulatory CpG oligodeoxynucleotide ligands for TLR9." Expert Opinion on Biological Therapy. 2005 May, 5(5): 673-682

Alternative CpG oligonucleotides may comprise variants of the sequences described in the above-cited publications that differ in that they have inconsequential nucleotide sequence substitutions, insertions, deletions and/or additions thereto. The CpG oligonucleotides utilized in certain embodiments of the present disclosure may be synthesized by any method known in the art (e.g., EP 468520). Conveniently, such oligonucleotides may be synthesized utilizing an automated synthesizer. The oligonucleotides are typically deoxynucleotides. In one embodiment the internucleotide bond in the oligonucleotide is phosphorodithioate, or a phosphorothioate bond, although phosphodiesters are also within the scope of the presently contemplated embodiments. Oligonucleotides comprising different internucleotide linkages are also contemplated, e.g., mixed phosphorothioate phosphodiesters. Other internucleotide bonds which stabilize the oligonucleotide may also be used.

iii. Organisms and Viruses

In some embodiments, the agent is an organism. Thus in these embodiments, the compositions described comprise the nanoalum particles provided herein, and further comprise an organism.

For example, the bacterium *Mycobacterium tuberculosis* causes tuberculosis (TB). Currently, vaccination with live bacteria is the most efficient method for inducing protective immunity against tuberculosis. The most common *Mycobacterium* employed for this purpose is *Bacillus* Calmette-Guerin (BCG), an avirulent strain of *Mycobacterium bovis*. Thus in some embodiments the composition comprises a nanoalum particle and a *Mycobacterium*.

In some embodiments the agent is a virus or a viral genome. Thus in these embodiments, the compositions described comprise the nanoalum particles provided herein, and further comprise a virus particle, isolated viral envelope or viral genome.

B. Association with the Nanoalum Particle

In the embodiments provided herein, the agents of the compositions provided herein associate with the nanoalum particle. In some embodiments the agents of the compositions provided herein bind the nanoalum particle. In some embodiments the agents of the compositions provided herein are adsorbed to the nanoalum particle. Such binding or adsorption refers to an interaction between molecules or portions thereof that exhibit mutual affinity or binding capacity, typically due to specific or non-specific binding or interaction, including, but not limited to, biochemical, physiological, and/or chemical interactions. In certain embodiments, binding to a nanoalum particle can be determined by UV spectroscopy or gel electrophoresis.

Adsorption onto nanoalum particle can take place generally, but not limited to, by the following mechanisms: electrostatic interaction and ligand exchange. Electrostatic interaction uses the presence of opposite charges on the components under a certain solution condition. Ligand exchange uses a phosphate group in one of the components to exchange with a hydroxyl group of another component. For ligand exchange, accessible phosphate groups and hydroxyl groups in the components are used. In some embodiments, to prepare a composition with an agent, antigen, or adjuvant there is consideration of the charge and presence of phosphate groups and hydroxyl groups on the agent.

i. Ligand Exchange

In certain embodiments with respect to the ligand exchange mechanism, there may be ligand exchange between the agent and the aluminum salt.

In certain embodiments, there may be ligand exchange between an adjuvant agent and the aluminum salt. Certain components in the adjuvant composition comprise phosphate groups while other certain components comprise hydroxyl groups, thus enabling ligand exchange. For example, certain TLR4 agonists comprise phosphate groups. AdjuPhos® comprises phosphate groups. Hydroxyl groups are present in at least the following components: antigens, TLR agonists, lipid/surfactant, and Alhydrogel®.

ii. Electrostatic Interaction

In certain embodiments with respect to the electrostatic interaction mechanism, there may be ligand exchange between the agent and the aluminum salt.

In certain exemplary embodiments with respect to the electrostatic interaction mechanism, a vaccine composition is substantially neutrally charged at about physiological pH. If the antigen for the vaccine composition is charged, the components for the adjuvant composition can be selected to neutralize the charge of the antigen to provide a substantially neutrally charged vaccine composition. If the antigen for the vaccine composition is substantially neutrally charged, the components for the adjuvant composition can be selected to maintain the substantially neutral charge of the antigen to provide a substantially neutrally charged vaccine composition.

As noted above, each of the components in the composition can be characterized by negatively charged, positively charged, or neutrally charged.

C. Dose Sparing

In some embodiments, a composition comprising the nanoalum particles provided herein and further comprising an agent, exhibits dose sparing and/or high levels of in vivo expression. In one embodiment, use of a composition comprising any one of the nanoalum particles provided herein allows for use of at least 5% less, at least 10% less, at least 20% less, at least 25% less, at least 30% less, at least 40% less, at least 50% less, at least 60% less, at least 75% less, at least 80% less, at least 90% less, at least 95% less or even at least 99% less of the agent, as compared to the amount of agent that would have been used to achieve the same biological and/or physiological effect, had a composition comprising any one of the nanoalum particles provided herein not been used for delivery. In one embodiment, use of a composition comprising any one of the nanoalum particles provided herein allows for use of a dose of about 1 µg, 5 µg, 2 µg, 1 µg, 10 ng, or 1 ng, of an agent to achieve the biological and/or physiological effect. In one particular embodiment, use of a composition comprising any one of the nanoalum particles provided herein allows for use of a dose of a polypeptide of about 1 µg, 5 µg, 2 µg, 1 µg, or 10 ng, 1 ng, of an agent to achieve the desired biological and/or physiological effect. In one particular embodiment, use of a composition comprising any one of the nanoalum particles provided herein allows for use of a dose of a polypeptide of about 1 µg, 5 µg. 2 µg, 1 µg, 10 ng, or 1 ng, of an agent to achieve an immune response. In one particular embodiment, use of a composition comprising any one of the nanoalum particles provided herein allows for use of a dose of a polynucleotide of about 1 µg, 5 µg, 2 µg, 1 µg, 10 ng, or 1 ng, of an agent to achieve the desired biological and/or physiological effect. In one particular embodiment, use of a composition comprising any one of the nanoalum particles provided herein allows for use of a dose of a polynucleotide of about 1 µg, 5 µg, 2 µg, 1 µg, or 10 ng, 1 ng, of an agent to achieve an immune response. In one particular embodiment, use of a composition comprising any one of the nanoalum particles provided herein allows for use of a dose of an RNA polynucleotide of about 100 ng, 50 ng, 30 ng, 10 ng, or 1 ng, of an RNA agent to achieve an immune response. In one particular embodiment, use of a composition comprising any one of the nanoalum particles provided herein allows for use of a dose of a replicon RNA vector polynucleotide of about 1 µg, 5 µg. 2 µg, 1 µg, 10 ng, or 1 ng, of an agent to achieve an immune response. In one particular embodiment, use of a composition comprising any one of the nanoalum particles provided herein allows for use of a dose of an mRNA vector polynucleotide of about 10 µg, 5 µg. 2 µg, 1 µg, 10 ng, or 1 ng, of an agent to achieve an immune response.

In one embodiment dose sparing is achieved with 300 fold less RNA needed deliver the RNA polynucleotide to achieve expression of the polypeptide antigen to generate an immune response compared to unformulated RNA. In one embodiment dose sparing is achieved with 100 fold less RNA needed deliver the RNA polynucleotide to achieve expression of the polypeptide antigen to generate an immune response compared to unformulated RNA. In one embodiment dose sparing is achieved with 50 fold less RNA needed deliver the RNA polynucleotide to achieve expression of the polypeptide antigen to generate an immune response compared to unformulated RNA. In one embodiment dose sparing is achieved with 30 fold less RNA needed deliver the RNA polynucleotide to achieve expression of the polypeptide antigen to generate an immune response compared to unformulated RNA. In one embodiment dose sparing is achieved with 10 fold less RNA needed deliver the RNA polynucleotide to achieve expression of the polypeptide antigen to generate an immune response compared to unformulated RNA.

D. Pharmaceutical Compositions

Provided herein are pharmaceutical compositions comprising the nanoalum particles and compositions described herein. In some embodiments, the composition comprising a nanoalum particle further comprises a pharmaceutically acceptable carrier, excipient or diluent. In some embodiments, the pharmaceutical composition is a vaccine composition. The compositions described herein can be administered to a subject for any therapeutic or diagnostic purpose. In some embodiment, the compositions described herein are used for stimulating an immune response in the subject (including a non-specific response and an antigen-specific response). In the embodiments provided herein, the subject is a mammal (e.g., an animal including farm animals (cows, pigs, goats, horses, etc.), pets (cats, dogs, etc.), and rodents (rats, mice, etc.), or a human). In particular, formulations and compositions of the present invention that promote a Th1 immune response can be used for stimulating such a response in a subject.

Pharmaceutical compositions generally comprise compositions described herein and may further comprise one or more components as provided herein that are selected from an antigen, additional agonists, or a recombinant expression construct, in combination with a pharmaceutically acceptable carrier, excipient or diluent.

In the embodiments provided herein, the pharmaceutical composition is capable of being filtered through a 0.45 micron filter. In some embodiments, the pharmaceutical composition is capable of being filtered through a 0.20 micron filter. In some embodiments, the pharmaceutical composition is capable of being filtered through a 0.22 micron filter.

In one embodiment, the present disclosure is drawn to a pharmaceutical composition comprising a nanoalum particle comprises a TLR7/8 agonist or a TLR4 agonist. Such a composition can be used for "monotherapy" wherein the TLR7/8 agonist or TLR 4 agonist, as described herein, is formulated in a composition and the composition is substantially devoid of other antigens, and is administered to a subject in order to stimulate an immune response, e.g., a non-specific immune response or an antigen-specific immune response, for the purpose of diagnosis, treating or preventing a disease or other condition, such as an infection by an organism.

In other embodiments, the pharmaceutical composition is a vaccine composition that comprises both compositions described herein and an antigen and may further comprise one or more components, as provided herein, in combination with a pharmaceutically acceptable carrier, excipient or diluent. Illustrative carriers will be nontoxic to recipients at the dosages and concentrations employed.

Illustrative carriers will be nontoxic to recipients at the dosages and concentrations employed.

In the embodiments provided herein, a dosage of about 1 ng/kg to about 1 mg/kg of the pharmaceutical composition is administered. In the embodiments provided herein, a dosage of about 1 ng to about 1 mg of the pharmaceutical composition is administered. In some embodiments, a dosage of about 500 µg, 200 µg, 100 µg, 50 µg, 25 µg, 20 µg, 15 µg, 10 µg, 5 µg, 2 µg, 1 µg, 10 ng, or 1 ng of the pharmaceutical composition is administered. It will be evident to those skilled in the art that the number and frequency of administration will be dependent upon the response of the subject. "Pharmaceutically acceptable carriers" for therapeutic use are well known in the pharmaceutical art, and are described, for example, in Remingtons Pharmaceutical Sciences, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. Id. at 1449. In addition, antioxidants and suspending agents may be used. Id.

"Pharmaceutically acceptable salt" refers to salts of the compounds of the present disclosure derived from the combination of such compounds and an organic or inorganic acid (acid addition salts) or an organic or inorganic base (base addition salts). The compositions of the present disclosure may be used in either the free base or salt forms, with both forms being considered as being within the scope of the present disclosure.

The pharmaceutical compositions may be in any form which allows for the composition to be administered to a patient. For example, the composition may be in the form of a solid, liquid or gas (aerosol). Typical routes of administration include, without limitation, oral, topical, parenteral (e.g., sublingually or buccally), sublingual, rectal, vaginal, and intranasal (e.g., as a spray). The term parenteral as used herein includes iontophoretic (e.g., U.S. Pat. Nos. 7,033,598; 7,018,345, 6,970,739), sonophoretic (e.g., U.S. Pat. Nos. 4,780,212; 4,767,402; 4,948,587; 5,618,275; 5,656,016; 5,722,397; 6,322,532; 6,018,678), thermal (e.g., U.S. Pat. Nos. 5,885,211; 6,685,699), passive transdermal (e.g., U.S. Pat. Nos. 3,598,122; 3,598,123; 4,286,592; 4,314,557; 4,379,454; 4,568,343; 5,464,387; UK Pat. Spec. No. 2232892; U.S. Pat. Nos. 6,871,477; 6,974,588; 6,676,961), microneedle (e.g., U.S. Pat. Nos. 6,908,453; 5,457,041; 5,591,139; 6,033,928) and jet injection administration and also subcutaneous injections, intravenous, intramuscular, intrasternal, intracavernous, intrathecal, intrameatal, intraurethral injection or infusion techniques. In a particular embodiment, a composition as described herein (including vaccine and pharmaceutical compositions) is administered intradermally by a technique selected from iontophoresis, microcavitation, sonophoresis or microneedles.

The pharmaceutical composition can be formulated so as to allow the active ingredients contained therein to be bioavailable upon administration of the composition to a subject. Compositions that will be administered to a subject take the form of one or more dosage units, where for example, a tablet may be a single dosage unit, and a container of one or more compounds of the present disclosure in aerosol form may hold a plurality of dosage units.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed.

The composition may be in the form of a liquid, e.g., an elixir, syrup, solution, emulsion or suspension. The liquid may be for oral administration or for delivery by injection, as two examples. When intended for oral administration, compositions can contain one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

A liquid pharmaceutical composition as used herein, whether in the form of a solution, suspension or other like form, may include one or more of the following carriers or excipients: sterile diluents such as water for injection, saline solution, preferably physiological saline, Ringer's solution, isotonic sodium chloride, fixed oils such as squalene, squalene, mineral oil, a mannide monooleate, cholesterol, and/or synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. An injectable pharmaceutical composition is preferably sterile.

In another embodiment, a composition of the present disclosure is formulated in a manner which can be aerosolized.

It may also be desirable to include other components in a pharmaceutical composition, such as delivery vehicles including but not limited to aluminum salts, water-in-oil emulsions, biodegradable oil vehicles, oil-in-water emulsions, biodegradable microcapsules, and liposomes. Examples of additional immunostimulatory substances (co-adjuvants) for use in such vehicles are also described above and may include N-acetylmuramyl-L-alanine-D-isoglutamine (MDP), glucan, IL-12, GM-CSF, gamma interferon and IL-12.

While any suitable carrier known to those of ordinary skill in the art may be employed in the pharmaceutical compositions of the present disclosure, the type of carrier will vary depending on the mode of administration and whether a sustained release is desired. For parenteral administration, such as subcutaneous injection, the carrier can comprise water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of the present disclosure. Suitable biodegradable microspheres are disclosed, for example, in U.S. Pat. Nos. 4,897,268 and 5,075,109 In this regard, it is preferable that the microsphere be larger than approximately 25 microns.

Pharmaceutical compositions may also contain diluents such as buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients. Neutral buffered saline or saline mixed with nonspecific serum albumin are exemplary appropriate diluents. For example, a product may be formulated as a lyophilizate using appropriate excipient solutions (e.g., sucrose) as diluents.

As described above, in certain embodiments the present disclosure includes compositions capable of delivering nucleic acid molecules encoding desired antigens. Such compositions include recombinant viral vectors (e.g., retroviruses (sec WO 90/07936, WO 91/02805, WO 93/25234, WO 93/25698, and WO 94/03622), adenovirus (see Berkner, Biotechniques 6:616-627, 1988; Li et al., Hum. Gene Ther. 4:403-409, 1993; Vincent et al., Nat. Genet. 5:130-134, 1993; and Kolls et al., Proc. Natl. Acad Sci. USA 91:215-219, 1994), pox virus (see U.S. Pat. Nos. 4,769,330; 5,017,487; and WO 89/01973)), recombinant expression construct nucleic acid molecules complexed to a polycationic molecule (see WO 93/03709), and nucleic acids associated with liposomes (see Wang et al., Proc. Natl. Acad. Sci. USA 84:7851, 1987). In certain embodiments, the DNA may be linked to killed or inactivated adenovirus (see Curiel et al., Hum. Gene Ther. 3:147-154, 1992; Cotton et al., Proc. Natl. Acad. Sci. USA 89:6094, 1992). Other suitable compositions include DNA-ligand (see Wu et al., J. Biol. Chem. 264:16985-16987, 1989) and lipid-DNA combinations (see Feigner et al., Proc. Natl. Acad. Sci. USA 84:7413-7417, 1989).

In certain embodiments a liquid composition intended for either parenteral or oral administration should contain an amount of vaccine composition such that a suitable dosage will be obtained. Typically, this amount is at least 0.01 wt % of an antigen in the composition. When intended for oral administration, this amount may be varied to be between 0.1 and about 70% of the weight of the composition. Oral compositions can contain between about 4% and about 50% of the antigen. Compositions and preparations can be prepared so that a parenteral dosage unit contains between 0.01 to 1% by weight of active composition.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the antigen (e.g., GLA-antigen vaccine composition) or GLA (e.g., immunological adjuvant composition; GLA is available from Avanti Polar Lipids, Inc., Alabaster, AL; e.g., product number 699800) of from about 0.1 to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol. In the methods of the present disclosure, the vaccine compositions/adjuvants may be administered through use of inserts), bead(s), timed-release formulation(s), patch(es) or fast-release formulation(s).

V. Uses of Nanoalum Particles and Compositions

A. Therapeutics

In some embodiments the agent is useful for therapeutic purposes. Thus in some embodiments, the compositions described comprise the nanoalum particles provided herein, and further comprise an agent for the treatment of a disease, condition, or disorder.

In some embodiments the agent is useful for the treatment or prevention of allergy, cancer, infectious disease, autoimmunity, or addiction.

The herein disclosed embodiments, compositions comprise cancer antigens. In some embodiments, a vaccine composition comprises a cancer antigen that will be useful against any cancer characterized by tumor associated antigen expression, such as HER-2/neu expression or other cancer-specific or cancer-associated antigens.

Compositions and methods according to certain embodiments of the present disclosure may also be used for the prophylaxis or therapy of autoimmune diseases, which include diseases, conditions or disorders wherein a host's or subject's immune system detrimentally mediates an immune response that is directed against "self" tissues, cells, biomolecules (e.g., peptides, polypeptides, proteins, glycoproteins, lipoproteins, proteolipids, lipids, glycolipids, nucleic acids such as RNA and DNA, oligosaccharides, polysaccharides, proteoglycans, glycosaminoglycans, or the like, and other molecular components of the subjects cells and tissues) or epitopes (e.g., specific immunologically defined recognition structures such as those recognized by an antibody variable region complementarity determining region (CDR) or by a T cell receptor CDR.

Autoimmune diseases are thus characterized by an abnormal immune response involving either cells or antibodies that are in either case directed against normal autologous tissues. Autoimmune diseases in mammals can generally be classified in one of two different categories: cell-mediated disease (i.e., T-cell) or antibody-mediated disorders. Non-limiting examples of cell-mediated autoimmune diseases include multiple sclerosis, rheumatoid arthritis, Hashimoto thyroiditis, type I diabetes mellitus (Juvenile onset diabetes) and autoimmune uveoretinitis. Antibody-mediated autoimmune disorders include, but are not limited to, myasthenia gravis, systemic lupus erythematosus (or SLE), Graves' disease, autoimmune hemolytic anemia, autoimmune thrombocytopenia, autoimmune asthma, cryoglobulinemia, thrombic thrombocytopenic purpura, primary biliary sclerosis and pernicious anemia. The antigen(s) associated with: systemic lupus erythematosus is small nuclear ribonucleic acid proteins (snRNP); Graves' disease is the thyrotropin receptor, thyroglobulin and other components of thyroid epithelial cells (Akamizu et al., 1996; Kellerman et al., 1995; Raju et al., 1997, and Texier et al., 1992); pemphigus is cadherin-like pemphigus antigens such as desmoglein 3 and other adhesion molecules (Memar et al., 1996. Stanley, 1995; Plott et al., 1994; and Hashimoto, 1993); and thrombic thrombocytopenic purpura is antigens of platelets. (See, e.g., U.S. Pat. No. 6,929,796; Gorski et al. (Eds.), Autoimmunity, 2001, Kluwer Academic Publishers, Norwell, MA; Radbruch and Lipsky, P. E. (Eds.) Current Concepts in Autoimmunity and Chronic Inflammation (Curr. Top. Microbiol, and Immunol.) 2001, Springer, NY.)

Autoimmunity plays a role in more than 80 different diseases, including type 1 diabetes, multiple sclerosis, lupus, rheumatoid arthritis, scleroderma, and thyroid diseases. Vigorous quantitative estimates of morbidity for most autoimmune diseases are lacking. Most recent studies done in the late 1990s reveal that autoimmune diseases are the third most common major illness in the United States; and the most common autoimmune diseases affect more than 8.5 million Americans. Current estimates of the prevalence of the disease range from 5 to 8 percent of the United States population. Most autoimmune diseases disproportionately affect women. Women are 2.7 times more likely than men to acquire an autoimmune disease. Women are more susceptible to autoimmune diseases; men appear to have higher levels of natural killer cell activity than do women. (Jacobsen et al, Clinical Immunology and Immunopathology, 84:223-243, 1997.)

The compositions provided herein may be used for inducing protective immunity, for example against tuberculosis include the use of polypeptides that contain at least one immunogenic portion of one or more *Mycobacterium* proteins and DNA and RNA molecules encoding such polypeptides. In addition, such compounds may be formulated into vaccines and/or pharmaceutical compositions for immunization against *Mycobacterium* infection. (U.S. Pat. Nos. 6,949,246 and 6,555,653).

In certain embodiments, the compositions of the present disclosure will be particularly applicable in treatment of the elderly and/or the immunosuppressed, including subjects on kidney dialysis, subjects on chemotherapy and/or radiation therapy, transplant recipients, and the like. Such individuals generally exhibit diminished immune responses to vaccines and therefore use of the compositions of the present disclosure can enhance the immune responses achieved in these subjects.

In other embodiments, the compositions of the present disclosure include antigens associated with respiratory diseases, such as those caused or exacerbated by bacterial infection (e.g. pneumococcal), for the prophylaxis and therapy of conditions such as chronic obstructive pulmonary disease (COPD).

In addition to direct in vivo procedures, ex vivo procedures may be used in which cells are removed from a host, modified, and placed into the same or another host animal. It will be evident that one can utilize any of the compositions noted above for introduction of antigen-encoding nucleic acid molecules into tissue cells in an ex vivo context. Protocols for viral, physical and chemical methods of uptake are well known in the art.

Accordingly, the present disclosure is useful for enhancing or eliciting, in a host, a patient or in cell culture, an immune response. As used herein, the term "subject" refers to any mammal. A patient may be afflicted with an infectious disease, cancer, such as breast cancer, or an autoimmune disease, or may be normal (i.e., free of detectable disease and/or infection) A "cell culture" is any preparation containing immunocompetent cells or isolated cells of the immune system (including, but not limited to, T cells, macrophages, monocytes, B cells and dendritic cells). Such cells may be isolated by any of a variety of techniques well known to those of ordinary skill in the art (e.g., Ficoll-hypaque density centrifugation). The cells may (but need not) have been isolated from a patient afflicted with cancer, and may be reintroduced into a patient after treatment.

B. Vaccine

The present disclosure thus provides compositions for altering (i.e., increasing or decreasing in a statistically significant manner, for example, relative to an appropriate control as will be familiar to persons skilled in the art) immune responses in a host capable of mounting an immune response. As will be known to persons having ordinary skill in the art, an immune response may be any active alteration of the immune status of a host, which may include any alteration in the structure or function of one or more tissues, organs, cells or molecules that participate in maintenance and/or regulation of host immune status. Typically, immune responses may be detected by any of a variety of well-known parameters, including but not limited to in vivo or in vitro determination of: soluble immunoglobulins or antibodies; soluble mediators such as cytokines, lymphokines, chemokines, hormones, growth factors and the like as well as other soluble small peptide, carbohydrate, nucleotide and/or lipid mediators; cellular activation state changes as determined by altered functional or structural properties of ceils of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death); or any other criterion by which the presence of an immune response may be detected.

Determination of the induction of an immune response by the compositions of the present disclosure may be established by any of a number of well-known immunological assays with which those having ordinary skill in the art will be readily familiar. Such assays include, but need not be limited to, to in vivo or in vitro determination of: soluble antibodies; soluble mediators such as cytokines, lymphokines, chemokines, hormones, growth factors and the like as well as other soluble small peptide, carbohydrate, nucleotide and/or lipid mediators; cellular activation state changes as determined by altered functional or structural properties of cells of the immune system, for example cell proliferation, altered motility, induction of specialized activities such as specific gene expression or cytolytic behavior; cellular differentiation by cells of the immune system, including altered surface antigen expression profiles or the onset of apoptosis (programmed cell death). Procedures for performing these and similar assays are widely known and may be found, for example in Lefkovits (Immunology Methods Manual: The Comprehensive Sourcebook of Techniques, 1998; see also Current Protocols in Immunology; see also, e.g., Weir, Handbook of Experimental Immunology, 1986 Blackwell Scientific, Boston, MA; Mishell and Shigii (eds.) Selected Methods in Cellular Immunology, 1979 Freeman Publishing, San Francisco, CA; Green and Reed, 1998 Science 281.1309 and references cited therein).

Detection of the proliferation of antigen-reactive T cells may be accomplished by a variety of known techniques. For example, T cell proliferation can be detected by measuring the rate of DNA synthesis, and antigen specificity can be determined by controlling the stimuli (such as, for example, a specific desired antigen- or a control antigen-pulsed antigen presenting cells) to which candidate antigen-reactive T cells are exposed T cells which have been stimulated to proliferate exhibit an increased rate of DNA synthesis. A typical way to measure the rate of DNA synthesis is, for example, by pulse-labeling cultures of T cells with tritiated thymidine, a nucleoside precursor which is incorporated into newly synthesized DNA. The amount of tritiated thymidine incorporated can be determined using a liquid scintillation spectrophotometer. Other ways to detect T cell proliferation include measuring increases in interleukin-2 (IL-2) production, Ca2+ flux, or dye uptake, such as 3-(4,5-dimethylthiazol-2-yl)-2,5-diphenyl-tetrazolium. Alternatively, synthesis of lymphokines (such as interferon-gamma) can be measured or the relative number of T cells that can respond to a particular antigen may be quantified.

Detection of antigen-specific antibody production may be achieved, for example, by assaying a sample (e.g., an immunoglobulin containing sample such as serum, plasma or blood) from a host treated with a vaccine according to the present disclosure using in vitro methodologies such as radioimmunoassay (RIA), enzyme linked immunosorbent assays (ELISA), equilibrium dialysis or solid phase immunoblotting including Western blotting. In embodiments ELISA assays may further include antigen-capture immobilization of the target antigen with a solid phase monoclonal antibody specific for the antigen, for example, to enhance the sensitivity of the assay. Elaboration of soluble mediators (e.g., cytokines, chemokines, lymphokines, prostaglandins, etc.) may also be readily determined by enzyme-linked immunosorbent assay (ELISA), for example, using methods, apparatus and reagents that are readily available from commercial sources (e.g., Sigma, St. Louis, MO; see also R & D Systems 2006 Catalog, R & D Systems, Minneapolis, MN).

Any number of other immunological parameters may be monitored using routine assays that are well known in the art. These may include, for example, antibody dependent cell-mediated cytotoxicity (ADCC) assays, secondary in vitro antibody responses, flow immunocytofluorimetric analysis of various peripheral blood or lymphoid mononuclear cell subpopulations using well established marker antigen systems, immunohistochemistry or other relevant assays. These and other assays may be found, for example, in Rose et al. (Eds.), Manual of Clinical Laboratory Immunolog, 5th Ed., 1997 American Society of Microbiology, Washington, DC.

Accordingly it is contemplated that the compositions provided herein will be capable of eliciting or enhancing in a host at least one immune response that is selected from a Th1-type T lymphocyte response, a TH2-type T lymphocyte response, a cytotoxic T lymphocyte (CTL) response, an antibody response, a cytokine response, a lymphokine response, a chemokine response, and an inflammatory response. In certain embodiments the immune response may comprise at least one of production of one or a plurality of cytokines wherein the cytokine is selected from interferon-gamma (IFN-γ), tumor necrosis factor-alpha (TNF-α), production of one or a plurality of interleukins wherein the interleukin is selected from IL-1, IL-2, IL-3, IL-4, IL-6, IL-8, IL-10, IL-12, IL-13, IL-16, EL-18 and EL-23, production one or a plurality of chemokines wherein the chemokine is selected from MIP-la, MIP-1β, RANTES, CCL4 and CCL5, and a lymphocyte response that is selected from a memory T cell response, a memory B cell response, an effector T cell response, a cytotoxic T cell response and an effector B cell response. See, e.g., WO 94/00153; WO 95/17209; WO 96/02555; U.S. Pat. Nos. 6,692,752; 7,084, 256; 6,977,073; 6,749,856; 6,733,763; 6,797,276; 6,752, 995; 6,057,427; 6,472,515; 6,309,847; 6,969,704; 6,120, 769; 5,993,800; 5,595,888; Smith et al., 1987 J Biol Chem. 262:6951; Kriegler et al., 1988 Cell 53:45 S3; Beutler et al., 1986 Nature 320:584; U.S. Pat. Nos. 6,991,791; 6,654,462; 6,375,944.

The nanoalum formulations of the present invention are useful for the treatment or prevention of disease such as pertussis, tuberculosis, leprosy, malaria, HIV, leishmaniasis and influenza. In particular, the ability of the nanoalum formulations to promote Th1 immunity makes them particularly useful in this regard.

C. Diagnostic Agents

In some embodiments the agent is a diagnostic agent. Thus in these embodiments, the compositions described comprise the nanoalum particles provided herein, and further comprise a diagnostic agent and are useful for the diagnosis of any disease, condition, or disorder.

In some embodiments, the diagnostic agents are useful for the detection cancer. Compositions and methods are known in the art for identifying subjects having, or suspected of being at risk for developing cancer are described herein. Diagnosis of cancer in a subject having or suspected of being at risk for having cancer may be accomplished by any of a wide range of art-accepted methodologies, which may vary depending on a variety of factors including clinical presentation, degree of progression of the cancer, the type of cancer, and other factors. Examples of cancer diagnostics include histopathological, histocytochemical, immunohistocytochemical and immunohistopathological examination of patient samples (e.g., blood, skin biopsy, other tissue biopsy, surgical specimens, etc.). PCR tests for defined genetic (e.g., nucleic acid) markers, serological tests for circulating cancer-associated antigens or cells bearing such antigens, or for antibodies of defined specificity, or other methodologies with which those skilled in the art will be familiar. See, e.g., U.S. Pat. Nos. 6,734,172; 6,770,445; 6,893,820; 6,979,730; 7,060,802; 7,030,232; 6,933,123; 6,682,901; 6,587,792; 6,512,102; 7,078,180; 7,070,931; JP5-328975; Waslylyk et al., 1993 Eur. J Bioch. 211 (7): 18. Any one or more of these diagnostic agents can be included in the compositions comprising nanoalum particles described herein.

In some embodiments, the diagnostic agents are useful for the detection of an autoimmune disease. Detection of an autoantibody thus permits early discovery or recognition of presence or risk for developing an autoimmune disease. Based on these findings, a variety of autoantibodies against autoantigens have been discovered and the autoantibodies against autoantigens have been measured in clinical tests (e.g., U.S. Pat. Nos. 6,919,210, 6,596,501, 7,012,134, 6,919, 078) while other autoimmune diagnostics may involve detection of a relevant metabolite (e.g., U.S. Pat. No. 4,659, 659) or immunological reactivity (e.g., U.S. Pat. Nos. 4,614, 722 and 5,147,785, 4,420,558, 5,298,396, 5,162,990, 4,420, 461, 4,595,654, 5,846,758, 6,660,487). Thus in some embodiments, the compositions comprising any one of the nanoalum particles described herein, further comprise an autoantibody useful for the detection of an autoantigen.

In one embodiment, the diagnostic agents are useful for the detection of infectious diseases. Compositions and methods are known in the art for identifying subjects having, or suspected of being at risk for having, an infection with an infectious pathogen as described herein.

For example, the bacterium *Mycobacterium tuberculosis* cases tuberculosis (TB). Thus, in some embodiments, the compositions comprising any of the nanoalum particles described herein further comprise an agent for diagnosing tuberculosis. Diagnostic kits containing such polypeptides or DNA sequences and a suitable detection reagent may be used for the detection of *Mycobacterium* infection in patients and biological samples. Antibodies directed against such polypeptides are also provided.

In some embodiments, the compositions comprising any of the nanoalum particles described herein further comprise an agent for diagnosing malaria, using any one of the diagnostic agents described below. An in vitro diagnostic method for malaria in an individual is known, comprising placing a tissue or a biological fluid taken from an individual in contact with a molecule or polypeptide composition, wherein said molecule or polypeptide composition comprises one or more peptide sequences bearing all or part of one or more T epitopes of the proteins resulting from the infectious activity of *P. falciparum*, under conditions allowing an in vitro immunological reaction to occur between said composition and the antibodies that may be present in the tissue or biological fluid, and in vitro detection of the antigen-antibody complexes formed (see, e.g., U.S. Pat. No. 7,087,231).

Expression and purification of a recombinant *Plasmodium falciparum* (3D7) AMA-1 ectodomain have been described. Previous methods have produced a highly purified protein which retains folding and disulfide bridging of the native molecule. The recombinant AMA-1 is useful as diagnostic reagents well as in antibody production, and as a protein for use alone, or as part of, a vaccine to prevent malaria. (U.S. Pat. No. 7,029,685)

Polynucleotides have been described in the art that encode species-specific *P. vivax* malarial peptide antigens which are proteins or fragments of proteins secreted into the plasma of a susceptible mammalian host after infection, as have monoclonal or polyclonal antibodies directed against these antigens. The peptide antigens, monoclonal antibodies, and/or polyclonal antibodies are utilized in assays used to diagnose malaria, as well as to determine whether *Plasmodium vivax* is the species responsible for the infection. (U.S. Pat. No. 6,706,872) Species-specific *P. vivax* malarial peptide antigens have also been reported which are proteins or fragments of proteins secreted into the plasma of a susceptible mammalian host after infection, as have monoclonal or polyclonal antibodies directed against these antigens. The peptide antigens, monoclonal antibodies, and/or polyclonal antibodies are utilized in assays used to diagnose malaria, as well as to determine whether *Plasmodium vivax* is the species responsible for the infection (see, e.g., U.S. Pat. No. 6,231,861).

A recombinant *Plasmodium falciparum* (3D7) AMA-1 ectodomain has also been expressed by a method that produces a highly purified protein which retains folding and disulfide bridging of the native molecule. The recombinant AMA-1 is useful as a diagnostic reagent, for use in antibody production, and as a vaccine. (U.S. Pat. No. 7,060,276) Similarly known are the expression and purification of a recombinant *Plasmodium falciparum* (3D7) MSP-142, which retains folding and disulfide bridging of the native molecule. The recombinant MSP-142 is useful as a diagnostic reagent, for use in antibody production, and as a vaccine. (U.S. Pat. No. 6,855,322)

Diagnostic methods for the detection of human malaria infections to identify a subject having or suspected of being at risk for having an infection with a malaria infectious pathogen are thus known according to these and related disclosures. Specifically, for example, blood samples are combined with a reagent containing 3-acetyl pyridine adenine dinucleotide (APAD), a substrate (e.g. a lactate salt or lactic acid), and a buffer. The reagent is designed to detect the presence of a unique glycolytic enzyme produced by the malaria parasite. This enzyme is known as parasite lactic acid dehydrogenase (PLDH). PLDH is readily distinguishable from host LDH using the above-described reagent. Combination of the reagent with a parasitized blood sample results in the reduction of APAD. However, APAD is not reduced by host LDH. The reduced APAD may then be detected by various techniques, including spectral, fluorimetric, electrophoretic, or colorimetric analysis. Detection of the reduced APAD in the foregoing manner provides a positive indication of malaria infection (e.g., U.S. Pat. No. 5,124,141). In another methodology for diagnosing malaria, a polypeptide comprising a characteristic amino acid sequence derived from the *Plasmodium falciparum* antigen GLURP, is recognized in a test sample by a specific antibody raised against or reactive with the polypeptide. (U.S. Pat. No. 5,231,168).

In some embodiments, the compositions comprising any of the nanoalum particles described herein further comprise an agent useful for diagnosing Leishmaniasis, using any one of the diagnostic agents described below. Leishmaniasis is a widespread parasitic disease with frequent epidemics in the Indian subcontinent, Africa, and Latin America and is a World Health Organization priority for vaccine development. A complex of different diseases, *Leishmania* parasites cause fatal infections of internal organs, as well as serious skin disease. One of the most devastating forms of leishmaniasis is a disfiguring infection of the nose and mouth. The number of cases of leishmaniasis is increasing, and it is now out of control in many areas. Leishmaniasis is also on the rise in some developed countries, specifically southern Europe as a result of HIV infection. Available drugs are toxic, expensive, and require long-term daily injections.

*Leishmania* are protozoan parasites that inhabit macrophages or the white blood cells of the immune system. The parasites are transmitted by the bite of small blood sucking insects (sand flies), which are difficult to control, as they inhabit vast areas of the planet.

Visceral leishmaniasis is the most dangerous of the three manifestations of the disease. It is estimated that about 500,000 new cases of the visceral form (kala-azar or "the killing disease") occur each year. More than 200 million people are currently at risk for contracting visceral leishmaniasis. Over 90 percent of visceral leishmaniasis cases occur in India, Bangladesh, Sudan, Brazil, and Nepal. Most of the deaths occur in children. Those with the cutaneous forms are often left permanently disfigured.

*Leishmania* infections are difficult to diagnose and typically involve histopathologic analysis of tissue biopsy specimens. Several serological and immunological diagnostic assays have, however, been developed. (U.S. Pat. No. 7,008,774; Senaldi et al., (1996) J. Immunol. Methods 193:9 5; Zijlstra, et al., (1997) Trans. R. Soc. Trop. Med. Hyg. 91:671 673, Badaro, et al., (1996) J. Inf. Dis 173:758 761; Choudhary, S., et al., (1992) J. Comm. Dis. 24:32 36; Badaro, R., et al., (1986) Am. J. Trop. Med. Hyg. 35:72 78; Choudhary, A., et al., (1990) Trans. R. Soc. Trop. Med. Hyg. 84:363 366; and Reed, S. G., et al., (1990) Am. J. Trop. Med. Hyg. 43:632 639). The promastigotes release metabolic products into the culture medium to produce conditioned medium. These metabolic products are immunogenic to the host. See Schnur, L. F., et al., (1972) lsrl. J. Med. Sci. 8:932 942; Sergeiev, V. P., et al., (1969) Med. Parasitol. 38:208 212; El-On, J., et al., (1979) Exper. Parasitol. 47:254 269; and Bray, R S., et al, (1966) Trans. R. Soc. Trop. Med. Hyg. 60:605 609; U.S. Pat. Nos. 6,846,648, 5,912,166; 5,719,263; 5,411,865).

In some embodiments, the compositions comprising any of the nanoalum particles described herein further comprise an agent useful for diagnosing HIV, using any one of the diagnostic agents described below. Methods for diagnosing HIV infections are known, including by virus culture, PCR of definitive nucleic acid sequences from patient specimens, and antibody tests for the presence of anti-HIV antibodies in patient sera, (see e.g., U.S. Pat. Nos. 6,979,535, 6,544,728, 6,316,183, 6,261,762, 4,743,540).

VI. Kits

Also contemplated in certain embodiments are kits comprising the herein described compositions comprising nanoalum particles, which may be provided in one or more containers. In one embodiment all components of the compositions are present together in a single container, but the embodiments are not intended to be so limited and also contemplate two or more containers in which, for example, an immunological adjuvant composition is separate from, and not in contact with, the antigen component. By way of non-limiting theory, it is believed that in some cases administration only of the immunological adjuvant composition may be performed beneficially, whilst in other cases such administration may beneficially be separated temporally and/or spatially (e.g., at a different anatomical site) from administration of the antigen, whilst in still other cases administration to the subject is beneficially conducted of a vaccine composition as described herein and containing both antigen and adjuvant composition, and optionally other herein described components as well.

In some embodiments, a vial of the kit comprises a composition comprising nanoalum particles.

In some embodiments, one vial of the kit comprises a composition comprising nanoalum particles, and a second vial of the kit contains a bioactive agent. In some embodiments, the kit comprises a third via) containing an adjuvant.

In some embodiments, one vial of the kit comprises a composition comprising nanoalum particles, and a second vial of the kit contains an adjuvant. In some embodiments, the kit comprises a third vial containing a bioactive agent.

The kits of the present disclosure may further comprise instructions for use as herein described or instructions for mixing the materials contained in the vials. In some embodiments, the material in the vial is dry or lyophilized. In some embodiments, the material in the vial is liquid.

A container according to such kit embodiments may be any suitable container, vessel, vial, ampule, tube, cup, box, bottle, flask, jar, dish, well of a single-well or multi-well apparatus, reservoir, tank, or the like, or other device in which the herein disclosed compositions may be placed, stored and/or transported, and accessed to remove the contents. Typically such a container may be made of a material that is compatible with the intended use and from which recovery of the contained contents can be readily achieved. Non-limiting examples of such containers include glass and/or plastic sealed or re-sealable tubes and ampules, including those having a rubber septum or other sealing means that is compatible with withdrawal of the contents using a needle and syringe. Such containers may, for instance, by made of glass or a chemically compatible plastic or resin, which may be made of, or may be coated with, a material that permits efficient recovery of material from the container and/or protects the material from, e.g., degradative conditions such as ultraviolet light or temperature extremes, or from the introduction of unwanted contaminants including microbial contaminants. The containers are preferably sterile or sterilizable, and made of materials that will be compatible with any carrier, excipient, solvent, vehicle or the like, such as may be used to suspend or dissolve the herein described vaccine compositions and/or immunological adjuvant compositions and/or antigens and/or recombinant expression constructs, etc.

The following Examples are offered by way of illustration and not by way of limitation.

EXAMPLES

Example 1 Preparation of PEG and PAA Nanoalum Formulations

Preparation of Nanoalum Formulations. Aluminum hydroxide 2% or Al(OH)3, aluminum hydroxide, aluminum oxyhydroxide 2% (Alhydrogel® 85) were purchased from EM Sargeant as a wet gel suspensions. The following lipids were purchased from Corden Pharma (Liestal, Switzerland): Distearoylglycerophosphoethanolamine (DSPE), N-Carbonyl-methoxypolyethyleneglycol-750)-1,2-distearoyl-sn-glycero-3-phosphoethanolamine (mPEG750-DSPE), N-(Caronyl-methoxypolyethyleneglycol-2000)-1,2-distearoyl-sn-glycero-3-phosphoethanolamine (mPEG2000-DSPE), N-(Carbonyl-methoxypolyethyleneglycol-5000)-1, 2-distearoyl-sn-glycero-3-phosphoethanolamine (mPEG5000-DSPE), 1,2-dipalmitoyl-sn-glycero-3-phosphoethanolamine-N-[methoxy(polyethylene glycol-2000] (mPEG2000-DPPE), 1,2-dipalmitoyl-sn-glycero-3-phosphoethanolamine-N-[methoxy(polyethylene glycol)-5000] (mPEG5000-DPPE), N-(Carbonyl-methoxypolyethyleneglycol-2000)-1,2-dimuristoyl-sn-glycero-3-phosphoethanolamine (mPEG2000-DMPE), and N-(Carbonyl-methoxypolyethylenglycol-5000)-1,2-dimyristoyl-sn-glycero-3-phosphoethanolamine (mPEG5000-DMPE). Alhydrogel® '85' was purchased from EM Sergeant Pulp and Chemical Company (Clifton, New Jersey) and manufactured by Brenntag (Mulheim an der Ruhr, Germany). Poly(acrylic acid) (PAA) was purchased from Sigma Aldrich.

Preparation Nanoalum formulations. Briefly PEG Nanoalum was manufactured by diluting 40 ml of Alhydrogel® (10 mg/ml aluminum) into 60 ml water and heating in Crest Powersonic CP230D (Trenton, NJ) water bath at ~60° C. for 2 hours. DSPE or PEGylated DSPE phospholipid was added to the heated Alhydrogel® solution at the indicated concentrations, ranging from ~0.5 to 30 mg/ml phospholipid (Table 3). All formulations were returned to the ~60° C. water bath to dissolve visible phospholipid aggregates. The Microfluidics M110P (Newton, MA), equipped with a diamond F12Y interaction chamber followed by a ceramic H30Z auxiliary processing module, was used for processing the formulations at 30,000 psi for up to 10 passes with recirculating chilled water to prevent temperature increase during processing. 50-µl aliquots were removed between selected passes for particle size characterization by dynamic light scattering. The remaining formulation was collected after the 10th pass and placed on a stability schedule to monitor particle size. Selected formulations manufactured on the 11 OP microfluidizer were filtered through at 0.2-µm Supor membrane prior to in vivo biological activity evaluation. Selected formulations were processed using a Silverson high-shear mixer (East Longmeadow, MA) for 5 minutes at 5000 rpm instead of microfluidization.

For PAA nanoalum formulations, PAA with an average molecular weight of 2000 was purchased from Sigma Aldrich. The 50% wt in water stock solution was diluted in water to yields a 30% wt in water. 16 g of the 30% wt PAA was combined with 160 g a stock 10 mg/ml Alhydrogel® solution and pH adjusted to 6.6 with 10M NaOH. The formulations were processed using a 110P Microfluidizer at 30 k PSI, 4° C. for 1, 3, 6, 10, 15, or 20 passes.

Particle Analysis of Nanoalum Formulations. Formulations were characterized for particle size by dynamic light scattering (DLS) using the Malvern Instruments (Worcestershire, UK) Zetasizer Nano-S or Nano-ZS and by laser diffraction particle analysis using the Beckman Coulter (Brea, California) LS230. Particle size information was also obtained by sedimentation analysis and cryoTEM (described below). For DLS analysis, alum formulations were diluted 1:100 fold in water in a 15-ml polystyrene disposable cuvette. DLS measurements were made in triplicate and values were reported as the scattering intensity-based average particle diameter, Z-ave. Samples run on the DLS were measured against polystyrene standards (polystyrene refractive index=1.55-1.59) of 60 and 200 nm; aluminum has a refractive index of 1.24. For laser diffraction-based measurements, Alum samples were directly into the water-filled sample chamber a Polarization Intensity Differential Scattering (PIDS) value between 50%±5% was reached. The Offsets (establishes electrical noise baseline by measuring the voltages of the circuit while the laser is off) option was set to 60 seconds. Background Measure to 90 seconds, run lengths to 90 second intervals, and pump speed to 50%. Prior to and between sample analysis, the LS230 was de-bubbled three times.

Sedimentation Analysis. Laser scattering optical profiling was conducted using the LUM GmbH (Boulder. Colorado) LUMiReader, equipped with three lasers of wavelengths 470 nm, 630 nm, and 870 nm. Particle settling rates were determined based on changes in the laser light transmission profile from a vertical cross-section of the sample cuvette. 4 mL of undiluted formulation were added directly to a cylindrical glass cell for analysis. Samples were measured for at 25° C. for 2-4 hours at a max tilt angle of 30° with measurement scans collected every 60 seconds. Furthermore, based on the multiwavelength analysis method (2), particle settling rates could be used to calculate volume-based particle size distributions for particles larger than ~0.5 μm.

Antigen Adsorption. Antigen binding to the nano-alum formulations was assayed by silver-stain SDS-PAGE. Prior to centrifugation, samples were mixed in the following order: alum formulation, TLR ligand, antigen, and diluent (saline or glycerol solution). Samples were then centrifuged on the Beckman Coulter (Brea, California) Optima Max-XP Ultra Centrifuge for 30 minutes at 35,000×g at 4° C., 30 μl of sample was mixed with 10 μl of 4× reduced LDS Sample Buffer, following which 20 μl was loaded into a 12 lane SDS-PAGE gel with 8 μl of SeeBlue2 Prestained Standard. Each gel was run for 55 minutes at 190 V and then placed into a fixing solution of 50:40:10 EtOH:CH3COOH:H2O for a minimum of 2 hours or up to overnight. The gel was then stained according to the directions provided by Sigma-Aldrich (Saint Louis, MO) ProteoSilver Plus Silver Stain Kit.

TLR Ligand Adsorption. TLR-9 ligand binding to the nano-alum formulations was assayed by silver-stain SDS-PAGE using the same centrifugation and dilution preparation, gel conditions, and staining kit. Presence of a dark brown band between the 3-6 kDa range indicated that TLR-9 ligand was present on the gel. TLR-4 ligand binding to the nano-alum formulations was assayed by centrifuging the TLR-4 ligand with the nano-alum formulations and testing the supernatant for presence of unbound TLR-4 ligand diluted 1:5 into mobile phase A (75:15:10 [v:v:v] methanol:chloroform:water with 20 mM ammonium acetate and 1% acetic acid). Each supernatant sample was injected at 50-μl volume onto a Waters Co. (Milford, MA) Xbridge BEH Shielf RP18 column attached to an Agilent Model 1100 HPLC (Santa Clara, CA). A gradient consisting of mobile phases A and B (1:1 [v:v]methanol:chloroform with 20 mM ammonium acetate and 1% acetic acid) was run over 25 minutes. Detection was done by an ESA Biosciences (Chelmsford, MA) Coronoa Charged Aerosol Detector (CAD). Quantitation was performed using a GLA standard infected at different volumes in mobile phase B to create a standard curve.

XRD. X-ray powder diffraction analysis was performed on four samples sent to Triclinic Labs (West Lafayette, IN) to determine the effect of varied processing on the same PEGylated lipid/Alhydrogel® composition. Samples were ultracentrifuged and x-ray powder diffraction (XRPD) analyses were carried out of the still-wet solids and the supernatant liquids. The Rigaku Smart-Lab X-ray diffraction system (The Woodlands, TX) was configured for reflection Bragg-Brentano geometry using a line source X-ray beam. The S-ray source is a copper long fine focus tube that was operated at 40 kV and 444 mA. That source provides an incident beam profile at the sample that changes from a narrow line at high angles to a broad rectangle at low angles. Beam conditioning slits are used on the line X-ray source to ensure that the maximum beam sixe is less than 10 mm both along the line and normal to the line. The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. Typically, the Rigaku Smart-Lab is operated to give peak widths of 0.1° 2Θ or less. The axial divergence of the X-ray beam is controlled by 5.0° Soller slits in both the incident and diffracted beam paths. Samples were placed in low-background, silicon holders using light manual pressure to keep the sample surfaces flat and level with the reference surface of the holder. Each sample was analyzed from 2 to 40° 2Θ using a continuous scan of 6° 2Θ per minute with a effected step size of 0.02° 2Θ. Each data set was digitally filtered to remove low-frequency responses. Examination of the resulting patterns allowed identification of two distinctly different crystalline responses: Gaussian-style peaks and Lorentzian-style peaks. Gaussian-style peaks are normally associated with microcrystalline material, and is used to designate materials containing both crystalline and amorphous regions. Lorentzian-style peaks are normally associated with nanocrystalline materials, and contain crystallites that are nanometer sized.

CryoEM Analysis of Nanoalum Formulations

CryoEM analysis was performed by NanoImaging Services. Briefly, samples for EM analysis were preserved in vitrified ice supported by holey carbon films on 400-mesh copper grids. Each sample was prepared by applying a 3 μL drop of sample suspension to a cleaned grid, blotting away with filter paper, and immediately proceeding with vitrification in liquid ethane. Grids were stored under liquid Nitrogen until transferred to the electron microscope for imaging. Electron microscopy was performed using an FEI Tecnai T12 electron microscope, operating at 120 keV equipped with an FEI Eagle 4 k×4 k CCD camera. Vitreous ice grids were transferred into the electron microscope using a cryostage that maintains the grids at a temperature below −170° C. Images of each grid were acquired at multiple scales to assess the overall distribution of the specimen.

After identifying potentially suitable target areas for imaging at lower magnifications, high magnification images were acquired at nominal magnifications of 110,000× (0.10 nm/pixel), 52,000× (0.21 nm/pixel) and 21,000× (0.50 nm/pixel). The images were acquired at a nominal underfocus of −2 μm (110,000×), −3 μm to −2 μm (52,000×) and −5 μm (21,000×) and electron doses of ~9-42 e/Å2.

Generation of Nanoalum Formulations-Development of Sizing Agents PEG Nanoalums-Pegylated Phospholipid Sizing Agents Aluminum oxyhydroxide (alum) in solution generally aggregates into larger typical crystalline arrays or sheets. Unprocessed Alhydrogel® forms larger typical crystalline arrays or sheets of aluminum hydroxide molecules of 1 micron or larger in unprocessed alum formulations. In data not shown, experiments were performed to determine if milling or processing by microfluidization of aluminum hydroxide solutions alone under various conditions would result in nanoalum formulations, however we were unable to determine a condition under which microfluidization of stock aluminum hydroxide alone would yield a stable nanoalum formulation.

Without wishing to be bound by theory, it was theorized that the addition of a sizing agent or stabilizing agent may be required to prevent or disrupt the aggregation of the aluminum hydroxide molecules. Phospholipids are routinely added as emulsifiers and stabilizers of microspheres in aqueous solutions, and were initially chosen as sizing agents. Initial experiments were performed to test whether inclusion of sizing agents such as phospholipids during milling or processing of the alum solutions could result in nanoalum formulations. Experiments were performed on the inclusion of a single phospholipids species DSPE, DPPE and DMPE with differing acyl chain lengths of 18, 16, and 14 carbons respectively. In data not shown, the phospholipids tested were not found to be effective sizing agents and did not prevent aggregation of the alum molecules.

Additional experiments were performed to determine if the addition of a polyethylene glycol moiety linked to the phospholipid would create an effective sizing agent. In order to evaluate whether inclusion of a sizing agent could disrupted aggregation of the alum molecules to produce a nanoalum formulation, a PEG5000-DSPE stock solution was milled by microfluidization at 30 k PSI for 10 passages and immediately mixed bench top with the stock aluminum hydroxide solution to yield an 8 mg/ml PEG5000-DSPE:4 mg/ml Alhydrogel® formulation. CryoEM analysis of the admixed microfluidized pegylated phospholipid:aluminum hydroxide formulation demonstrated that admixing aluminum hydroxide with the microfluidized pegylated lipid does not disrupt the formation of the larger crystalline aggregates of alum and does not produce a nanolum formulation.

Subsequent experiments were performed to determine if nanoalum formulations could be produced by addition of the sizing agent during the milling or processing of the stock alum formulation. A series of experiments were performed to evaluate DSPE, DPPE, and DMPE pegylated phospholipids with a range of molecular weight polyethylene glycol moieties (ranging from 750-5000 kD Mr) linked to a variety of phospholipids with differing acyl chain lengths (DSPE, DPPE, DMPE having acyl chain lengths of 18 carbon, 16 carbon and 14 carbon respectively) admixed with stock alum formulations during the milling or sizing process under by under various conditions were performed to determine if the addition of the sizing agent during milling or processing of the alum could produce a nanoalum formulation Formulations were analyzed for particle size by Malvern analysis and cryoEM analysis. Milling or processing alum in the presence of a sizing agent such as a pegylated phospholipid produced nanoalum formulations with particle sizes ranging from approximately 400-70 nm (Table 4 and data not shown).

Analysis of data presented demonstrates that the method or conditions used to mill the alum in the presence of the sizing agent can produce nanoalum formulation having different defined particle sizes. Unprocessed alum has a size of approximately 1000-10,000 nm (Table 4). Mixing alum in the presence of 5000 kD molecular weight PEG-DSPE as a sizing agent (e.g., 8 mg:4 mg sizing agent:alum), with a Silverson mixer at 5000 rpm for 5 minutes produces a nanoalum formulation with an average particle size of approximately 400 nm (Table 3 and data not shown). Microfluidization at 10 k PSI for 1 passage of a 5000 kD molecular weight PEG-DSPE admixed alum (e.g., 8 mg:4 mg sizing agent alum) produces a nanoalum formulation with an average particle size of approximately 120-130 nm. Processing the admixed alum 5000 kD molecular weight PEG-DSPE solution for 6, 10, 15 or up to 20 passages produces nanolaum formulations with an average particle size 70 nm (Table 3 and data not shown). The data in Table 4 as well data not presented demonstrates that changing the processing either by changing the milling or sizing equipment (for example a silverson mixer or microfluidizer) or conditions of milling (for example for a microfluidizer by varying the PSI or number of passages) of alum in the presence of the sizing agent can produce a nanoalum formulation having a range of nanoparticle sizes (400 nm, 120 nm, 70 nm). Based on the data presented one of ordinary skill in the art could mill or process alum in the presence of a sizing agent such as a pegylated lipid using well recognized techniques and equipment such as a high energy source or high energy input to achieve a nanoalum formulation of a desired size range.

Further analysis of the data in Table 4 and data not shown demonstrate that a wide range of molecular weights of the PEG moieties linked to the DSPE phospholipid produce effective sizing agents. As demonstrated in Table 4 and data not shown varying the PEG length from 750 to 2000 to 5000 kD (Table 3 and data not shown) did not affect the particle size of the nanoalum formulation when milled under the milling conditions determined to produce a 70 nm particle size nanoalum formulation. Thus pegylated phospholipid sizing agents of the present disclosure can comprise a wide range of molecular weight polyethylene glycol moieties.

Experiments were performed to determine if varying the ratio of alum to the pegylated phospholipid sizing agents could be used to control the particle size of the nanoalum formulation.

The data presented in Table 4 indicate that varying the ratio of sizing agent to alum can be used to affect the particle size of the nanoalum formulation. For example, to reproducibly produce nanoalums with average particle sizes of approximately 300-400 nm for a DSPE-PEG5000 sizing agent can be produced at a ratio of 1:1 of alum to sizing agent whereas increasing of sizing agent to 1:1.5 or 12 reproducible produces nanoalums of approximately 100 nm or 70-80 nm respectively. Comparing the DSPE-PEG2000 sizing agent, the DPPE-PEG-5000 or the PA A200 sizing agents demonstrate that the optimal ratios of alum to sizing agent in the range of 1:2-1:3 reproducibly produces nanoalums of 70-80 nm alums. In addition the data in Table 4 and data not shown demonstrate that the acyl chain length of the pegylated phospholipid did not affect the ability sizing agent to produce nanoalums of the desired size range. Varying acyl chain lengths of 18 carbons (18C DSPE), 16 carbons (16C DPPE) and 14 carbons (14C DMPE) of the pegylated phospholipid when mixed with the alum formulation and milled by the same process all produced nanoalum formulations having the same particle size (Table 4 and data not shown). Thus pegylated phospholipid sizing agents of the present disclosure can comprise phospholipids with differing acyl chain lengths.

Reducing PH via Concentrated HCL, HNO₃, and Proprionic Acid

Dramatic reduction of the pH of alum using concentrated acid when subjected to milling via ultrasonication for five minutes produced nanoalum formulations of the present disclosure. Both concentrated hydrochloric and nitric acid added to achieve a final pH of 1.0 were tested and both produced nanoalum formulations of 324 nm (data not shown) with high polydispersity. Thus concentrated acid solutions may be suitable as sizing agents to produce nanoalum formulations for certain aspects of the present disclosure. However, since a final pH of 1.0 for the nanoalum formulation may not be advantageous for all aspects of the present disclosure including delivery of proteins, peptides, and nucleic acids, additional acids with a lower overall pH profile were evaluated further.

Briefly, 4 mM Oleic acid was mixed with water to get 30 ml emulsion. This mixture was treated with Ultra sonic probe (at 40% power) for 10 min. Equal volumes of a 1.6% volume by weight Alhydrogel® stock solution was mixed with an equal volume of the emulsified oleic acid solution to produce an Alhydrogel®:Oleic acid formulation 0.8 v %:2 mM Oleic acid which was further sonicated for 10 min using Ultra sonic probe at the 40%. power. The resulting nanoalum had a particle size of 194 nm and a final pH of 2.4. Thus for certain aspects. Oleic Acid is a suitable sizing agent for nanoalum formulations.

Alum was sonicated as described above in with stirring and the addition of 5% Acetic Acid till the pH was adjusted to 6.1, 5.1, or 4.5. Acetic Acid as a sizing agent produced effective nanoalum formulations with average particle sizes of approximately 100-130 nm. In addition the nanoparticles of the formulation were positively charged as measure by Zeta potential. Thus for some aspects of the present disclosure, acetic acid may be an effective sizing agent to produce nanoalums of the present disclosure.

PAA Nanoalums-Polyacrylic Acid (PAA) as a Sizing Agent

For initial experiments the use of PAA as a sizing agent to produce nanoalums was evaluated by mixing under strong stirring 40 g of 0.4 wt % of alum was with a 20 wt % solution of PAA and the pH adjusted to pH 6.0 with concentrated ammonium hydroxide resulting in nanoalums of particle sizes of approximately 140 nm with negatively charged nanoparticles as measured by Zeta potential.

For subsequent experiments, briefly 20% by weight of PAA was mixed with a stock alum solution, the pH adjusted to 6.6 with sodium hydroxide and milled using a 110P microfluidizer. Based on data from development of the PEG nanoalum formulations, the formulation was milled via microfluidization with 4° C. recirculation and evaluated at 30 k psi for 3, 6, 10, and 15 passes respectively. 3 or 6 passes yielded nanoalums with particle sizes of approximately 100 nm with no appreciable effect in particle size observed between 3 and 6 passages. Increasing the number of passages from 10 to 15 consistently produced nanoalums of approximately 70-85 nm particle size and good polydispersity. For subsequent experiments 10 passages was utilized. The data indicate that PAA is an effective sizing agent for nanoalum formulations.

Stability and Characterization of Nanoalum Formulations

Figure 1B:
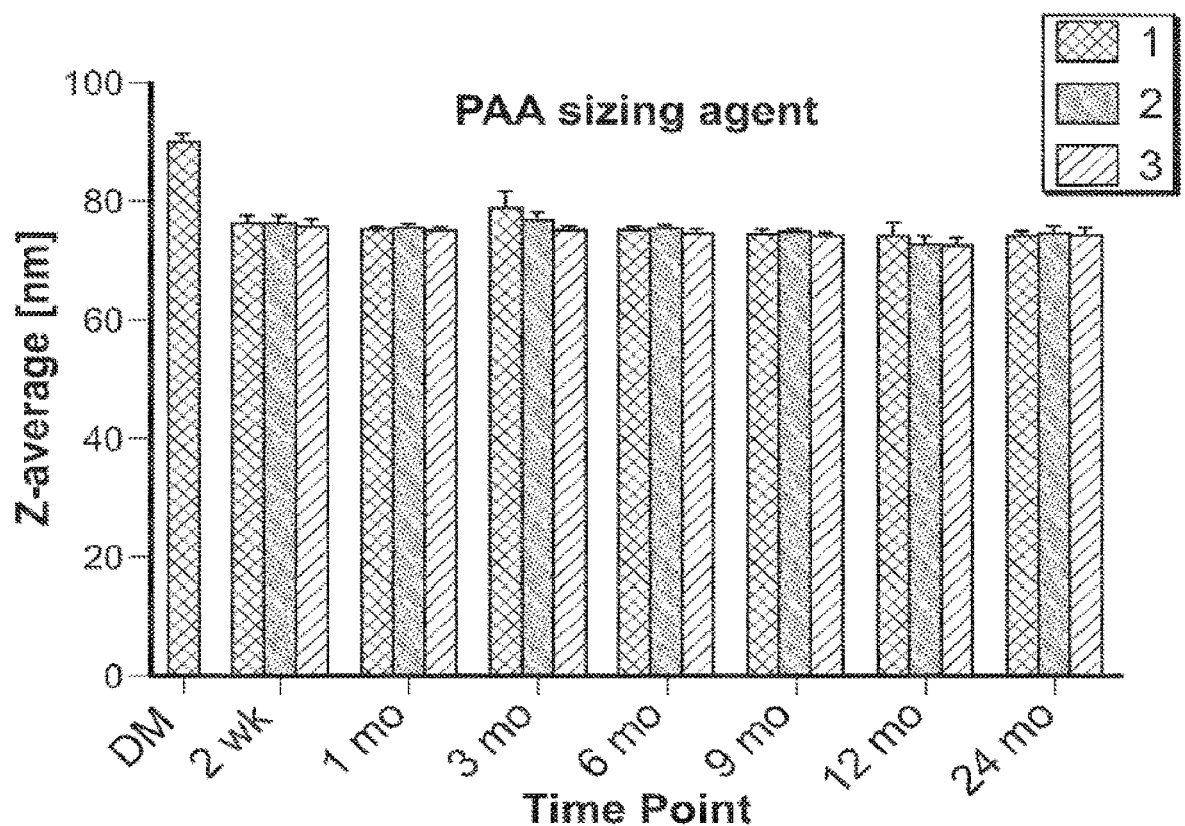
Figure 1C:
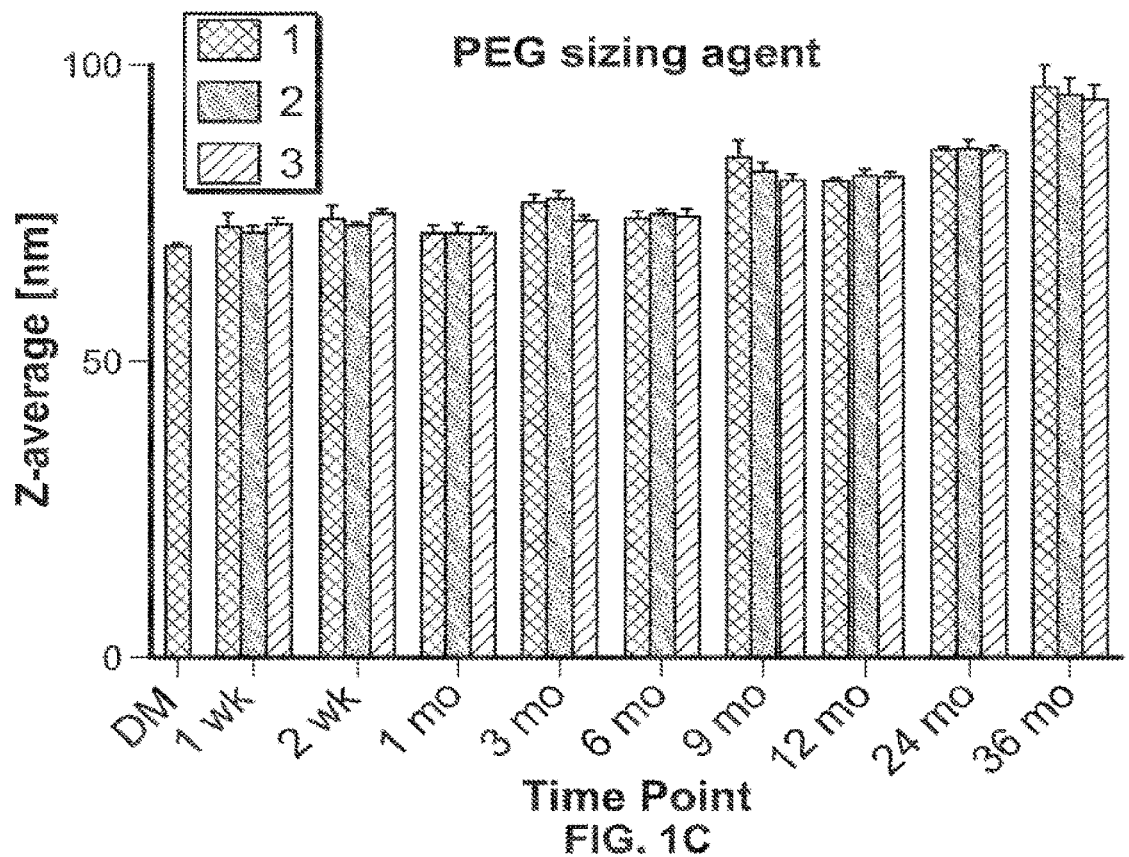

The data showed that nanoalum formulation can be generated by milling in the presence of suitable sizing agents such as pegylated lipids and polyacrylic acid. However for commercialization as a delivery formulation for drugs or biologics, a desirable characteristic of the formulation is that the particle size should be stable over time. Experiments were performed to determine if aqueous PEG nanoalum or PAA nanoalum formulations were stable and maintained the initial particle size or did not increase in size or aggregate beyond an average size of 200 nm when milled to a 70 nm initial particle size. Briefly PEG nanoalum formulations and PAA nanoalums were prepared as previously described and stored at 4° C. as indicated. Triplicates samples were removed at 1 week, 2 weeks, and 1, 3, 6, 9, and 12 months after preparation and assessed for particle size and polydispersity as described herein. The data in FIG. 1B for the PAA nanoalum formulations demonstrates that the PAA nanoalum formulations are incredibly stable and maintain an average particle size of approximately 75 nm over 1, 3, and 6 months as tested and beyond to 12 months (data not shown). Similarly the PEG nanoalum formulations shown in 1C are also remarkably stable and maintain an average particle size of around 75 nm for a period of 1, 3, 6, 9 and up to 12 months when measured by dynamic light scattering with a Malvern Zetasizer.

Figure 1D:
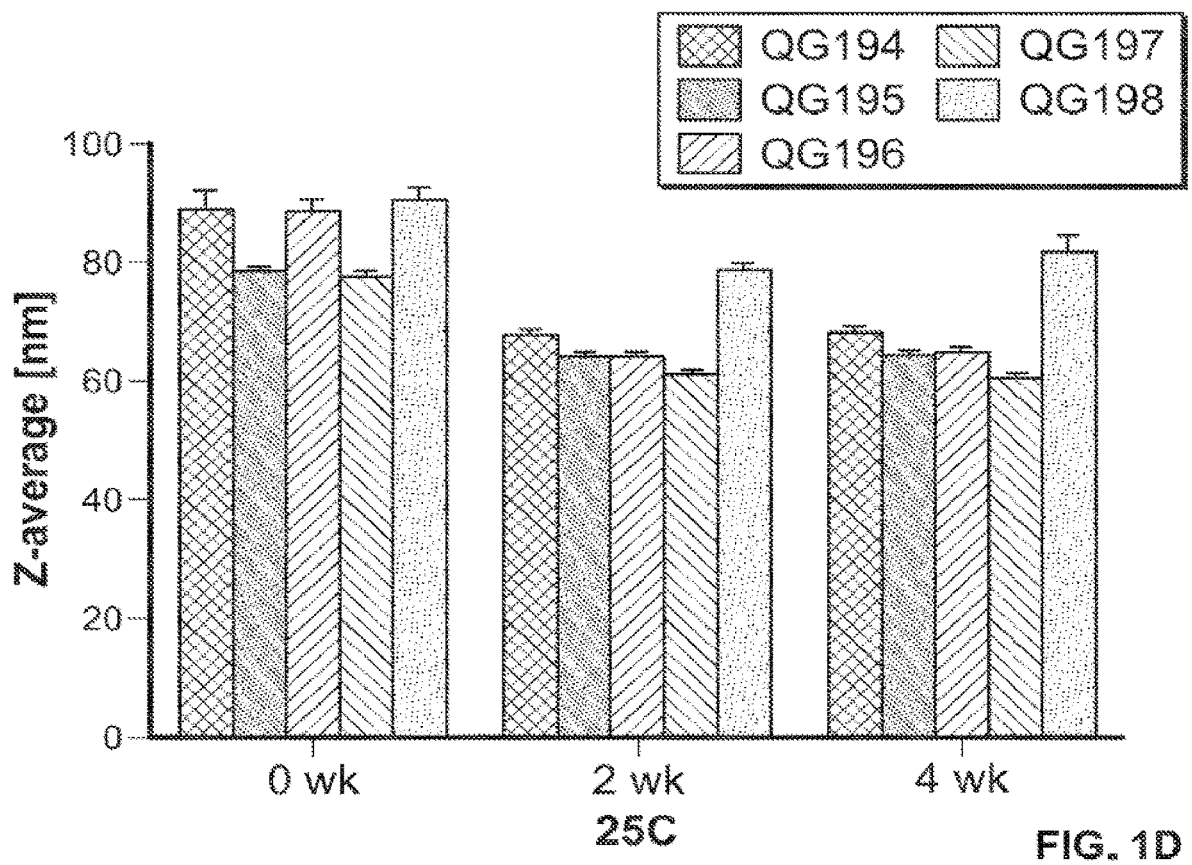
Figure 1E:
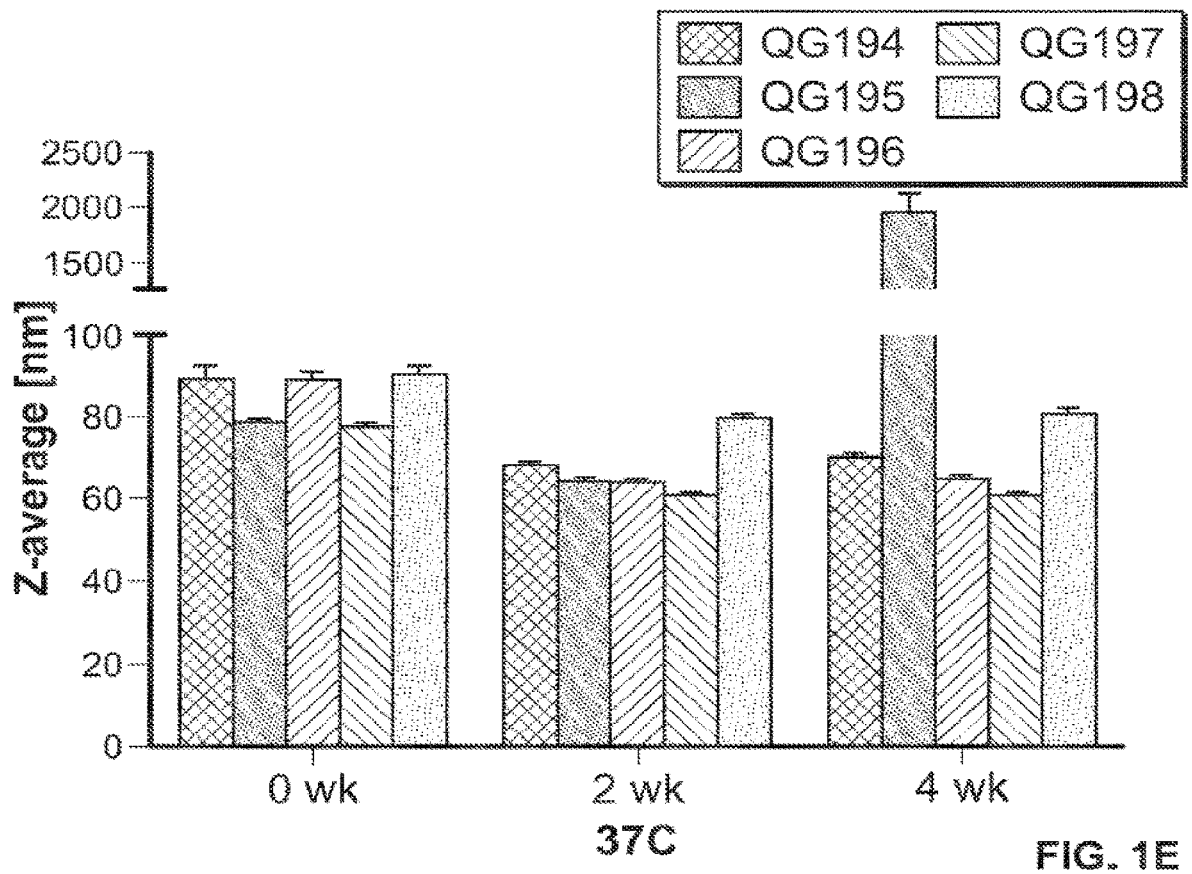
Figure 1F:
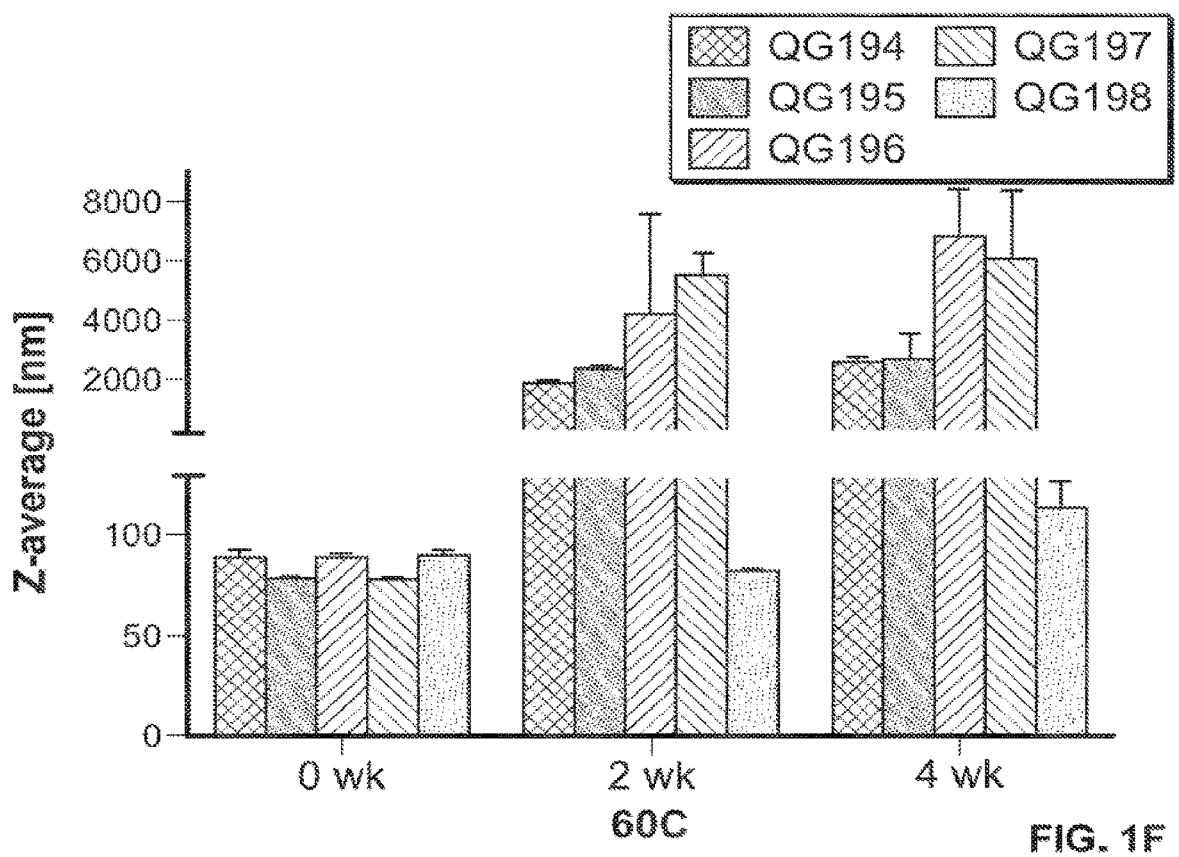

Long term stability at 2-8° C. is an important characteristic for vaccine formulations, but maintenance of cold chain storage can be a limiting factor for delivery of vaccines for global health. We tested whether the nanoalum formulation of the present disclosure were thermostable over a range of temperatures (25° C., 37° C. and 65° C.) over a time period of 4 weeks. Briefly triplicates samples were stored at the desired temperature and assayed for changes in average particle size and polydispersity as measured by dynamic light scattering using a Malvern zetasizer. We further analyzed the affect the PEG length and acyl chain length might have on thermostability of the aqueous nanoalum formulations by evaluating PEG5000-DSPE (18 carbon acyl chain length), PEG2000-DMPE (14 carbon acyl chain length), PEG2000-DPPE (16 carbon acyl chain length) PEG750-DSPE (18 carbon acyl chain length), and PEG200-DSPE (18 carbon acyl chain length). The data in FIG. 1D-F demonstrates that PEG2000-DSPE was extremely stable at temperatures up to 25° C. and 37° C. with little to no aggregation or change in particle size at 0, 2 or 4 weeks and even at 60° C., was stable for up to 2 weeks. Even at 4 weeks at 60° C. the PEG2000-DSPE nanoalum formulation demonstrated only a slight increase in particle size and still had an average particle size of 114 nm indicating that nanoalums containing sizing agents may not require cold chain storage. Nanoalum formulations of PEG5000-DSPE (PEG length 5000 and acyl chain length of 18C), PEG2000-DPPE (PEG length 2000 and acyl chain length of 16C) and PEG750-DSPE (PEG length 750 and acyl chain length of 18C) demonstrated thermostability at 25° C. and 37° C. for 0, 2 and 4 weeks, but at 60° C. were thermolabile and demonstrated particle aggregation at 2 and 4 weeks with average particle sizes greater than 2000 nm. Interestingly the nanoalum formulation PEG2000-DMPE (PEG length 2000 and acyl chain length of 14C) was stable at 25° C. for up to 4 weeks and at 37° C. for 2 weeks but at 37° C. and 60° C. was not stable and demonstrated particle aggregation with average particle sizes greater than 2000 nm. Thus the nanoalum formulations of the present disclosure demonstrate enhanced thermostability. Thermostability of nanoalum formulations may not only allow for greater global access to areas without dedicated cold chain storage, but also may reduce the overall cost the formulation. In the figure legends, QG194 is PEG5000-DSPE; QG195 is PEG2000-DMPE; QG196 is PEG2000-DPPE; QG197 is PEG750-DSPE, QG198 is PEG2000-DSPE.

In order to further assess the stability of the nanoalum we evaluated the effect of freeze-thaw cycling on the colloidal stability of alum and nanoalum formulations. The pre-freeze particle size of formulations were measured using Horiba LA-960 for alum formulation and Malvern Zetasizer for nanoalum formulations. Formulations were frozen in a dry ice/acetone batch then thawed in a 37 C water bath. Particle sizes were measured and compared before and after the freeze-thaw cycle. The mean particle size of Alhydrogel® 85 (alum) increased 160% after one freeze-thaw cycle, indicating failure of colloidal stability. The mean particle size of (nanoalum-poly(acrylic acid)) showed no significant change in particle size after 3 freeze-thaw cycles. The mean particle size of nanoalum-PEG increased 273% after 1 freeze thaw cycle, indicated failure of colloidal stability. Alhydrogel® 85 adjuvant is colloidally unstable after one freeze thaw cycle, suggesting poor resistance to the destabilizing effects of freezing. On the other hand, nanoalum stabilized with poly(acrylic acid) shows excellent stability after repeated freeze-thaw cycles, which can facilitate long-term cryo-preservation of nanoalum-PAA formulations.

Alum is an attractive adjuvant that has been described to bind or adsorb protein antigens through the electrostatic interactions (involving the Al3+ ion or negatively-charged counter ion) [11], metal ion coordination and hydrogen bonding with water molecules and hydroxyl groups [9], [10] and [12]; and in some cases hydrophobic interactions [13]. There is some debate in the field regarding the extent to which, if at all, protein adsorption is required for the adjuvant property of alum. We tested whether nanoalums of the present disclosure with a much smaller surface area and particle size compared to alum would efficiently adsorb antigens. Briefly, Prior to centrifugation, samples were mixed in the following order: alum formulation, TLR ligand (GLA or CpG 5 μg), antigen (TB fusion protein ID93 (0.5 μg), and diluent (saline or glycerol solution). Samples were centrifuged 30 minutes at 35,0000×g at 4° C. and 30 μl of sample from the unpelleted supernatant was mixed with 10 μl of 4× reduced LDS Sample Buffer. 20 μl was loaded into a 12 lane SDS-PAGE gel with 8 μl of SeeBlue2 Prestained Standard. Each gel was run for 55 minutes at 190 V and then placed into a fixing solution of 50:40:10 EtOH:CH3COOH: H2O for a minimum of 2 hours or up to overnight. The gel was then stained with ProteoSilver Plus Silver Stain Kit to determine if ID93 was present in the supernatant or was pelleted due to adsorption to alum. The data demonstrated (Data not shown) that the sizing agents present in nanoalum formulations do not interfere with binding or association of antigen or adjuvants and are suitable as delivery vehicles for bioactive agents of the present disclosure. In order to confirm that the sizing agent, PEG-5000 DSPE, would not interfere with protein adsorption to alum or interfere with the assay in general, the ID93 fusion protein was admixed with the TLR4 adjuvant, GLA, and alum. The absence of the 62 Kd ID93 band on the gel confirms that DSPE-PEG5000 does not block adsorption of antigen to the micron (0.5-1.0 micron) sized alum particles. The nanoalum formulations of the present disclosure with particle sizes of less than 100 nm containing the sizing agent PEG DSPE of differing PEG lengths of 5000, 2000, or 750 or a fixed PEG length of 2000 linked to a phospholipids of differing acyl chain lengths of 18 carbons (DSPE), 16 carbons (DPPE) or 14 carbons (DMPE) are equally capable of adsorbing the fusion protein ID93 as demonstrated by the absence of the 62 Kd ID93 band on the gel (Data not shown). Thus the reduction in the average surface area or particle size of a nanoalum formulation does not result in a decreased adsorption of proteins antigens making them particularly useful formulations for vaccines.

Figure 2:
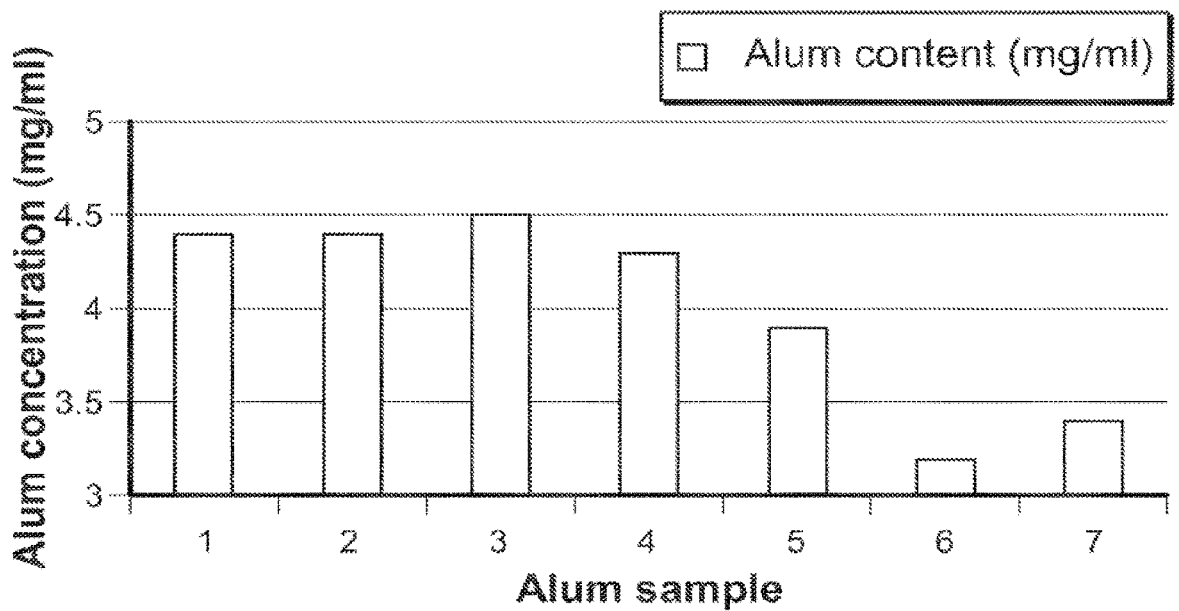
FIG. 2: Nanoalum formulations having varies sizing agent contain the predicted alum content. Nanoalum formulation were prepared with PEG sizing agents of differing lengths linked to phospholipids of varying acyl chain lengths have the predicted alum content. Nanoalum formulations comprised of sizing agents with a phospholipid of 18C (DSPE) and varying PEG lengths of 5000 (sample 1), 2000 (sample 4) and 750 (sample 5) contain roughly equivalent amounts of the predicted 4 mg/ml alum starting value as measure by ICP-OES testing ranging from 3.9 mg/ml for PEG750-DSPE (sample 5) to 4.5 mg/ml for PEG2000-DPPE (sample 3).

We next characterized the concentration of the aluminum hydroxide present in nanoalum panicles of the present disclosure. Briefly nanoalum formulations containing sizing agents of varying PEG lengths (5000, 2000, 750) or phospholipids with varying acyl chain lengths (18 C-DSPE, 16C-DPPE, or 14C DMPE were processed as described herein and the aluminum content was assessed by ICP-OES testing (FIG. 2). The data in FIG. 2 demonstrate nanoalum formulations comprising varying sizing agents contain the predicted alum content when prepared with PEG sizing agents of differing PEG lengths linked to phospholipids of varying acyl chain lengths. Nanoalum formulations comprised of sizing agents with phospholipids of 18C (DSPE) and varying PEG lengths of 5000 (sample 1), 2000 (samples 2-4) and 750 (sample 5) produced from stock 4 mg/ml alum formulations and the indicated sizing agents milled by microfluidization at 30,000 psi for 10 passes at 4° C. contain roughly equivalent amounts of the predicted 4 mg/ml starting value as measure by ICP-OES testing ranging from 3.9 mg/ml for PEG750-DSPE (sample 5) to 4.5 mg/ml for PEG2000-DPPE (sample 3). Interesting both the alum milled in the absence of the sizing agent as well as unprocess alum contained lowered alum content (3.2 mg/ml for sample 6 and 3.4 mg/ml for sample 7 respectively).

The data demonstrate that processing or milling of aluminum hydroxide (Alhydrogel®) in the presence of an appropriate sizing agent can produce stable nanoalum formulation suitable for delivery of agents of the present disclosure. Sizing Agents of the present disclosure include without limitation pegylated phospholipids and PAA.

Figure 3A:
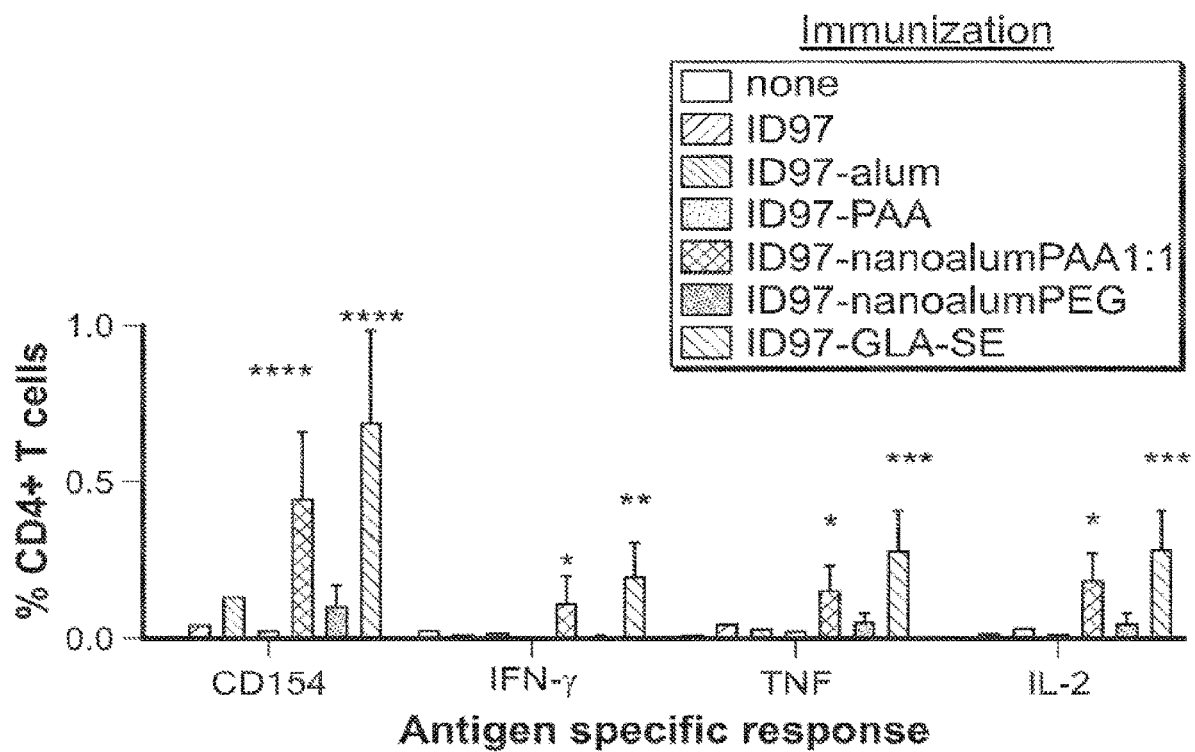
FIG. 3A-D: Mice were immunized with 2.5 μg of ID97 alone or adjuvanted with alum, PAA, nanoalum PAA, nanoalum PEG, or the TLR4 agonist GLA-SE. One week after immunization splenocytes were isolated and either unstimulated or stimulated with the ID97 protein in the presence of Brefeldin A for 8 hours at 37° C. Cells were then stained for surface expression of CD4, CD8, and CD44, as well as intracellular expression of CD154, IFN-γ, TNF-α, IL-2, GM-CSF, IL-5, and IL-17A. Antigen specific responses were calculated as the frequency of $CD4^+$ T cells making a response in the ID97 stimulated samples minus the unstimulated samples.
Figure 3B:
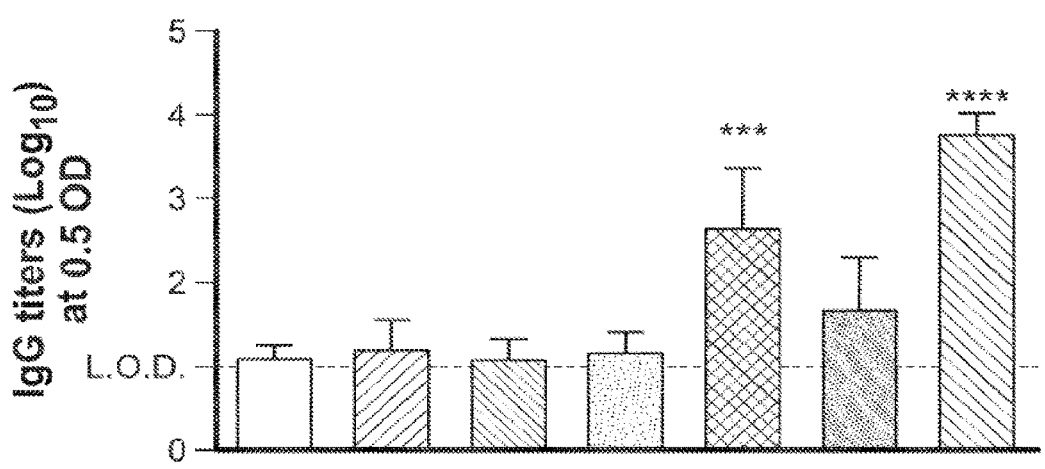
Figure 3C:
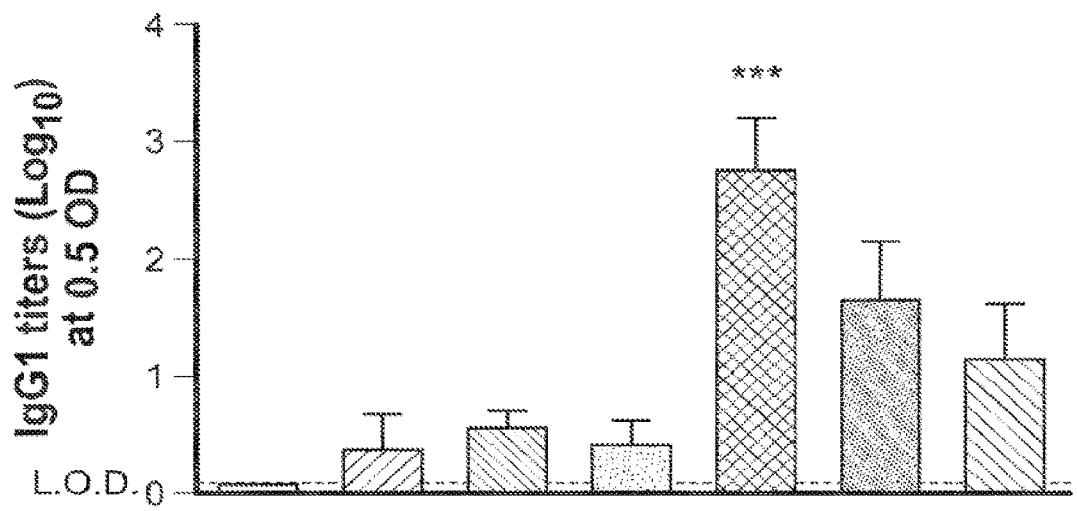
Figure 3D:
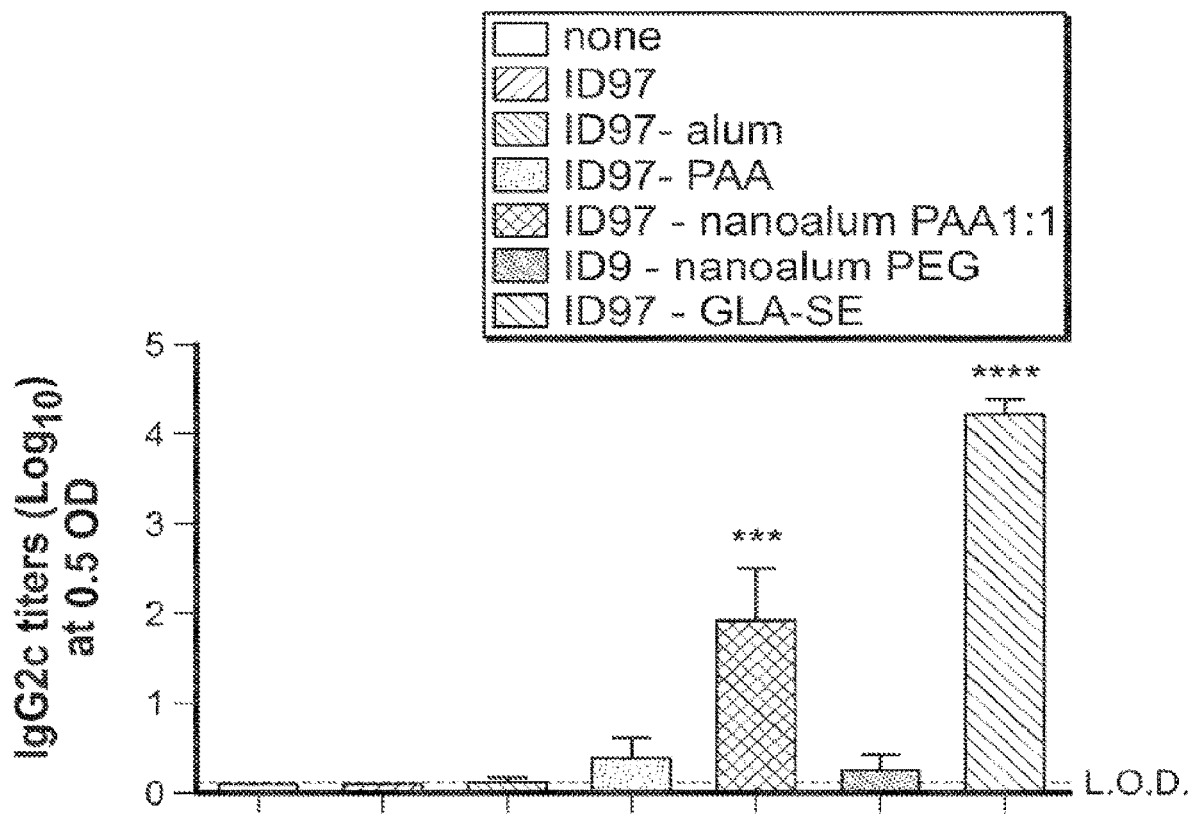

Example 2 Use of PEG5000 and PAA Nanoalum Formulations for the Delivery of Proteins or Peptides (e.g., IP97) to Stimulate an Immune Response To assess the potential for modifications to aluminum hydroxide (Alhydrogel®) that result in smaller alum particles on the scale of 100 nm to promote a Th1-skewed immune response we generated two nanoalum adjuvants, one based on polyacrylic acid (PAA) and one based on PEG5000. To test the adjuvant potential of these candidates we immunized 8 week old female C57Bl/6 mice (5 per group) purchased from The Jackson Laboratory with the recombinant antigen, ID97—a recombinant fusion of four proteins from *Mycobacterium tuberculosis*: Rv1886, Rv3478, Rv3619, and Rv2875 ID97 was delivered either alone or adjuvanted with alum (100 μg), PAA, nanoalumPAA 1:1 (100 μg of alum, 70 nm particle size), nanoalumPEG (100 μg of alum, 70 nm particle size), or the TLR4 agonist adjuvant GLA-SE as a positive control for Th1 induction. Mice were immunized once intramuscularly. Seven days after immunization we assessed the ID97-specific $CD4^+$ T cell response by stimulating splenocytes with ID97 in the presences of the Golgi inhibitor Brefeldin A or leaving ceils unstimulated. Cells were then stained for surface expression of CD4, CD8, and CD44, as well as intracellular expression of CD154, IFN-γ, TNF, IL-2, GM-CSF, IL-5, and IL-17A. Antigen specific responses were calculated as the frequency of $CD4^-$ T cells making a response in the ID97 stimulated samples minus the unstimulated samples. FIG. 3A shows the results for Th1 responses in each group. As expected the unadjuvanted, alum adjuvanted and PAA adjuvanted groups show a low frequency of 1097-specific CD4+ T cells based on recall expression of CD154 (a marker for antigen-specificity but not specific for Th1, TH2, or Th17 commitment). Surprisingly the PAA-based nanoalum induced a robust CD4+ T cell response that was characterized by the production of the Th1 hallmark cytokines IFN-γ, TNF, and IL-2. The level of response was similar to that achieved with the positive control adjuvant GLA-SE. The quality of the humoral response was also assessed 7 days after immunization. Only the PAA-based nanoalum and the positive control GLA-SE augmented the ID97 specific IgG2c and IgG titers (FIG. 3B-D). Class switching to IgG2c is influenced by induction of IFN-γ producing Th1 cells, thus this skewing is supportive of PAA-based nanoalum augmenting Th1 responses. Surprisingly PAA-based nanoalum also promoted IgG1 antibody titers, unlike GLA-SE, suggesting it may have a unique mode of action. PAA nanoalum has unique and surprising adjuvant properties to program TH1 responses. Further, these responses are not just a property of the PAA component as that did not have Th1 adjuvant activity on its own.

Figure 4A:
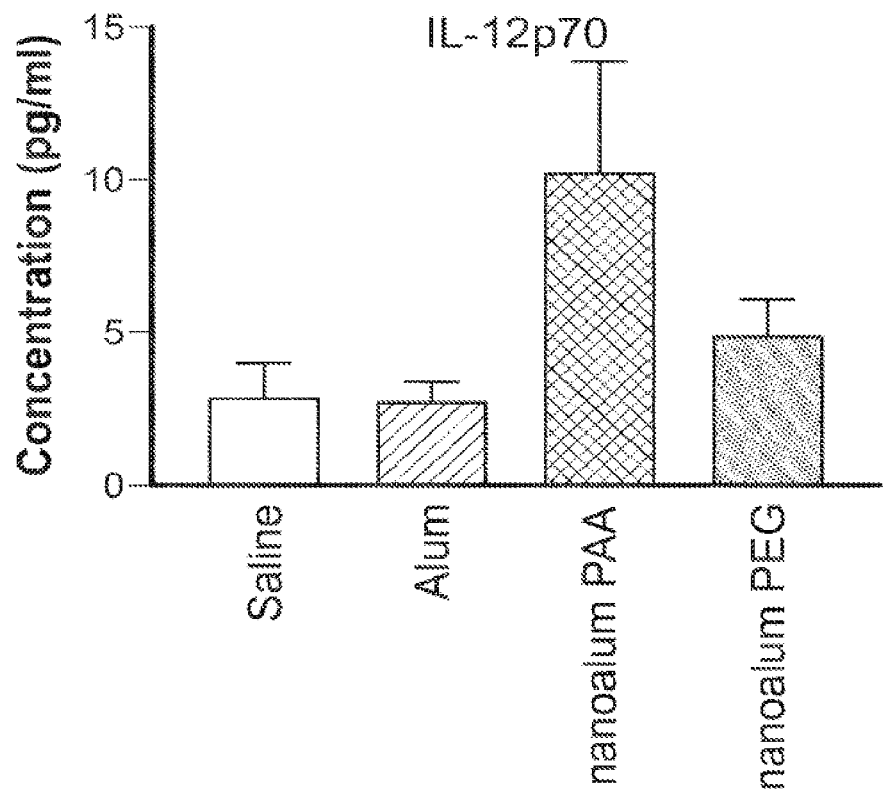
FIG. 4A-C: Female mice were immunized intramuscularly with saline, alum, nanoalum PAA, or nanoalum PEG. One day later, draining lymph nodes were removed and analyzed for secreted cytokines and chemokines by Luminex assay. The data demonstrate that nanoalum PAA augments Th1 skewing cytokines in the draining lymph nodes of mice.
Figure 4B:
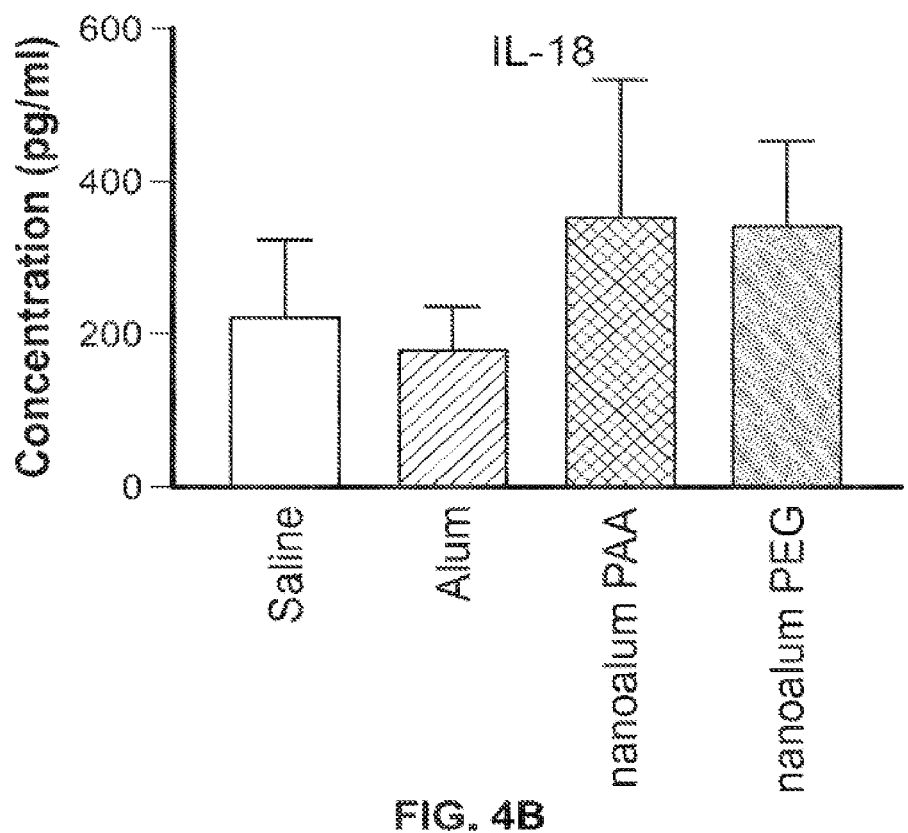
Figure 4C:
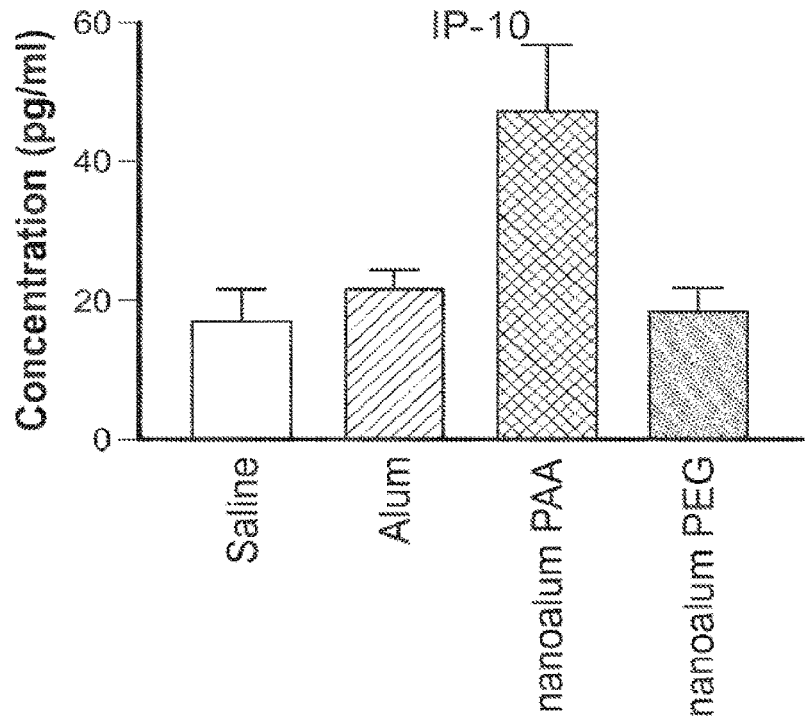
Figure 5:
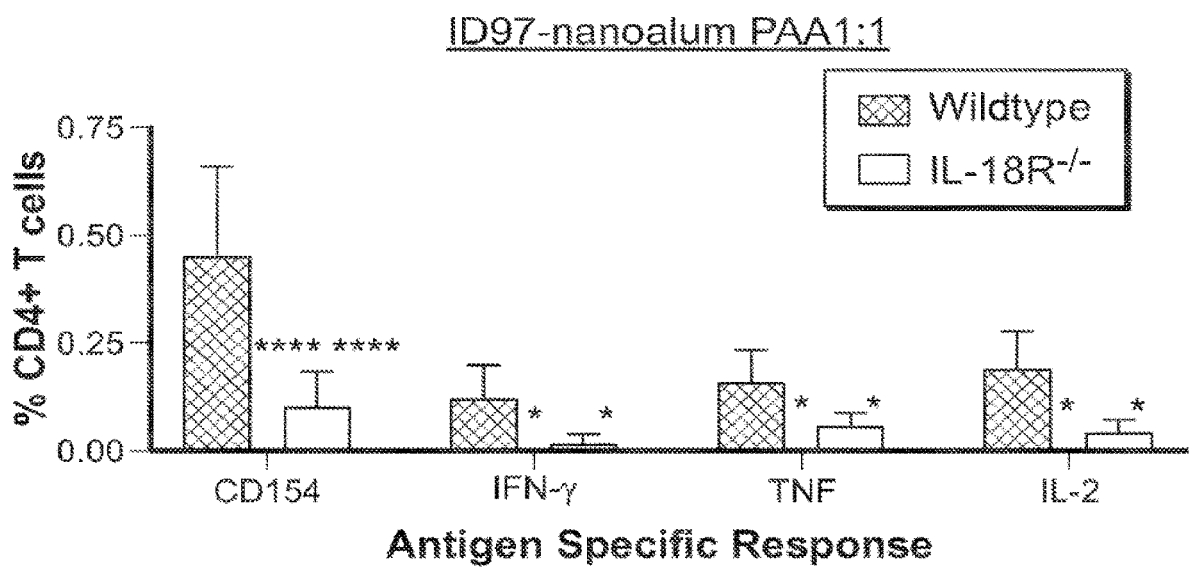
FIG. 5: Wild type mice and IL-18R−/− mice were immunized with 2.5 ug of ID97 and 1 ug of PE recombinant antigens adjuvanted nanoalum PAA. One week after immunization splenocytes were isolated and either unstimulated or stimulated with the ID97 protein in the presence of Brefeldin A for 8 hours at 37 C. Cells were then stained for surface expression of CD4, CD8, and CD44, as well as intracellular expression of CD154, IFN-γ, TNF, IL-2, GM-CSF, IL-5, and IL-17A. Antigen specific responses were calculated as the frequency of CD4 T cells making a response in the ID97 stimulated samples minus the unstimulated samples. The data demonstrates that nanoalum PAA augments Th1 responses via an IL-18R dependent mechanism.

To elucidate the mechanism by which PAA-based nanoalum augments Th1 immunity to vaccine antigens we assessed the concentration of key Th1 augmenting cytokines in the draining lymph nodes of immunized mice 1 day after intramuscular immunization (FIG. 4A-C). IL-12p70 and IL-18 are both crucial for inducing IFN-γ and IP-10 is an early IFN-γ-inducible cytokine. Compared to saline or alum immunization PAA-based nanoalum augmented expression of both IL-18 and IL-12p70 at 1 day after immunization. This likely augmented early expression of IFN-γ as IP-10 expression was also increased in the animals given PAA-based nanoalum. The PEG based nanoalum also increased IL-18, but not IL-12p70 or IP-10 expression further indicating the unique properties of the PAA-based nanoalum. To determine whether this early IL-18 induction was important for the Th1 programming we determined the Th1CD4+ T cell profile in wildtype C57Bl/6 mice and IL-18R$^{-/-}$ mice which are insensitive to IL-18. Compared to the wildtype mice, PAA-based nanoalum failed to induce a Th1 response to the ID97 antigen (FIG. 5).

Taken together these data support the finding that PAA-based nanoalum adjuvants and potentially other nanoparticle alum based adjuvants have unique adjuvant properties compared to alum. These properties specifically include induction of innate cytokines that program Th1 immunity including IL-18 and IL-12p70 as well as IFN-γ responsive cytokines such as IP-10. Further compared to alum, PAA-based nanoalum and potentially other nanoalums augment induction of CD4$^-$ T cells with a Th1 profile (IFN-γ, TNF and IL-2 secretion upon antigen stimulation) and augmentation of IgG2c class switching and antigen-specific antibody titers. These processes depend on activation of the IL-18:IL18R signaling axis. Augmentation of Th1 responses to vaccine antigens has primarily relied on inclusion of known Toll-Like Receptor (TLR) agonists such as MPL, GLA, SLA, CpG, polyIC:LC, or Pam2CSK4. To our knowledge this is the first non-TLR containing adjuvant that can robustly promote Th1 immunity. This has many potential vaccine adjuvant applications including vaccines against diseases such as pertussis, tuberculosis, leprosy, malaria, HIV, leishmaniasis, and influenza.

In data not shown, PAA nanoalum formulations with TB vaccine antigen ID93 also demonstrated enhanced Th1-type adjuvant activity as compared to unprocessed alum.

Example 3. Use of PAA Nanoalum Formulations to Deliver Nucleic Acid Agents

Based on the improved stability, inexpensive and terminally sterilizable large scale amenable manufacture of the nanoalums of the present disclosure we evaluated whether nanoalum formulations were capable of efficient delivery of RNA. We benchmarked the performance of the nanoalum formulations against a cationic emulsion described in the art. Briefly, the cationic emulsion was prepared as described in the art (5) with the resulting emulsion 0.5% w/vol Span 85, 5.0% v/vol Squalene, 0.4% w/vol DOTAP and 0.5% w/vol Tween 80. Replicon RNA was derived from a modified alphaviral genome wherein the structural proteins including capsid and the E glycoprotein (C-E3-E2-6K-E1) are removed, and replaced with a luciferase gene. Briefly the RNA expression vector was a replicon RNA vector expressing luciferase driven by a subgenomic promoter constructed from a modified alphaviral genome deleted of structural proteins including capsid and the E glycoprotein (C-E3-E2-6K-E1) but containing all non-structural genes (ns1-ns5), necessary for replication and expression of the RNA in the cell. To analyze luciferase in vivo as delivered by the RNA replicon and the PAA nanoalum, C57/BL6 mice were anesthetized, shaved and immunized intramuscularly (i.m.) in the thigh with 250 ul of the indicated formulation plus and minus RNA at doses indicated. The RNA dose (concentration) was confirmed prior to injection by measurement using a Nanodrop spectrophotometer. Immunized mice were subjected to anesthesia, shaved and RNA expression assessed using an IVIS Illumina II imager for sixty seconds at 24 hours, 4 days and 7 days post injection. Animals were imaged and relative luminescence units on a log scale was obtained. The examples herein are presented utilize the PAA nanoalum formulations but should not be construed as limiting in scope for nanoalums disclosed herein.

Mice Immunized with RNA Replicon Expression Vectors Formulated with Nanoalum Express RNA In Vivo. To evaluate the ability nanoalums to deliver RNA, mice were injected (3 mice per group) as described with 250 ul of 1:3 PAA nanoalum formulation or a control cationic emulsion formulation as described herein and the replicon RNA at a dose of 1 ug or 0.1 μg. Controls included a saline vehicle, cationic emulsion, PAA nanoalum, or naked replicon RNA at a dose of 30 μg, 1 μg or 0.1 μg. Unformulated replicon RNA expression was not detectable at 24 hours except in one animal that received the highest dose of 30 μg of luciferase replicon RNA (data not shown). However by days 4 and 7, all animals immunized with 30 μg of unformulated luceriase replicon RNA vector had detectable expression compared to vehicle (saline) controls (data not shown). None of the animals that received 1 μg or 0.1 μg of naked replicon RNA had any detectable expression. At a 30-fold lower dose of RNA (1 μg of RNA replicon) admixed with the control cationic emulsion formulation all three animals at 24 hours, 4 days or 7 days post-delivery had detectable luciferase expression (data not shown) demonstrating that the cationic emulsion enhanced the delivery of the RNA replicon resulting in dose sparing as defined by the effect of having equivalent or greater expression of the RNA replicon compared to the unformulated material. The same 30-fold lower dose of RNA (1 μg of RNA replicon) admixed with a PAA nanoalum formulation also demonstrated luciferase expression in one out of three animals at 24 hours and in all immunized animals at 4 days and 7 days respectively (data not shown). At 300-fold lower dose of RNA (100 ng of RNA replicon) admixed with the control cationic formulation, 3 of 3 animals at 24 hours and 2 of 3 animals day 4 or day 7 expressed detectable luciferase (data not shown). At 300-fold lower dose of RNA (100 ng of RNA replicon) admixed with the PAA nanoalum formulation 1 of 3 animals at 24 hours and 2 of 3 animals at days 4 or day 7 expressed detectable luciferase (data not shown).

Figure 6A:
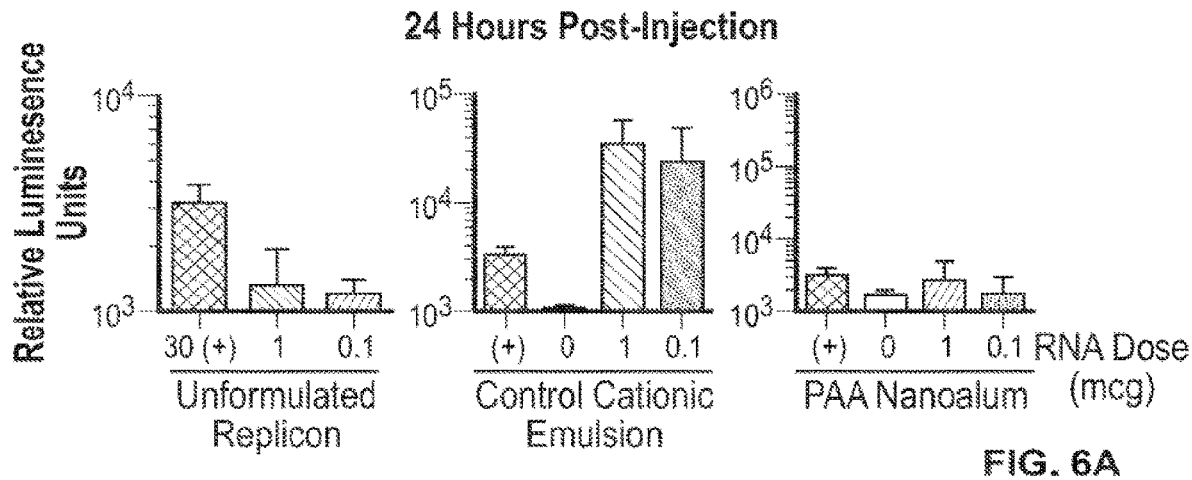
FIG. 6A-C; Mice were immunized with RNA replicon expression vectors formulated with nanoalum. The data demonstrate that at 24 hours post injection the RNA replicon admixed with the cationic emulsion at doses 30 and 300 fold (1, or 0.1 ug) lower than unformulated RNA (30 μg) demonstrated equivalent expression to the unformulated RNA, whereas the PAA nanoalum demonstrated lower expression (FIG. 6A). However by Day 4 and Day 7 post injection the RNA admixed with the either the control cationic emulsion or the PAA nanoalum demonstrate approximately equivalent expression (FIGS. 6B and 6C) at both 1 μg (meg), and 0.1 μg (meg) doses.
Figure 6B:
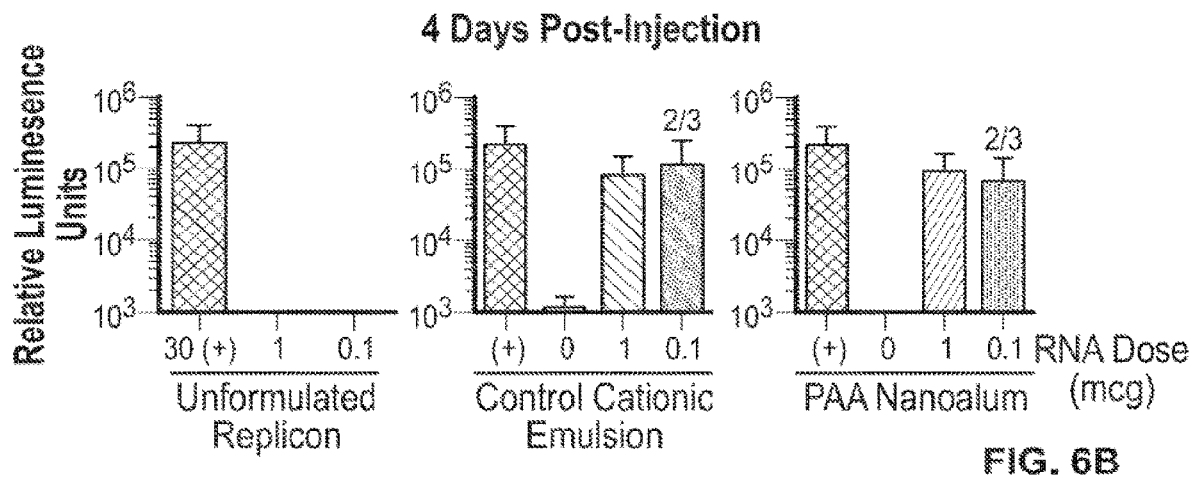
Figure 6C:
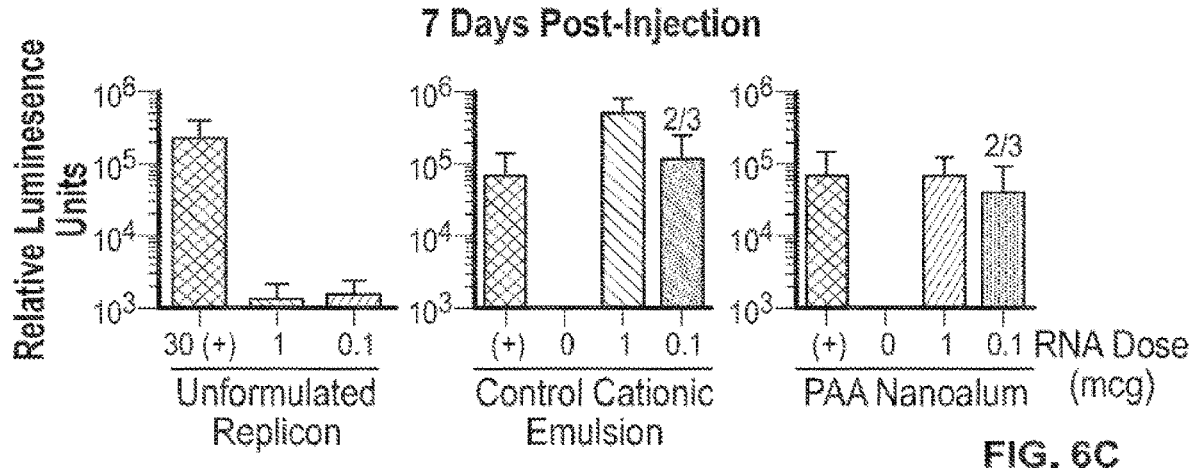

The image data described above was quantified via Circular ROI from Living Image software and is presented graphically in FIGS. 6A-C. The relative luminescence data was expressed on a log scale, grouped according to formulation (unformulated, control cationic emulsion, and PAA nanoalum in the far left, middle and far right panes respectively) and by dose of the replicon vector delivered 0 µg (meg), 1 µg (meg), and 0.1 µg (meg) respectively) at 24 hours (FIG. 6A), 4 days (FIG. 6b) and 7 days (FIG. 6C). The data demonstrate that at 24 hours post injection the RNA replicon admixed with the cationic emulsion at doses 30- and 300-fold (1, or 0.1 µg) lower than unformulated RNA (30 µg) demonstrated equivalent expression to the unformulated RNA. At 24 hours the PAA nanoalum formulated replicon RNA at the same doses 30 and 300 fold (1, or 0.1 µg) lower than unformulated RNA (30 µg) demonstrated lower expression (FIG. 6A) compared to the cationic emulsion but by days 4 and 7 post injection the RNA admixed with the either the control cationic emulsion or the PAA nanoalum demonstrate approximately equivalent expression (FIGS. 6B and C) at both 1 µg (meg), and 0.1 µg (meg) doses. The data demonstrate that the PAA nanoalum formulations are capable of delivery and expression of replicon RNA vectors and have dose sparing properties compared to unformulated RNA.

We next tested whether the sizing agent, PAA, in the nanoalum formulation affected the delivery or expression of the RNA replicon vectors (FIG. 7). In order to determine whether PAA alone was responsible for luciferase expression from the RNA replicon vector, mice were immunized with the unformulated RNA replicon (7A), PAA alone plus the RNA replicon (7B), control cationic emulsion plus RNA replicon (7C), or PAA nanoalum plus RNA replicon (7D) at a dose of 30 µg for unformulated replicon or 1.0 µg and 100 ng for the formulated RNA replicons. Luciferase expression was assessed using an IVIS Illumina II imager and the image data was quantified via Circular ROI as described at 24 hours post injection. The data demonstrate that PAA alone (7B) does not deliver and/or induce an expressible level of an RNA replicon at doses of 0.1 or 1.0 µg whereas the same doses of the RNA replicon formulated or admixed either with the control cationic emulsion or PAA nanoalum demonstrates detectable luciferase expression at levels roughly equivalent to the 30-300-fold higher deliver of the unformulated RNA replicon. The data demonstrate that the sizing agent alone, PAA, is not capable delivering and/or inducing an expressible level of protein from the RNA replicon.

Figure 8A:
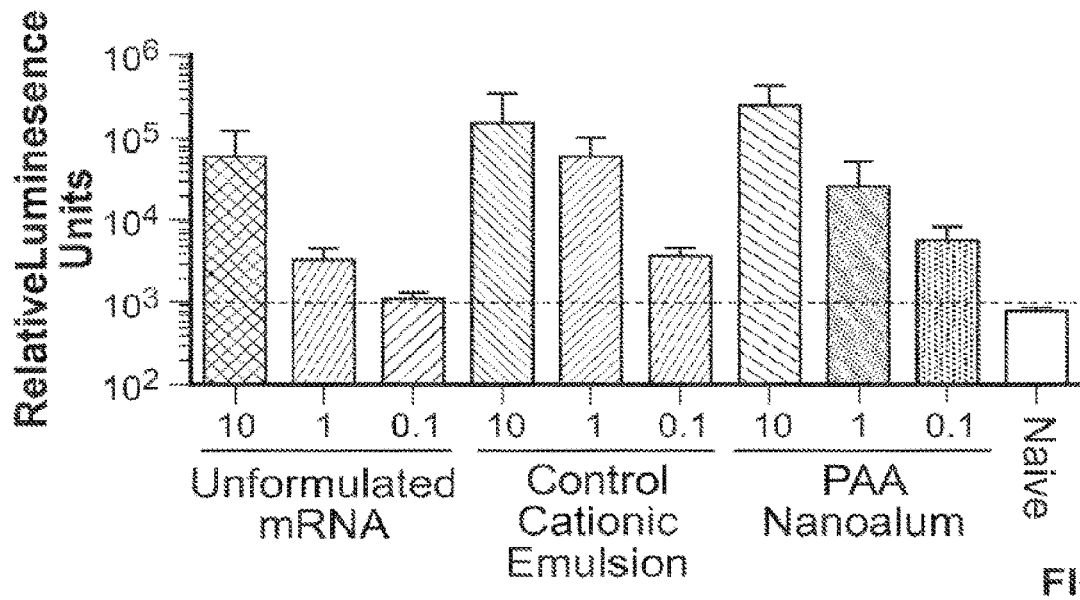
FIG. 8A-C: Mice immunized with mRNA formulated with nanoalum express RNA encoded gene products in vivo. The data demonstrate that nanoalum formulations are capable of delivery of and expression from mRNA and have dose sparing properties compared to unformulated mRNA.
Figure 8B:
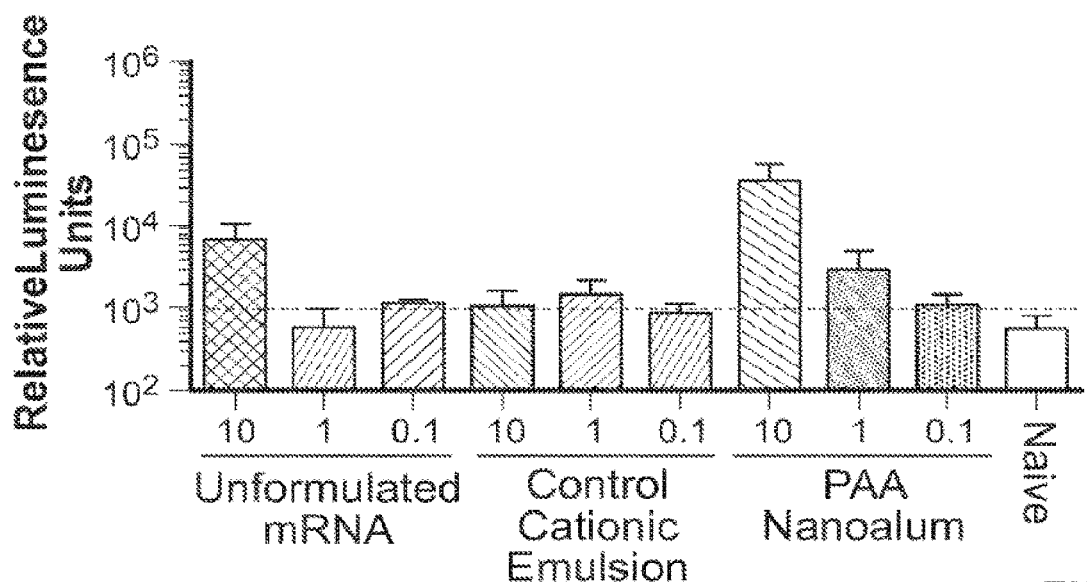
Figure 8C:
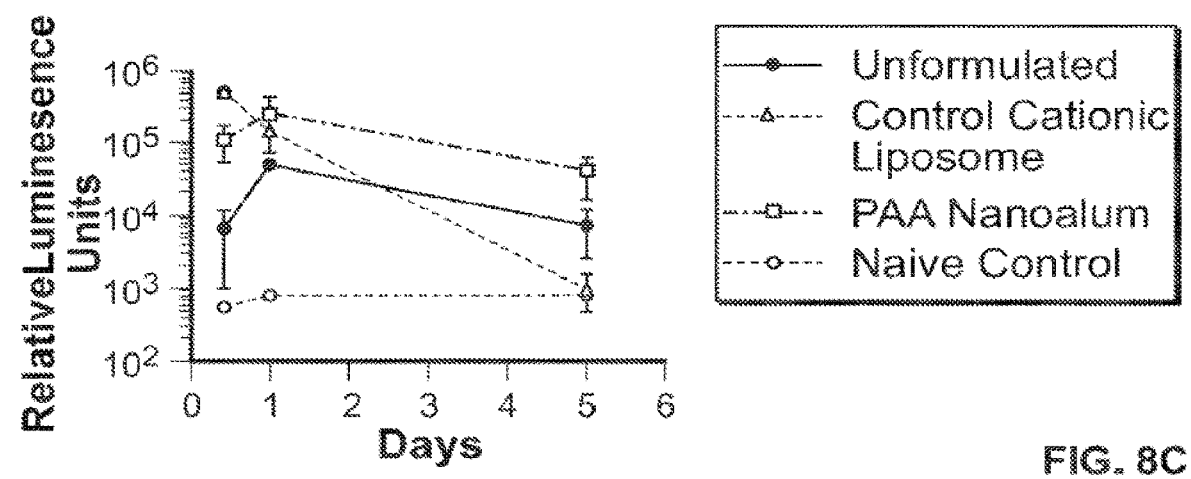

The previous experiments demonstrated the nanoalum formulations of the present disclosure are capable of delivering an RNA replicon which is expressible and demonstrates dose sparing properties when compared to a naked RNA replicon. We next determined if the nanoalum formulation could efficiently deliver a messenger RNA (FIG. 8). To test this we purchased a capped (Cap 0) and polyadenylated mRNA FLuc mRNA optimized for mammalian systems and modified with pseudouridine and 5-methylcytidine that mimics a fully processed mature mRNA (Luc mRNA) from Trilink Biotechnologies. The mRNA expresses a luciferase protein, originally isolated from the firefly, Photinus pyralis. Briefly, the mice (3 per group) were immunized as described with unformulated RNA, mRNA formulated with PAA nanoalum or mRNA formulated with control cationic emulsion at RNA doses of 1 µg, 1 ug or 0.1 µg and RNA. RNA expression assessed using an IVIS Illumina II imager at 6 hours, 24 hours (FIG. 8A) and 5 days (FIG. 8B) and the imaged data was quantified via Circular ROI. The data in FIG. 8A at 24 hours post injection demonstrates animal s that received unformulated mRNA (left group) had detectable luciferase expression at both the 10 µg and 1 µg mRNA dose level but not at 0.1 µg. However both the control cationic formulation and the PAA Nanoalum formulation (FIG. 8A middle and far right groups) not only express equivalent levels of mRNA at all doses (10 µg, 1 µg, and 0.1 µg) when compared to each other, but they also demonstrate increased levels of expression (>30 fold) at the 1 µg dose compared to the unformulated mRNA and have detectable levels of expression at the 0.1 µg RNA dose demonstrating dose sparing properties of the nanoalum formulation. At 5 days post injection (FIG. 8B) the unformulated mRNA demonstrates detectable expression of LUC at the 1 µg RNA dose, albeit at lower levels, but no luciferase mRNA expression is detected at the lower doses of 1 µg and 0.1 µg. Interestingly, 5 days post injection mice receiving the control cationic formulated mRNA demonstrate no detectable expression of the mRNA at any of the doses delivered, 1 µg, 1 µg, 0.1 µg (left group and middle). However, mice receiving the PAA Nanoalum formulated mRNA (far right groups) not only expresses >10 fold higher levels of mRNA at the 10 µg dose but also demonstrate detectable expression at the 1 µg dose demonstrating dose sparing properties of the nanoalum formulation even at 5 days post-delivery of the mRNA. We then compared the expression kinetics of the animals receiving unformulated, cationic emulsion formulated, or PAA nanoalum formulated mRNA at the 1 µg dose of mRNA (FIG. 8C) at 6 hours, 24 hours and 5 days post-delivery in vivo. The data demonstrate that the animals that were immunized with mRNA formulated with nanoalum formulations have increased and relatively steady state levels of expression of the mRNA over five days (☐) compared to either unformulated mRNA (•) or the control cationic emulsion formulated mRNA (Δ) which had a rapid decline in expression.

The decline of expression of mRNA expression by day 5 when delivered by control cationic liposomes has been reported in the literature and was not unexpected, however the persistent expression of the unformulated mRNA or the nanoalum formulated mRNA was surprising and interestingly, at 5 days there still was a 10-fold dose sparing effect observed. The relative level of expression of the 10 µg dose was roughly equivalent 1 µg RNA dose for the nanoalum formulated mRNA. Without wishing to be bound by theory, we hypothesized that the nanoalum formulations of the present disclosure may stabilize the mRNA construct.

Figure 9A:
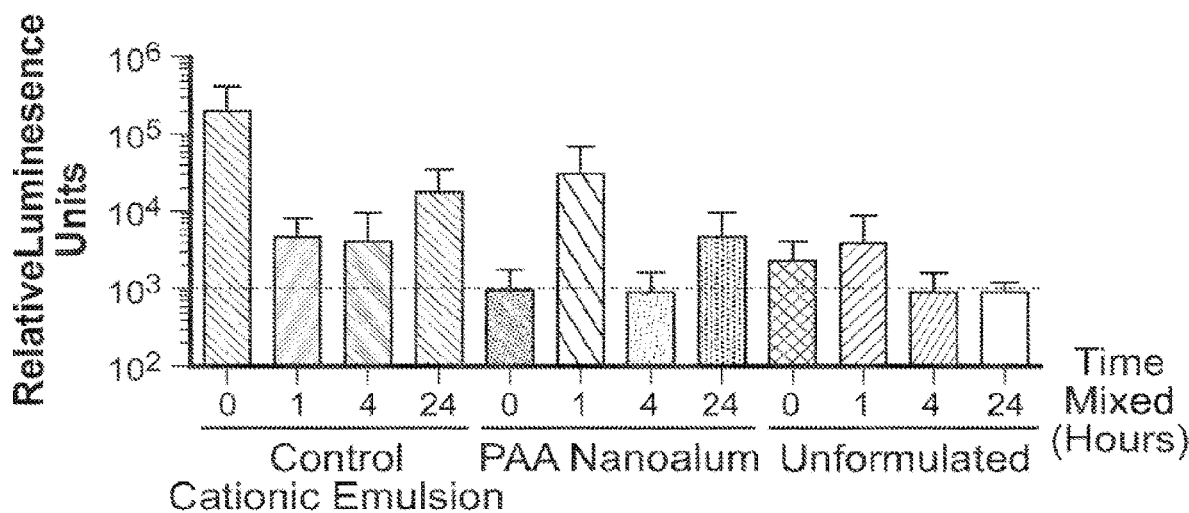
FIG. 9A-E: Nanoalum Formulations Stabilize RNA. This figure demonstrates that when nanoalum formulations (middle group, PAA Nanoalum) are admixed with RNA, stored as a single vial preparation at 4° C. for 1 hour, 4 hours, or 24 hours and subsequently used to immunize mice, the admixed formulations are capable of delivering a replicon RNA construct such that the level of luciferase expression from the replicating RNA is equivalent to or greater to formulations admixed and immediately administered at time zero when analyzed at day 1 (FIG. 9A middle group) or day 5 (FIG. 9B middle group). Unformulated RNA replicons demonstrate no detectable expression following storage for 4 or 24 hours when gene expression is measured either 24 hours or 5 days post admin strati on but do demonstrate detectable expression if administered either immediately or 1 hour after admixing. Similarly the control cationic formulation demonstrates protection of the RNA replicon when admixed and stored at 4° C. for 1, 4, or 24 hours, with gene expression measured at 1 day or 5 days after injection.
Figure 9B:
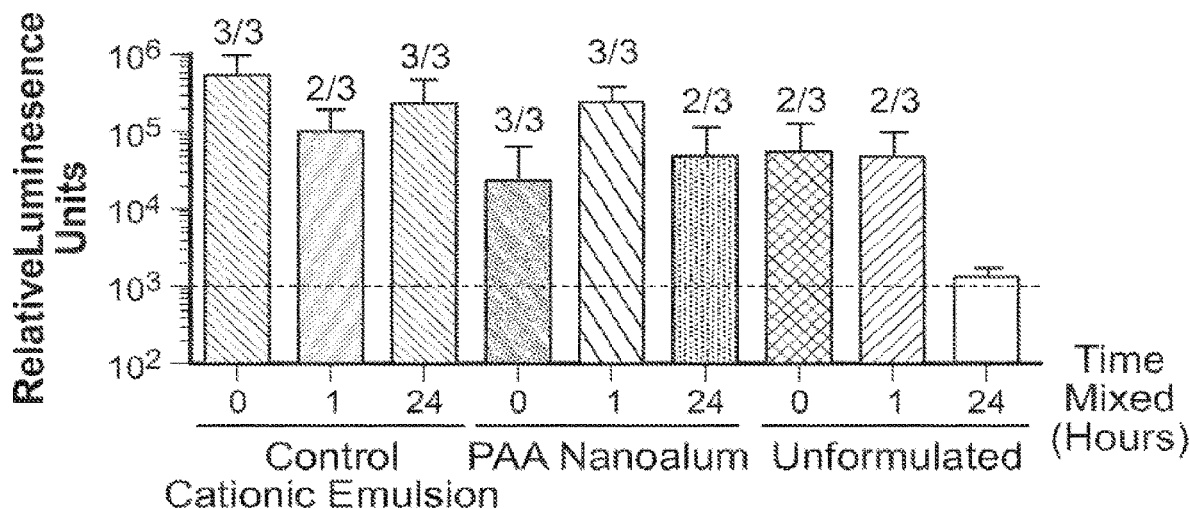
Figure 9C:
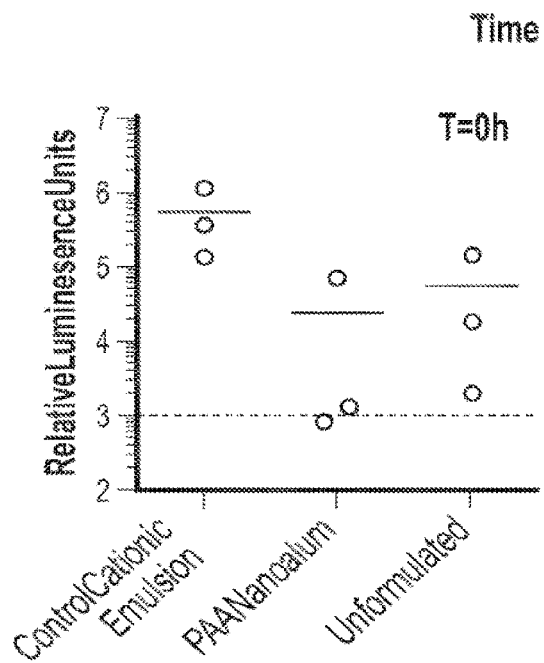
Figure 9D:
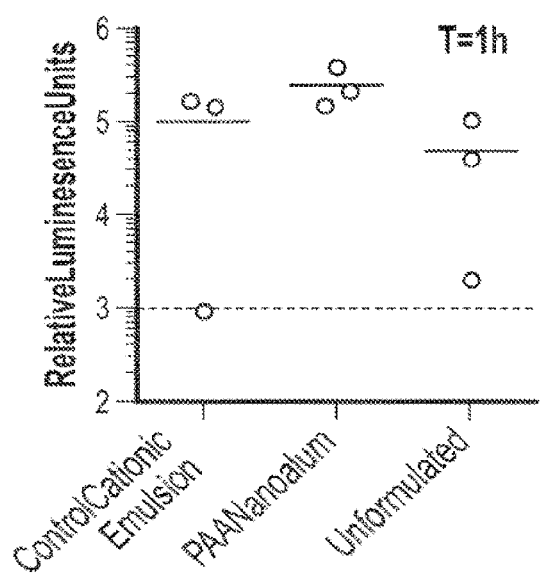
Figure 9E:
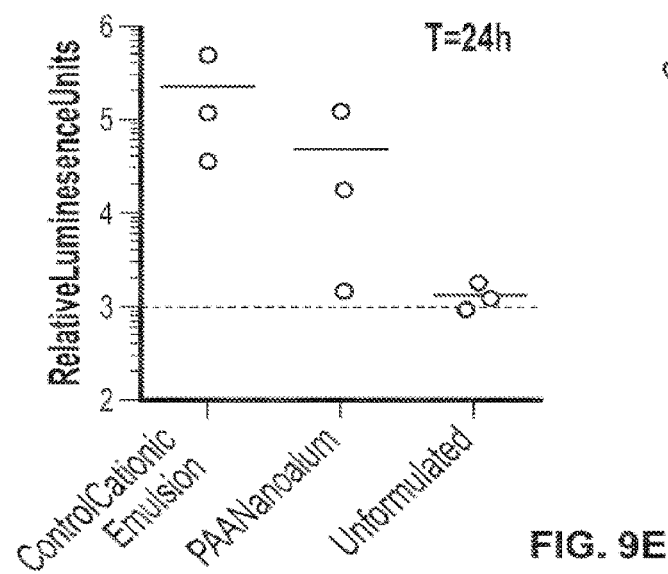

Based on the surprising stability of the in vivo expression of the mRNA formulated with the nanoalums of the present disclosure, we further examined whether the nanoalums of the present disclosure stabilized RNA in vitro. In order to test this, we admixed 1 µg of the RNA replicon with control cationic or PAA formulations and stored this admixture as a single vial preparation at 4° C. for 1 hour, 4 hours, or 24 hours. Unformulated replicon RNA stored at 4° C. for 1 hour, 4 hours, or 24 hours served as the control. These admixed single vial formulations were then used to immunize mice (3 per group) and RNA expression was assessed using an IVIS Alumina 11 imager and data quantified via Circular ROI 1 day (FIG. 9A) and 5 days (FIG. 9B) post in vivo delivery. The data demonstrate that unformulated RNA replicons had no detectable expression when stored at 4° C.

for either 4 or 24 hours post admix whether assayed 24 hours or 5 days post in vivo delivery. However detectable expression is demonstrated if the RNA replicon is administered either immediately (time 0) or 1 hour after storage at 4° C. when assessed at 24 hours or 5 days post in vivo delivery either unformulated, formulated with cationic liposomes, or formulated with the PAA nanolaum. The unformulated RNA had no detectable expression when stored at 4° C. for 4 hours or 24 hours due to the relative instability of RNA as has been reported in the literature. Comparing the data for the unformulated RNA replicon to the date for the control cationic or nanoalum formulated RNA replicon the RNA replicon when admixed and stored as a single vial at 4° C. for 1, 4, or 24 hours prior to in vivo administration demonstrated roughly equivalent expression as measured at 1 day (FIG. 9A) or 5 days (FIG. 9B). We further analyzed the data by analyzing scatter plots (FIG. 9C-E) directly comparing the data for the control cationic formulation, PAA nanoalum, and unformulated replicon RNA respectively. RNA when administered immediately after admix with the replicon RNA (T=0, 9C), administered 4 hours after admixing and storage at 4° C. (T=1 h, 9D) or admixed and stored for 24 hours (T=24 h, 9E) at 4° C. had comparable levels of expression at day 5 post administration, demonstrating that the nanoalum formulated RNA is stable when admixed as a single vial formulation at 4° C. for up to 24 hours.

Using RNA encoding reporter genes in the examples presented herein we have demonstrated that the nanoalums of the present disclosure are: (1) capable of delivery of an in vivo expressible form of an polynucleotide agent and specifically an RNA agent whether the RNA form delivered is an mRNA or expression vector RNA construct; (2) the nanoalum formulations allow for dose sparing delivery of the RNA vectors, meaning that equivalent expression of the RNA is achieved for the nanoalum formulations at doses of the RNA at least 30-300 times lower than unformulated RNA; and (3) the nanoalum formulations of the present disclosure enhance the stability of the RNA agent both in vivo and in vitro. Having developed and characterized the properties of the nanoformulation delivery of RNA, we evaluated the ability of the nanoalum formulations to deliver an RNA that results in stimulation of an immune response in a host.

In order to evaluate the ability of an RNA antigen delivered by a nanoalum formulation of the present embodiments we analyzed the immune response in mice immunized with an RNA replicon expressing the EMCH fusion polypeptide formulated with the nanoalums of the present disclosure.

Construction of the EMCH Fusion Polypeptide. The fusion polypeptide referred to as EMCH was generated by the tandem linkage of an open reading frame of polynucleotides encoding a methionine initiation codon (ATG) added to the 5' end of a fragment of the carboxyl-terminus of the putative mitochondrial HSP70 (8E or 8) polypeptide, the carboxyl-terminal fragment of the open reading frame of polynucleotides encoding the malate dehydrogenasepolypeptide, the carboxyl-terminal fragment of the cysteine proteinase B polypeptide (CpB, CPB or C), and an open reading frame of polynucleotides encoding a fragment of the amino terminus of the histone H2BN polypeptide (H2BN, h2Bn, or H). EMCH has a 2,631 polynucleotide sequence which encodes amino acids 509 to 660 of the carboxyl-terminus of the putative mitochondrial HSP70 (8E or 8) polypeptide from L. infantum polynucleotide, 460 to 1425 which encodes amino acids 1 to 322 of the carboxy terminus of the malate dehydrogenase gene from L. infantum, polynucleotide 1426 to 2295 which encodes amino acids 154 to 443 of the carboxyl-terminal fragment of the cysteine proteinase B polypeptide (B), and polynucleotides 2297 to 2631 which encodes amino acids 1 to 111 of the amino terminus of the histone H2BN (H) polypeptide from L. infantum The 877 amino acid fusion polypeptide was expressed in E. coli and purified by column chromatography. Nucleic acids components and methods of making and using are described more fully in WO2014/160985 which is incorporated herein by reference in its entirety for all purposes.

Briefly, mice were immunized with 10 µg or 0.1 µg of an alphavirus RNA replicon vector encoding the Leishmania fusion RNA polynucleotide, EMCH, either as an unformulated naked RNA control, RNA replicon admixed with control cationic liposomes or RNA replicon admixed with RNA PAA nanoalum formulations at time 0 and all groups were boosted three weeks later. Splenocytes were harvested and analyzed for recall antigen specific T cell responses as determined by intracellular cytokine staining after in vivo stimulation with the EMCH polypeptide four weeks after the last boost. Cytokine production from immunized mice splenocytes was analyzed for EMCH-specific CD44hi CD4+ memory T cells as measured by flow cytometry. Antigen stimulated spenocytes were identified by intracellular cytokine staining based on CD3 and CD4 expression and were further gated on CD44 high cells. CD44high CD4+ T cells were further stained for intracellular CD154, IFN-γ, IL2, TNFα, GM-CSF, IL-17 and IL-5 EMCH specific CD44high CD4+ T cells exhibited polyfunctional T cell responses positive for IFN-γ, TNFα and IL-2 typical of antigen specific Leishmania responses The data (10A-D) demonstrate that immunization with 100 fold lower doses of EMCH RNA, 0.1 ug, formulated with control cationic liposomes or PAA nanoalum generates approximately equivalent percentages of CD4+ CD44 high CD154, IFN-γ, IL-2 or TNFα single positive cytokine staining T cells as 10 µg of unformulated RNA. The 0.1 jig dose of unformulated RNA replicon demonstrates little or no detectable staining. Thus the nanoalum formulations of the present disclosure are capable of delivery an RNA encoding an antigen of pathogen as a vaccine formulation that stimulates an immune response in a vaccinated host.

Figure 10A:
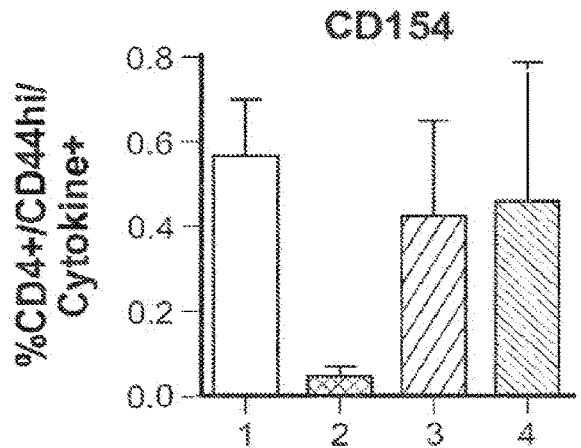
FIG. 10A-E: Mice immunized with RNA replicon expression vectors encoding a leishmaniasis fusion protein formulated with nanoalum express RNA in vivo and elicit dose sparing antigen specific immune responses. This figure demonstrates that mice immunized with an RNA replicon vector encoding a Leishmaniasis fusion polynucleotide, EMCH, generate antigen specific responses.
Figure 10B:
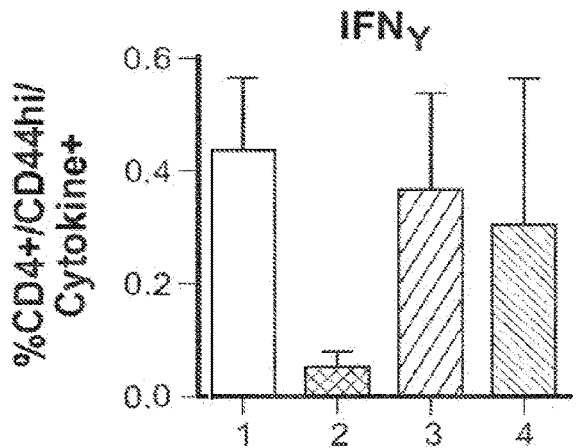
Figure 10C:
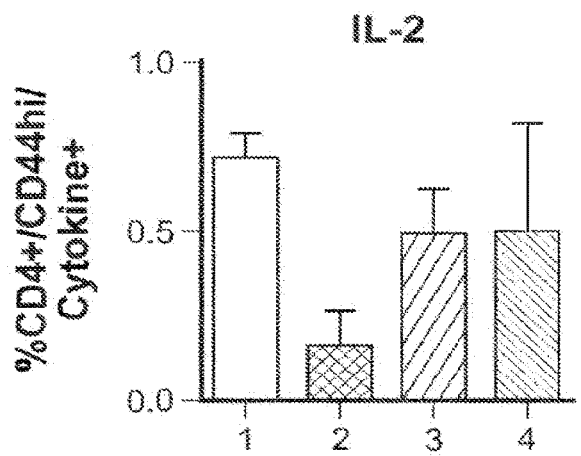
Figure 10D:
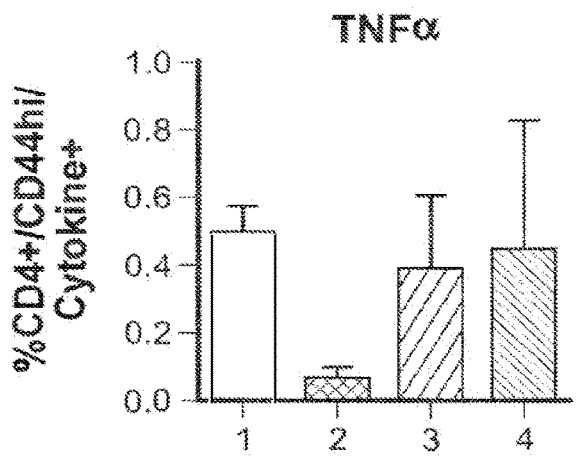
Figure 10E:
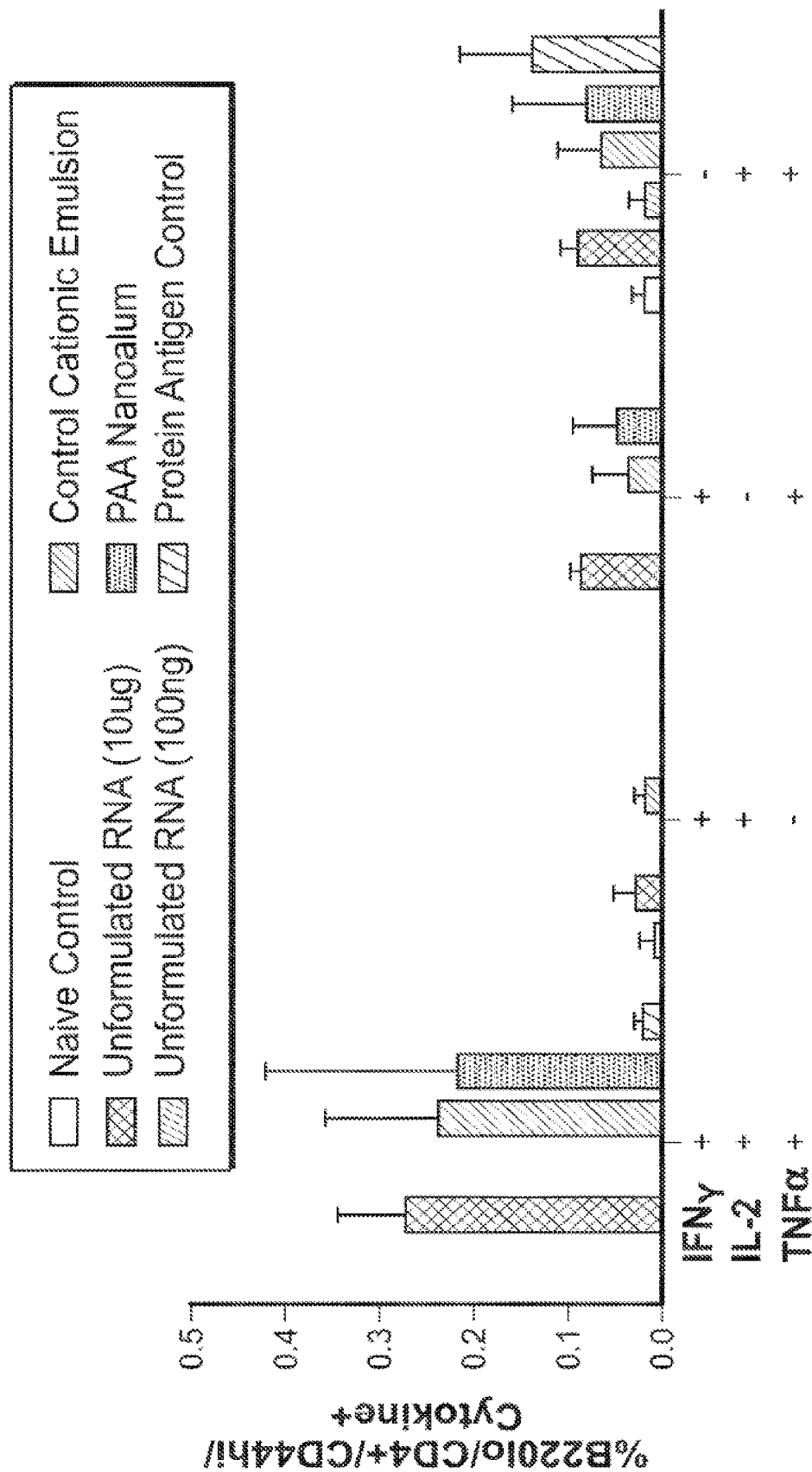

We further characterized the quality of the immune response to the Leishmania polypeptide expressed by the RNA vector when delivered formulated with the nanoalum of the present disclosure. A hallmark of a protective Leishmaniasis immune response includes the presence of polyfunctional antigen specific T cells that secrete multiple cytokines. We analyzed CD4+ CD44 high T cells for polyfunctional T cells responses. The data (FIG. 10E) demonstrate that mice immunized with 100 ng of the EMCH RNA replicon formulated with PAA nanoalum (hatched bar) or the formulated with the control cationic emulsion (diagonal slashed bar) had equivalent numbers of triple positive IFN γ, IL-2 and INFα CD4+ CD44 high T cells compared to the 10 µg unformulated RNA (solid black bar) immunized animals. Double positive cells expressing IFN-γ and IL-2 or IL-2 and TNFα were also present. The data demonstrate PAA nanoalum formulations are capable of delivering RNA that is expressed at sufficient at levels sufficient to generate relevant antigen specific immune responses characteristic of vaccines.

Example 4 Use of PEG Nanoalum Formulations (PEGs of Various Lengths) for the Delivery of Proteins or Peptides (ID93) to Stimulate an Immune Response Experiments were performed to test if the nanoalum formulations of the present disclosure could deliver a protein or polypeptide agent alone or in combination with other agents (specifically TLR agonists) to stimulate an immune response in a host.

Animal Models. Briefly, experimental animals and 6-8 week old female CB57BL/6 mice were purchased from The Jackson laboratory or Charles River and maintained in Specific Pathogen Free conditions.

ID93 is a fusion protein that incorporates four *M. tuberculosis* peptide Rv1813, Rv2620, and Rv2608, and Rv3619, produced as previously described [14].

Splenocytes were isolated from four to five animals per treatment regimen. Red blood cells were lysed using Red Blood Cell Lysis Buffer (eBioscience) and resuspended in RPMI 1640, 10% FBS. Total viable cells were enumerated using ViaCount assay with a PCA system (Guava Technologies), plated at 2×106 cells/well in 96-well plates and stimulated for 2 hours with media or ID93 (10 µg/mL) at 37° C. GolgiPlug (BD Biosciences) was added and the cells were incubated for an additional 8 hours at 37° C. Cells were washed and surface stained with fluorochrome labeled antibodies to CD4 (clone GK1.5), CD44 (clone IM7) and CD8 (clone 53-6. 7) (BioLegend and eBioscience) in the presence of anti-mouse CD16/32 for 20 minutes at 4° C. Cells were washed and permeabilized with Cytofix/Cytoperm (BD Biosciences) for 20 minutes at room temperature. Cells were washed twice with Perm/Wash (BD Biosciences) and stained intracellularly with fluorochrome labeled antibodies to CD154 (clone MR1) IFN-γ done XMG-1.2), TNF (MP6-XT22), GM-CSF (MP1-22E9), IL-17A (clone TCI 1-18H10), and IL-5 (TRFK5) (BioLegend and eBioscience) for 20 minutes at room temperature. Cells were washed and resuspended in PBS. Up to $10^6$ events were collected on a four laser LSRFortessa flow cytometer (BD Biosciences). Cells were gated as singlets>lymphocytes>CD4+ CD8->CD44hi>cytokine positive ID93-specific response frequencies were determined by subtracting the frequency of response positives of unstimulated cells from ID93 stimulated cells in matched samples.

Antibody Responses

Mouse sera were prepared by collection of retro-orbital blood into microtainer serum collection tubes (VWR International, West Chester, PA) followed by centrifugation at 10,000 rpm for 5 minutes. Each serum sample was then analyzed by antibody capture ELISA. Briefly, ELISA plates (Nunc, Rochester, NY) were coated with 2 µg/ml recombinant antigen ID93 in 0.1 M bicarbonate buffer and blocked with 1% BSA-PBS. Then, in consecutive order and following washes in PBS/Tween20, serially diluted serum samples, anti-mouse IgG1 or IgG2c-HRP (all Southern Biotech, Birmingham, AL) and ABTS-$H_2O_2$ (Kirkegaard and Perry Laboratories, Gaithersburg, MD) were added to the plates. Plates were analyzed at 405 nm (ELX808, Bio-Tek Instruments Inc, Winooski. VT). Midpoint titers were calculated using Prism software (GraphPad Software, Inc.) to determine the sigmoidal dose-response curve using the least squares fit method.

Figure 11B:
FIG. 11A-B demonstrate that mice immunized with nanoalum formulations having nanoalum particle sizes of 400 nm, 130 nm or 75 nm adsorbed to the TB fusion peptide ID93 elicit antigen specific immune responses.
Figure 11A:
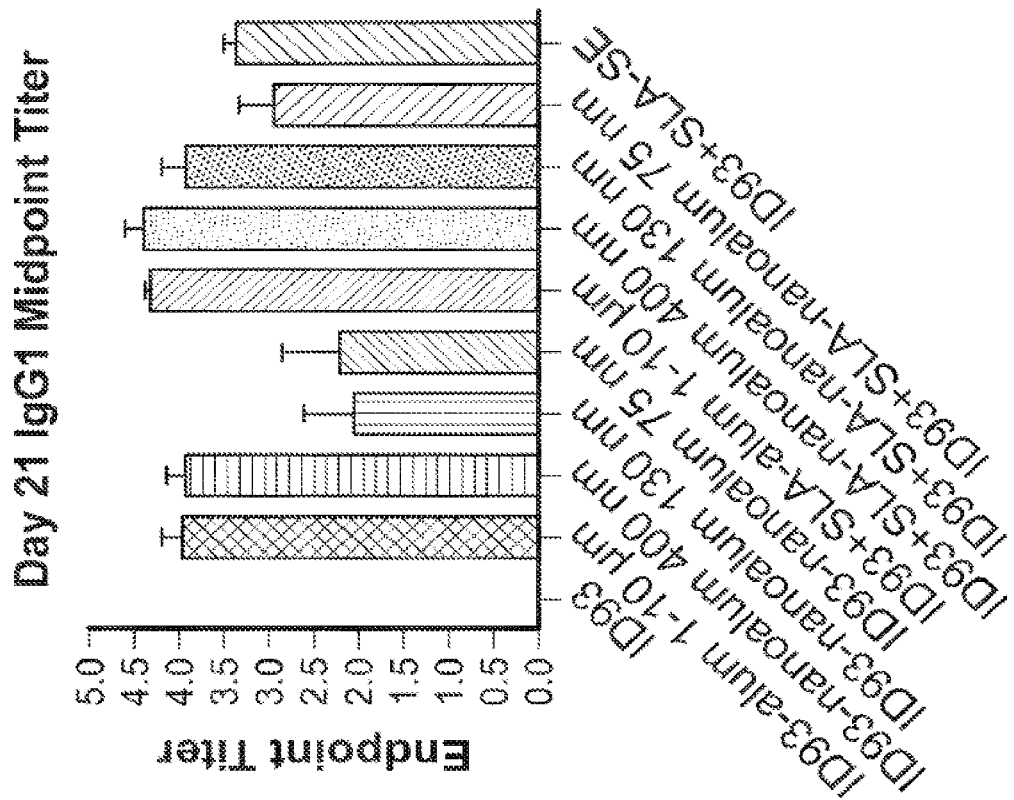

Previously published data in the *Mycobacterium tuberculosis* model demonstrated that mice immunized with fusion polypeptide ID93 formulated with GLA/SE induced greater ID-93 specific IgG2c responses, indicative of a Th1 biased response (Baldwin 2012). Published data also indicates the Alum formulations, however, have generally induce a greater Th2 response as demonstrated by greater IgG1 antibody responses. We evaluated whether changing the average particle size of the nanoalum formulation would affect the quality of the immune response generated to the ID93 fusion polypeptide. In order to evaluate this, animals were immunized on day zero intramuscularly in the quadriceps with 0.5 µgID93 admixed with 100 µg micron alum (e.g., unprocessed alum that is commercially available) which served as the control formulation or 0.5 µg ID93 admixed with 100 ng PEG nanoalum formulations (PEG 5000-DSPE as the sizing agent milled such that the resulting formulations have average particle sizes of 400 nm, 130 nm, or 75 nm) plus or minus 5 µg of the TLR4 agonist SLA on day zero. On day 21 post immunization animals were bled and sera were collected and analyzed for ID93 specific antibody responses as described. The antibody midpoint titers for ID93 specific IgG1 at day 21 (FIG. 11A) and for IgG2c (FIG. 11B) demonstrate that animals immunized with ID93 admixed with the SLA-SE formulation generate both ID93 specific IgG1 and IgG2c antibody titers with a slight increase in the IgG2c titer indicative of a Th1 response as we have previously described. Immunization of mice with the ID93 fusion polypeptide alone did not result in measure able IgG1 or IgG2c antibody titers as expected. Immunization with alum formulations having particle sizes of 1-10 microns demonstrated a pronounced bias toward a Th2 response as indicated by high IgG1 antibody titers and low titer IgG2c titers as predicted in the literature. These controls were compared to PEG nanoalum formulations comprising PEG-5000 DSPE as the sizing agent milled or sized by varying the methods (silverson mixing at 5000 rpm for 5 minutes, microfluidization at 10 k PSI for one passage or 10 passages at 30 k PSI) as described in Example 1 to produce nanoalums of 400 nm, 130 nm, or 75 nm particle sizes respectively. The data demonstrate (FIG. 11A) that the 400 nm PEG nanoalum formulations induce the same endpoint IgG1 titer as the unprocessed aluminum formulations. The 130 nm and 75 nm particle sized PEG nanoalum formulations also produce a high day 21 IgG1 midpoint filers although reduced roughly in half compared to the alum or the 400 nm particle size PEG nanoalum. The data demonstrate that none of the PEG nanoalum formulations tested resulted in measureable IgG2c ID93 antibody titers in immunized mice. In order to determine if addition of the TLR4 agonist to the admixed nanoalum formulation could bias the response to produce a Th1 response as measure by IgG2c, mice were also immunized with the TLR 4 agonist, SLA plus the ID93 antigen and the PEG nanoalum formulations. The data demonstrate that the admixing the TLR4 agonist SLA with the alum formulation or the 400 nm particle size PEG nanoalum formulation had a negligible effect on the midpoint titer of ID93 specific IgG1 responses, but admixing SLA with the 130 nm or 75 nm particle sized PEG nanoalums trended toward increases in the midpoint ID93 specific IgG1 responses. Similarly the data presented in FIG. 11B analyzing ID93 antigen specific IgG2c day 21 midpoint titers demonstrated ID93 IgG2c titers are induced when SLA is added to the 400 nm, 130 nm, or 75 nm particle size PEG nanoalum formulations compared to no detectable titers in animals immunized with ID93/PEG nanoalums in the absence of SLA. The data indicate that PEG nanoalums are capable of eliciting a Th2 biased immune response, but PEG nanoalum formulations with particle sizes of 130 nm or less have ID93 IgG1 titers that are reduced roughly in half compared to alum or 400 nm PEG nanoalum. Interestingly, addition of a TLR 4 agonist, SLA, nearly restored magnitude of the Th2 biased response to that of the traditional alum formulation. In addition, while no ID93 specific IgG2c antibody titers were detected for mice immunized with the ED93PEG nanoalums, addition of the TLR4 agonist, SLA, to the ID93/PEG nanoalum vaccine compositions did result in production of IgG2c, indicating some biasing of the response to Th1 by SLA.

Mice immunized with PEG nanoalum formulations comprising either pegylated phospholipid sizing agents with differing PEG lengths or the same PEG length linked to Phospholipids of Differing Acyl Chain Lengths and Admixed with TB Fusion Peptide ID93 Plus the TLR4 agonist SLA elicit antigen specific immune responses. Table 5 presents a table of the experimental groups comparing adsorption of 0.5 µg of the fusion proton ID93 to 100 µg of traditional 1-10 µm particle sized alum formulations bench mixed with PEG-5000 DSPE (without milling or processing) plus 5 µg of the TLR4 agonist SLA with microfluidized nanoalum formulations comprising the sizing agent PEG-DSPE having differing PEG lengths of 5000, 2000, or 750 adsorbed to 0.5 µg of the fusion protein ID93 plus 5 µg of SLA and nanoalum formulations with a pegylated phospholipid sizing agent having a defined PEG length of 2000 and phospholipids of differing acyl chain lengths of 18 carbons (DSPE), 16 carbons (DPPE) and 14 carbons (DMPE).

TABLE 5

| Group | Vaccine | PEG length | Acyl chain Length | Alum Size |
|---|---|---|---|---|
| 1 | ID93 | — | — | — |
| 2 | ID93-SLA-alum/PEG | 5000 | DSPE 18C | 1-10 µm |
| 3 | ID93-SLA-PEG-Nanoalum | 5000 | DSPE 18C | ~70 nm |
| 4 | ID93-SLA-PEG Nanoalum | 2000 | DSPE 18C | ~70 nm |
| 5 | ID93-SLA-PEG Nanoalum | 750 | DSPE 18C | ~70 nm |
| 6 | ID93-SLA-PEG Nanoalum | 2000 | DPPE 16C | ~70 nm |
| 7 | ID93-SLA-Nanoalum | 2000 | DMPE 14C | ~70 nm |
| 8 | ID93 + SLA-alum | | | 1-10 µm |

Figures 12A, 12B:
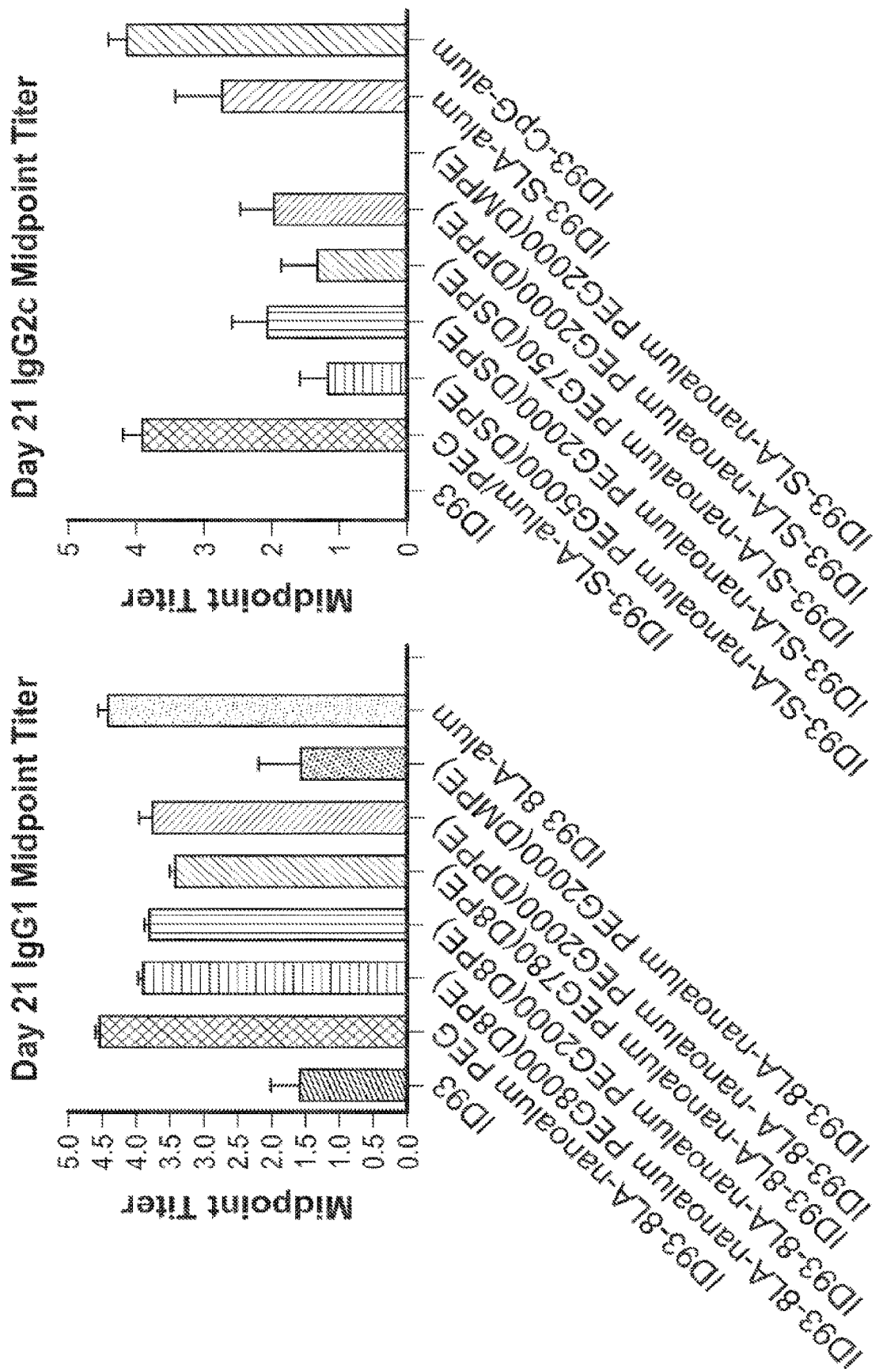
Figure 12C:
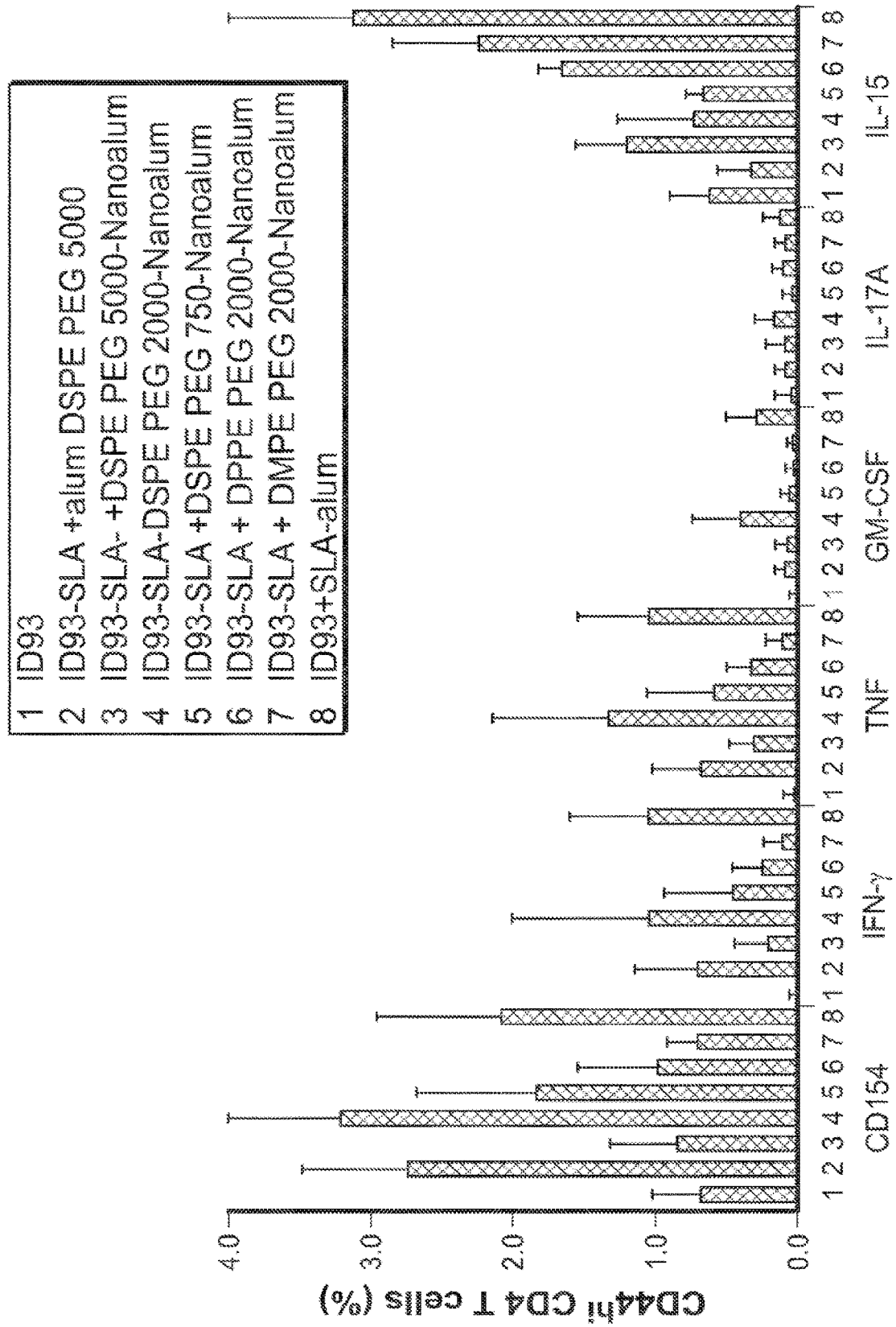

Mice immunized with a dose of 5 µg of the TLR agonist SLA and 0.5 µg of the ID93 fusion protein adsorbed to 100 ug PEG nanoalum formulations (PEG-DSPE as the sizing agent) with PEG lengths of 5000, 2000, or 750 and particle sizes of approximately 70 nm elicit ID93 antigen specific IgG1 antibody titers measured as Midpoint titers at day 21. FIG. 12A demonstrates that equivalent IgG1 titers are elicited in mice immunized with traditional 1-10 µm particle sized alum formulations and 70 nm nanalum formulations comprising the sizing agent PEG-DSPE with PEG lengths of 5000, 2000 or 750 or PEG lengths of 2000 linked to phospholipid acyl chain lengths of 18(DSPE) or 16 (DPPE) carbons. Nanoalum formulations having a phospholipid with an acyl chain length of 14 carbons (DMPE) and a PEG length of 2000 have IgG1 titers reduced by roughly half compared to the other nanoalum formulations. FIG. 12B demonstrates that a dose of 100 ug of a 70 nm particle sized nanolaum formulation comprising the sizing agent PEG-DSPE with PEG lengths of 5000, 2000 or 750 or PEG lengths of 2000 linked to phospholipid acyl chain lengths of 18(DSPE) or 16 (DPPE) carbons adsorbed to 0.5 µgID93 plus 5 µg of the TLR4 agonist, SLA, elicit antigen specific IgG2c antibody titers indicative of a Th1 bias although the response is roughly half that seen with an alum formulation of 1-10 µm particle sizes. Nanoalum formulations having a phospholipid with an acyl chain length of 14 carbons (DMPE) and a PEG length of 2000 do not demonstrate any appreciable ID93 IgG2c. FIG. 12C demonstrates that ID93 nanoalum formulations induce antigen-specific CD4+ T cells. Cytokine production from immunized mice was analyzed for ID93-specific CD44hi CD4+ memory T cells as measured by flow cytometry. Splenocytes from vaccinated mice stimulated with ID93 for 12 hours in the presence of GolgiStop and ID93-stimulated splenocytes were identified by intracellular cytokine staining based on CD3 and CD4 expression and were further gated on CD44high cells. CD44high CD4+ Tcells were further stained for intracellular CD154, IFN-γ, TNF, GM-CSF, IL-17 and IL-5. ID93 specific CD44high CD4+ T cells exhibited polyfunctional T cell responses positive for TNFα and IL-5 typical of antigen specific ID93 responses, demonstrating that these nanoalums can be an effective vehicle for the TLR4 agonist SLA to induce Th1 immunity to the ID93 antigen.

Example 4, Generation of Chitosan-, Dextran- and Poly(Allylamine)-Nanoalum Formulations Aluminum-containing adjuvants have been administered in humans and animals since the mid-1920s. The term alum is used broadly to generally classify any aluminum-based adjuvant used in vaccines, but chemically these are primarily aluminum oxyhydroxide (AlO(OH)) or aluminum phosphate (AlPO$_4$ also referred to as Al(OH)$_x$(PO$_4$)$_y$). AlO(OH) is poorly crystalline as evidenced from its x-ray diffraction (XRD) pattern, the crystal structure is pseudoboehmite, which is one of the many metastable phases of the stable corundum (α-Al$_2$O$_3$) phase. The surface of AlO(OH) is cationic and thus most suitable for adsorption of anionic antigens. TEM imaging shows fibrous nanoparticles with calculated average dimensions of 4.5×2.2×10 nm, which form aggregates with a broad size distribution from 5-10 microns in suspension. Aluminum phosphate, contrary to its name consists both phosphate and hydroxide counterions in non-stoichiometric amounts, has a net negative (anionic) surface charge and thus most suitable for adsorption of cationic antigens. Unlike AlO(OH), aluminum phosphate is anhydrous to x-rays and consists of ~50 nm disc-shaped particles that form loose aggregates of approximately 4 µm in median diameter. Described herein are examples of aluminum-based nanoparticle adjuvants (nanoalum) manufactured using commercially available micron-sized alum (e.g. Alhydrogel® or AdjuPhos®) as starting material and microfluidizing it in the presence of stabilizing agents Nanoalum-Chitosan using AdjuPhos® (Al(OH)$_x$(PO$_4$)$_y$) adjuvant: The following describes a general method to synthesize nanoalum using AdjuPhos® as the alum precursor and a low molecular weight chitosan (50,000-190,000 Da based on viscosity of 20-300 cP of 1 wt % solution in 1% acetic acid at 25° C.) with 75-85% degree of deacetylation (DD) as the stabilizing agent.

Materials

| Name | Vendor | Lot# | mw [g/mol] | Stock conc (if app) |
|---|---|---|---|---|
| Adju-Phos | Brenntag | 9255 | n/a | 5 mg Al/ml |
| Chitosan (low mw) | Sigma | STBF8219V | 50,000-190,000 | n/a |

Figure 13B:
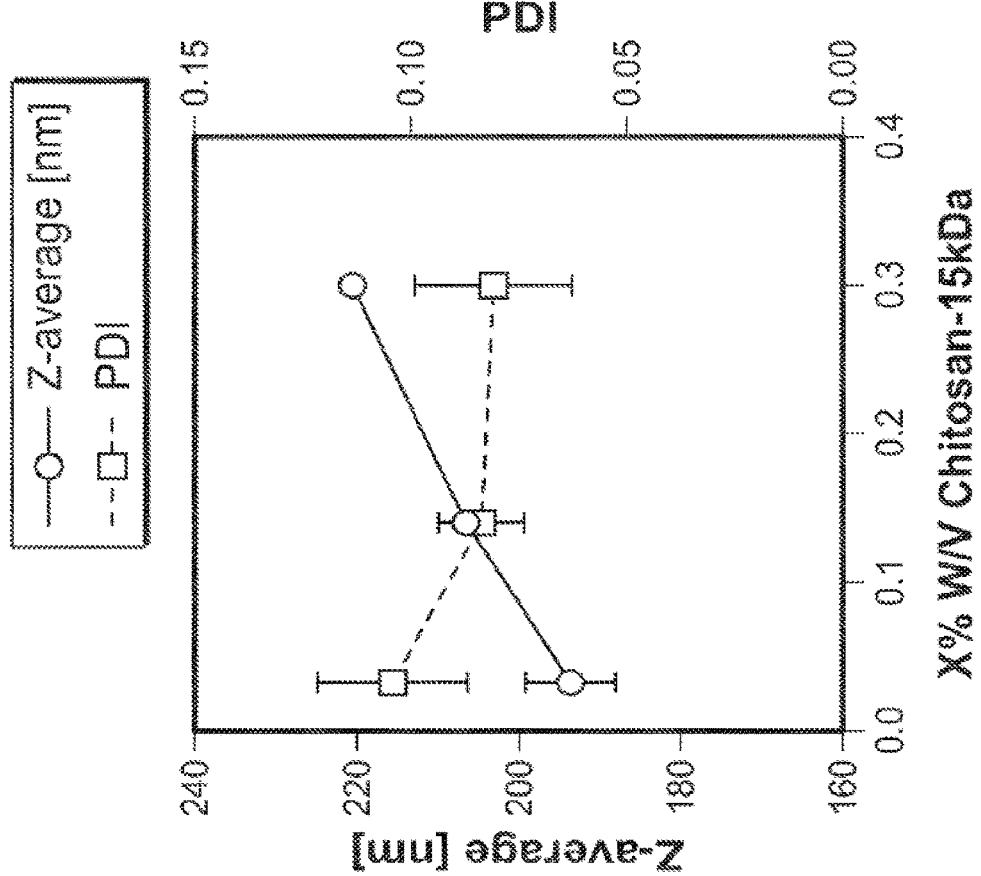
FIG. 13A-B.
Figure 13A:
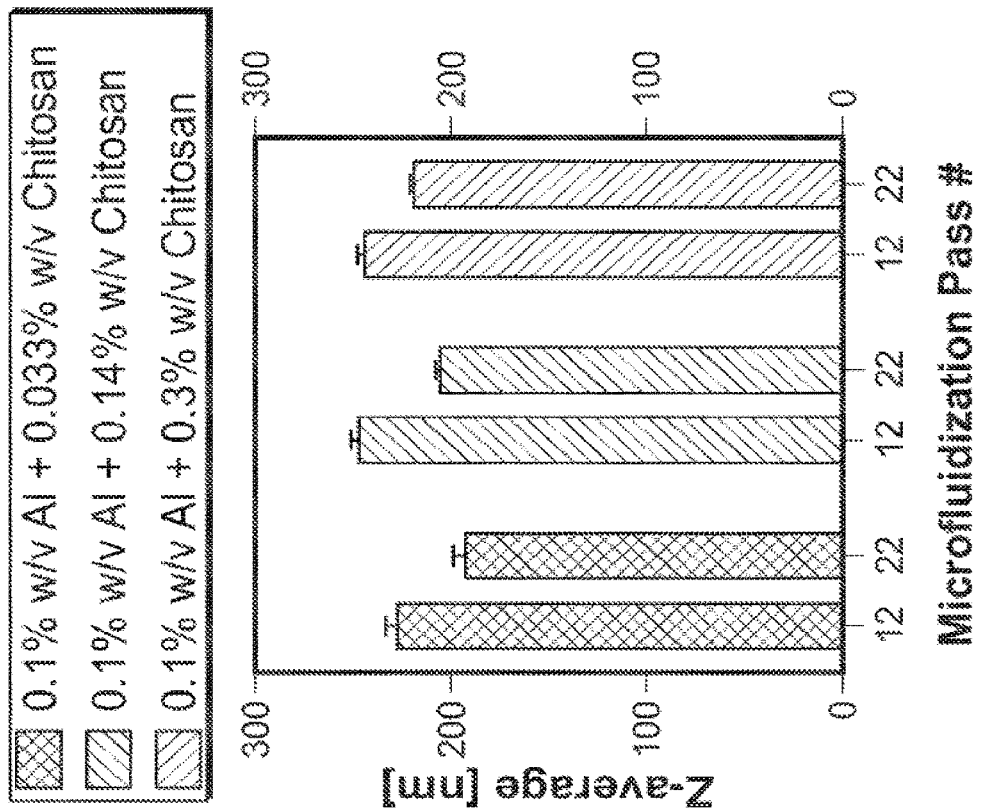

AdjuPhos® adjuvant concentration (10 ml at 5 mgAl/ml; 50 mg Al) was kept constant and stabilized with varying amounts of chitosan. Prior to mixing, a predetermined of chitosan was dissolved in 40 ml of mildly acidic 0.12 M sodium acetate/0.02 M acetic acid buffer, pH=5.4. After dissolving completely, the chitosan solution (40 ml) was mixed with 10 ml of AdjuPhos® (50 mg aluminum), mixed for 5 minutes in silverson high shear mixer at 5,000 rpm and then microfluidized at 30,000 psi for 22 discrete passes in LM20 high shear microfluidizer (Microfluidics). The microfluidized material was visually turbid but translucent. Composition of various Adjuphos®-derived nanoalums stabilized with chitosan is provided in Table 6 below. The hydrodynamic diameter reduced with number of passes as shown in FIG. 13A. For the same homogenization process, the hydrodynamic diameter trended lower with increasing chitosan fraction (13B). On average, the zeta potential of nanoalum-chitosan formulations was +20 mV.

TABLE 6

Compositions of nanoalums manufactured using Adjuphos ® as starting material and low molecular weight chitosan (~120,000 Da, minimum 85% DD) as stabilizing agent.

| Lot# if applicable | QG777 | | | QG778 | |
|---|---|---|---|---|---|
| Adju-Phos [% w/v Al] | 0.10% | 0.10% | 0.10% | 0.10% | 0.10% |
| chitosan (low mw) [% w/v] | 0.07% | 0.30% | 0.59% | 0.033% | 0.007% |
| Final volume [ml] | 50 | 50 | 50 | 50 | 50 |

Nanoalum-Dextran using Alhydrogel® (AlO(OH)) adjuvant—The following describes a general method to synthesize nanoalum using Alhydrogel® as the alum precursor and dextran sulfate (40,000 Da) as the stabilizing agent.

Materials

| Name | Vendor | Lot# | mw [g/mol] | Stock conc (if app) |
|---|---|---|---|---|
| Alhydrogel 85 | Brenntag | 85561 | n/a | 10 mg Al/ml |
| dextran sulfate (40 kDa) | Alfa Aesar | X18C022 | 40000 | n/a |

Figure 14B:
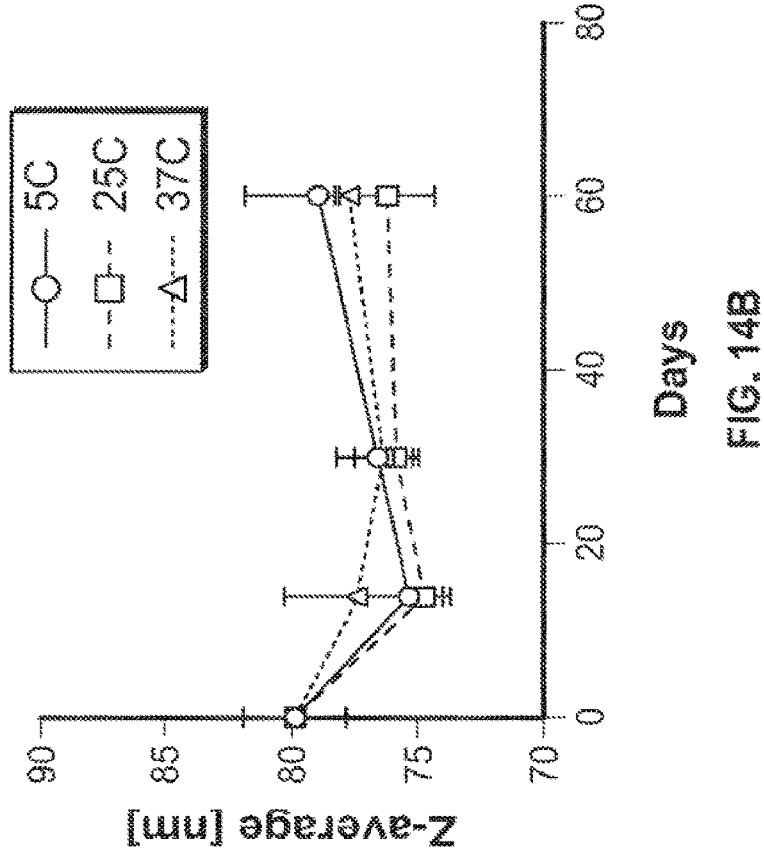
FIG. 14B displays the particle size stability data for nanolum-dextran lot QG774 (0.2% w/v aluminum+0.22% dextran sulfate-40 kDa) stored at 5° C., 25° C. and 37° C.
Figure 14A:
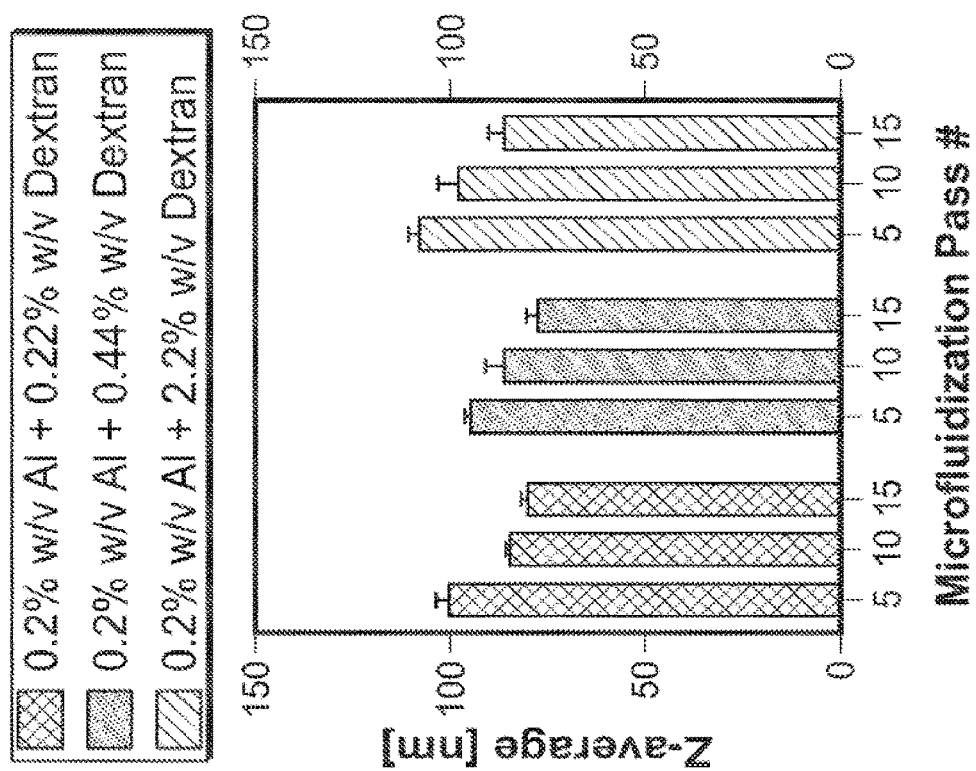
FIG. 14A provides the particle size of Alhydrogel®-derived nanoalum (0.2% w/v Al) stabilized with 40 kDa dextran sulfate. Microfluidization done at 30,000 psi.

Alhydrogel® adjuvant concentration (10 ml at 10 mgAl/ml; 100 mg aluminum) was kept constant and stabilized with varying amounts of dextran sulfate. Prior to mixing, a predetermined of dextran sulfate was dissolved in 40 ml of DI water. 10 ml of Alhydrogel® (100 mg Al) was added to 40 ml of dextran sulfate solution, mixed for 5 minutes in silverson high shear mixer at 5,000 rpm and then microfluidized at 30,000 psi for 15 discrete passes in LM20 high shear microfluidizer (Microfluidics). The microfluidized material was clear to translucent and sterile filtered with 200 nm PES membrane. Composition of various Alhydrogel®-derived nanoalums stabilized with dextran sulfate is provided in Table 7 below. The hydrodynamic diameter reduced with number of passes as shown in FIG. 14A. On average, the zeta potential of nanoalum-dextran formulations was −40 mV. Particle stability data available at the time of this report show no significant change in size of nanoalum-dextran (lot QG774 shown as example) up to 3 months after manufacturing date (FIG. 14B).

TABLE 7

Composition of nanoalums manufactured using Alhydrogel as starting alum material and dextran sulfate (40 kDa) as stabilizing agent

| Lot# if applicable | QG772 | QG773 | QG774 |
|---|---|---|---|
| Alhydrogel ® [% w/v Al] | 0.20% | 0.20% | 0.20% |
| Dextran sulfate [% w/v] | 0.437% | 2.186% | 0.219% |
| Final volume [ml] | 50 | 50 | 50 |

Nanoalum-Chitosan using Alhydrogel® (AlO(OH)) adjuvant. The following describes a general method to synthesize nanoalum using Alhydrogel® as the alum precursor and chitosan (15,000 Da, minimum 85% DD) as the stabilizing agent.

Materials

| Name | Vendor | Lot# | [g/mol] |
|---|---|---|---|
| Alhydrogel ® 85 | Brenntag | 85561 | na |
| Chitosan-15000 | Polysciences | 697180 | 15000 |
| 10× PBS | Gibco | 1836480 | na |
| Acetic acid, glacial | Fischer chemical | 162521 | 60.05 |

Figures 15A, 15B:
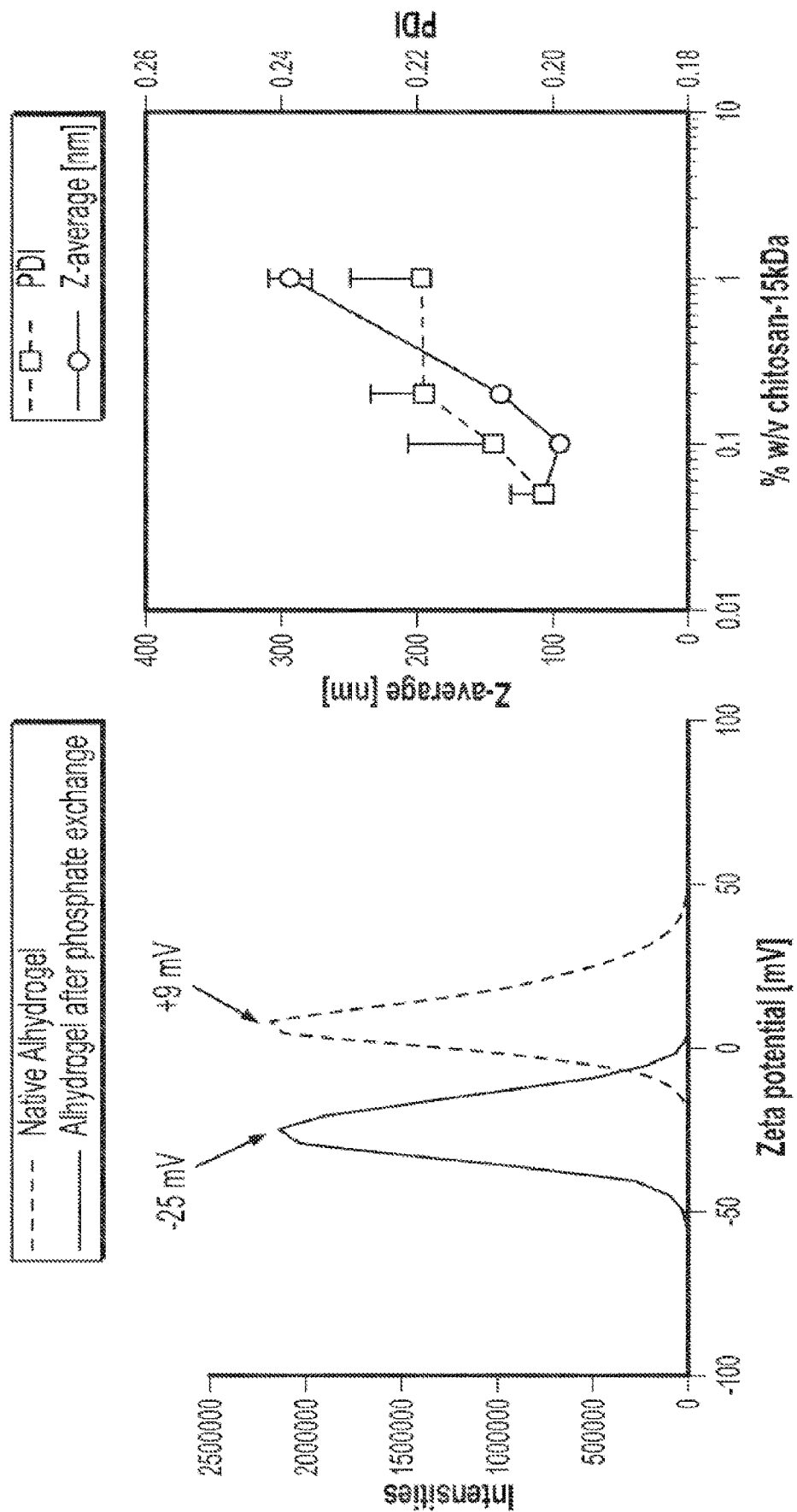
FIG. 15A-B.

Native alhydrogel (AlO(OH)) has a cationic surface charge and thus electrostatically repels chitosan, which is also cationic. In order to adsorb chitosan to Alhydrogel®, the latter must undergo surface modification via phosphate ligand exchange. For phosphate exchange, Alhydrogel® (10 mgAl/ml) was mixed with 10×PBS at 1:2 volume ratio and allowed to react for 24-48 hours at 37 C on an orbital shaker. Phosphate exchanged Alhydrogel® (PE-Alhydrogel®) was centrifuged at 2500 rpm for 15 minutes and the clear supernatant decanted. The pelleted PE-Alhydrogel® was then dispersed in DI water and the centrifugation-decanting step was repeated 3 times to wash out the phosphate buffer. The final washed PE-Alhydrogel® pellet was dispersed in DI water at a concentration of 10 mgAl/ml and stored at room temperature. Zeta potential measurement of Alhydrogel® before and after phosphate exchange confirmed that surface charge was successfully transformed from cationic to anionic (FIG. 15A). A 2% w/v chitosan solution in 1% v/v acetic acid was prepared as a stock solution for mixing with PE-Alhydrogel®. 10 ml of PE-Alhydrogel® (100 mg Al) was mixed with varying amounts of chitosan prepared by diluting the 2% stock chitosan solution with DI water. Example mixing conditions are listed in Table 8.

TABLE 8

Examples of PE-Alhydrogel ® and chitosan mixing conditions.

| Alhydrogel (lot# 85561) [ml] | Chitosan-15 kDa volume from 2% w/v stock [ml] | MilliQ [ml] | Total [ml] |
|---|---|---|---|
| 10 | 1.25 | 38.75 | 50 |
| 10 | 2.5 | 37.5 | 50 |
| 10 | 25 | 15 | 50 |
| 10 | 2.5 | 37.5 | 50 |

Each 50 ml of PE-Alhydrogel® and chitosan mixture was homogenized with silverson high shear mixer at 5,000 rpm for 5 minutes, then microfluidized at 30,000 psi in continuous mode for 5 minutes at 110 ml/min using the M110P microfluidizer (Microfluidics). The microfluidized material was white opalescent and nearly transparent. Composition of example lots synthesized is provided in Table 9. Particle size of pre-filtered nanoalum-chitosan material from DLS is shown in FIG. 15B. In general, the Z-average diameter was positively related to the amount of chitosan used. Formulations were filtered with 200 nm PES membrane, when filtration was possible, and stored at 4° C. On average, zeta potential of nanoalum-chitosan formulations was +20 mV

TABLE 9

Compositions of Alhydrogel ®-derived nanoalum stabilized with chitosan (15 kDa, minimum 85% DD).

| Name | Lot Size [ml] | Aluminum [mg/ml] | Chitosan-15 kDa [mg/ml] | Acetic acid [mM] |
|---|---|---|---|---|
| QG851 | 50 | 2 | 1 | 8.7 |
| QG850 | 50 | 2 | 0.5 | 4.4 |
| QG849 | 50 | 2 | 1 | 8.7 |
| QG845 | 50 | 2 | 2 | 17.5 |

The z-average hydrodynamic diameter increases over time but, depending on the amount of chitosan used, plateaus at around 300-500 nm. Secondly, the rate of size increase is temperature dependent—size increases more rapidly at higher temperatures—suggesting that size increase is endothermic and potentially driven by an increase in entropy.

Nanoalum-poly(allylamine) using Alhydrogel® (AlO(OH) adjuvant—The following describes a general method to synthesize nanoalum using Alhydrogel® as the alum precursor and poly(allylamine) (15,000 Da) as the stabilizing agent.

Materials

| Name | Supplier | Lot# | Conc. |
|---|---|---|---|
| Alhydrogel ® 85 | Brenntag | 85595 | 10 mg/ml |
| Poly(allylamine) | Polysciences | 698574 | 15% w/v |
| PBS | Gibco | 1836480 | 10× |

Native Alhydrogel® (AlO(OH)) has a cationic surface charge and thus electrostatically repels poly(allylamine), which is also cationic. In order to adsorb poly(allylamine) to Alhydrogel®, the latter must undergo surface modification via phosphate ligand exchange. For phosphate exchange. Alhydrogel® (10 mgAl/ml) was mixed with 10×PBS at 1:2 volume ratio and allowed to react for 24-48 hours at 37 C on an orbital shaker. Phosphate exchanged Alhydrogel® (PE-Alhydrogel®) was centrifuged at 2500 rpm for 15 minutes and the clear supernatant decanted. The pelleted PE-Alhydrogel® was then dispersed in DI water and the centrifugation-decanting step was repeated 3 times to wash out the phosphate buffer. The final washed PE-alhydrogel pellet was dispersed in DI water at a concentration of 10 mgAl/ml and stored at room temperature. Zeta potential measurement of Alhydrogel® before and after phosphate exchange confirmed that surface charge was successfully transformed from cationic to anionic. To synthesize nanoalum stabilized with poly(allylamine), 10 ml of PE-alhydrogel (100 mg Al) was mixed with varying amounts of 15% w/v poly(allylamine); example mixing ratios are summarized in Table 10. Since the free base form of poly(allylamine) was used, pH of the PE-alhydrogel and poly(allylamine) mixture was between 8 and 11, and thus required adjustment to 7 using 6M HCl.

TABLE 10

Examples of mixing ratios used to prepare Alhydrogel ®-derived nanoalum stabilized with poly(allylamine).

| PE-alum [ml] | Poly(allylamine); volume from 15% w/v stock [ml] | DI water [ml] | Total [ml] |
|---|---|---|---|
| 10 | 0.33 | 39.67 | 50 |
| 10 | 0.67 | 39.33 | 50 |
| 10 | 3.33 | 36.67 | 50 |

Figure 16:
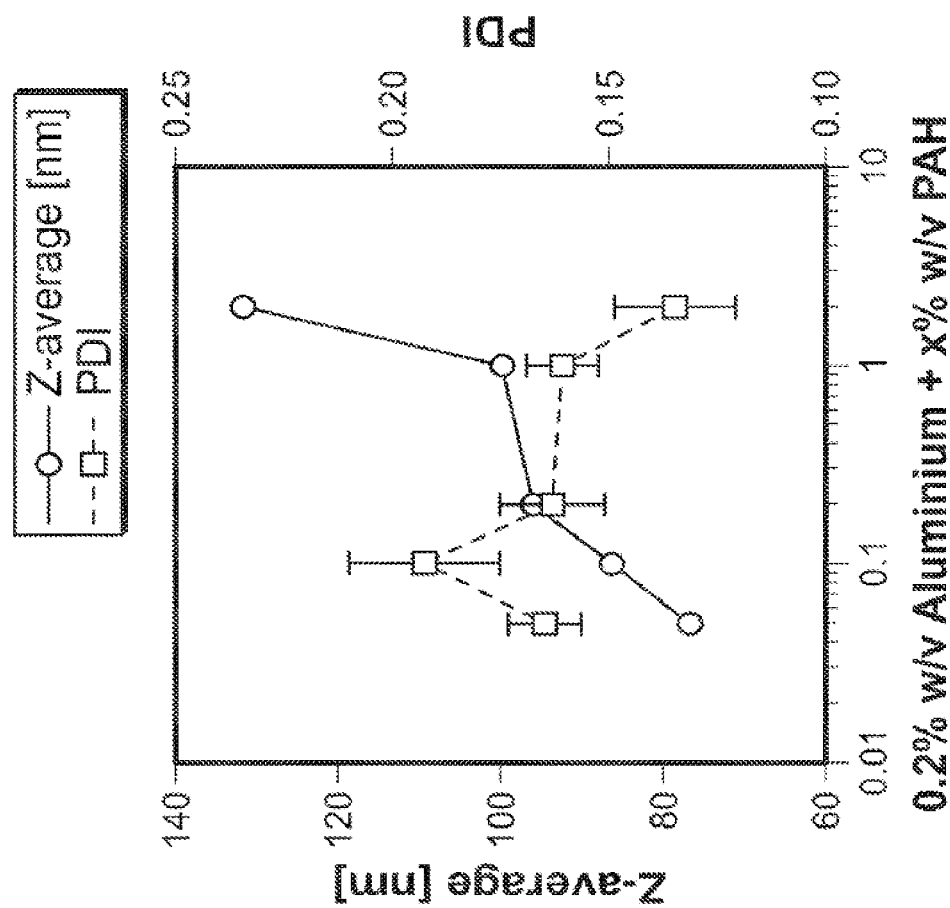
FIG. 16 demonstrates the effect of poly(allylamine) (PAH) fraction on the particle size and size distribution of nanoalum synthesized from PE-Alhydrogel®.

To produce stable nanoalum, the PE-Alhydrogel® and poly(allylamine) mixture was mixed for 5 minutes using the Silverson high shear mixer at 5,000 rpm, and then microfluidized at 30,000 psi for 5 minutes at 110 ml/min using the M110P microfluidizer (Microfluidics). The microfluidized material was nearly transparent and was sterile filtered with 200 nm PES membrane. Nanoalum particle size, shown in FIG. 16 increased with poly(allylamine) content. On average, zeta potential of nanoalum-poly(allylamine) formulations was around +20 mV. Composition of example nanoalum-poly(allylamine) formulations prepared is provided in Table 11.

TABLE 11

Examples of Alhydrogel ®-derived nanoalum formulations stabilized with poly(allylamine)

| Lot# | Lot Size [ml] | Aluminum [mg/ml] | Poly(allylamine) [mg/ml] |
|---|---|---|---|
| QG861 | 50 | 2 | 0.5 |
| QG860 | 50 | 2 | 1 |
| QG859 | 50 | 2 | 2 |
| QG858 | 50 | 2 | 10 |
| QG854 | 50 | 2 | 20 |

Nanoalum-poly(allylamine) for formulating RNA-based vaccines—To evaluate compatibility of nanoalum-poly(allylamine) to complex with RNA we mixed 1 μg of a 10 kb self-replicating RNA, encoding a Zika antigen, with diluted nanoalum-poly(allylamine) formulations containing 1 mg/ml (lot QG860), 2 mg/ml (lot QG859) or 20 mg/ml (lot QG854) poly(allylamine). The nanoalum complexed RNA samples, along with naked RNA controls, were assayed on a gel retardation assay (GRA) to evaluate each formulation's ability to bind RNA and loading capacity QG859 (2 mg/ml poly(allylamine) undiluted) bound 100% of RNA at 1/200 dilution (0.01 mg/ml poly(allylamine)). Similarly, QG860 (1 mg/ml poly(allylamine) undiluted) bound 100% of RNA at 1/100 dilution (0.01 mg/ml poly(allylamine)). Both formulations showed similar binding characteristics that correlated with the amount of poly(allylamine). On the other hand, QG854 (20 mg/ml poly(allylamine) undiluted) bound nearly 100% RNA even at 1/4000 dilution (0.005 mg/ml poly(allylamine)).

REFERENCES

1. Shah R R, Dodd S. Schaefer M Ugozzoli M, Singh M, Otten G R, Amiji M M, O'Hagan D T, Brito L A. The Development of Self-Emulsifying Oil-in-Water Emulsion Adjuvant and an Evaluation of the Impact of Droplet Size on Performance. Journal of Pharmaceutical Sciences. 2015
2. Weichert R, editor. Determination of Extinction Efficiency and Particle Size Distribution by Photosedimentation using Light of Different Wavelengths Particle Size Analysis 1981 Proc 4 th Conf held at Loughborough Univ of Technology, 21-24 Sep. 1981 Edited by N G Stanley-Wood and T Allen Chichester, Wiley, 1982; 1981.
4. Xiang S D, Scholzen A, Minigo G, David C, Aspostolopoulos v, Mottram P L, Plebanski Pathogen Recognition and Development of Particulate Vaccines: Does Size Matter? Methods. 2006: 1-9.
5. Kalkanidis M, Pietersiz G A, Ziang S D, Mottram P L, Crimeen-Irwin B, Ardipradja K, Plebanski M. Methods for Nano-Particle Based Vaccine Formulation and Evaluation of their Immunogenicity. Methods. 2006: 20-29
6. Fung H W M, Mikasa T J T, Vergara J, Sivananthan S J, Guderian J A, Duthie M S, Vedvick T S, Fox C B. Optimizing Manufacturing and Composition of a TLR4 Nanosuspension. Physicochemical Stability and Vaccine Adjuvant Activity. Journal of Nanobiotechnology. 2013: 11-43
7. Weichert R, editor. Determination of Extinction Efficiency and Particle Size Distribution by Photosedimentation using Light of Different Wavelengths. Particle Size Analysis 1981 Proc 4 th Conf held at Loughborough Univ of Technology, 21-24 Sep. 1981 Edited by N G Stanley-Wood and T Allen Chichester, Wiley, 1982; 1981.
8. Schwendener R A. Liposomes as vaccine delivery systems: a review of the recent advances Ther Adv Vaccines. 2014 November; 2(6): 159-182.
9. A. L. Nail, J. L. White, S. L. Hem, Structure of aluminum hydroxide 1: initial precipitate. J Pharm Sci, 65 (1976), pp. 1188-1191.
10. E. B. Lindblad. Aluminium adjuvants D. E S. Stewart-Tull (Ed.), The theory and practical application of adjuvants, John Wiley & Sons, Ltd, New York (1995), pp. 21-35.
11. S. J. Seeber, J. L. White, S. L. Hem. Predicting the adsorption of proteins by aluminum-containing adjuvants Vaccine, 9 (1991), pp. 201-203.
12. S. Iyer, R. S. Robin Robinett, H. HogenEsch, S. L. Hem Mechanism of adsorption of hepatitis B surface antigen by aluminum hydroxide adjuvant Vaccine, 22 (2004), pp. 1475-1479.
13. J. V. Rinella Jr., R. F. Workman, M. A. Hermondson, J. L. White, S. L. Hem. Elutability of proteins from aluminum-containing vaccine adjuvants by treatment with surfactants J Colloid Interface Sci, 197 (1998), pp. 48-56.
14. Baldwin, et. al., 2009, Bertholet, et. al., A Defined Tuberculosis Vaccine Candidate Boosts BCG and Protects Against Multidrug-Resistant *Mycobacterium tuberculosis* 2010 Sci Transl Med 2, 53ra74 (2010)); Baldwin, et. al. The Importance of Adjuvant Formulation in the Development of a Tuberculosis Vaccine. The Journal of Immunology, 2012, 188: 000-000.

The invention claimed is:

1. A nanoalum particle comprising:
an aluminum salt; and
a sizing agent comprises a PEG linked to a lipid;
wherein a size of the nanoalum particle ranges from about 1 nm to about 450 nm, wherein the size of the particles is the Z-average as determined by dynamic light scattering, and wherein a weight ratio of the aluminum salt to the sizing agent is about 1:1-1:3, wherein the nanoalum particle is in a liquid formulation which is filter-sterilized.

2. The nanoalum particle of claim 1, wherein the aluminum salt is selected from the group consisting of aluminum hydroxide, $AlPO_4$, $AlO(OH)$, $Al(OH)(PO_4)$, and $KAl(SO_4)_2$.

3. The nanoalum particle of claim 1, wherein the sizing agent is PEG linked to a phospholipid.

4. The nanoalum particle of claim 3, wherein the phospholipid is selected from the group consisting of DSPE, DPPE, DMPE, and DLPE.

5. The nanoalum particle of claim 1, wherein an average molecular weight of the PEG ranges from about 750 Daltons to about 5000 Daltons.

6. The nanoalum particle of claim 5, herein the average molecular weight of the PEG is about 2000 Daltons or about 5000 Daltons and the lipid is selected from the group comprising DSPE and DPPE.

7. The nanoalum particle of claim 1, wherein the nanoalum particle is stable:
in a liquid formulation at about 0° C. to about 8° C. for about 1 month;
after repeated freeze-thaw cycles; or
in a liquid formulation at about 37° C. for about 1 month.

8. The nanoalum particle of claim 1, wherein an average molecular weight of the PEG is about 2000 Daltons, the lipid is DSPE, and the nanoalum particle is stable in a liquid formulation at about 60° C. for about two weeks.

9. The nanoalum particle of claim 1, wherein the size of the nanoalum particle ranges from about 300 nm to about 400 nm, an average molecular weight of the PEG is about 5000 Daltons, and the weight ratio of the aluminum salt to the sizing agent is about 1:1.

10. The nanoalum particle of claim 1, wherein the size of the nanoalum particle is about 100 nm, an average molecular weight of the PEG is about 5000 Daltons, and the weight ratio of the aluminum salt to the sizing agent is about 1:1.5.

11. The nanoalum particle of claim 1, wherein the size of the nanoalum particle ranges from about 70 nm to about 80 nm, an average molecular weight of the PEG is about 5000 Daltons, and the weight ratio of the aluminum salt to the sizing agent is about 1:2.

12. A method of making the nanoalum particle of claim 1 comprising:
subjecting the aluminum salt to a high energy source in the presence of the sizing agent; or
subjecting the aluminum salt to a high energy source to produce the nanoalum particle with the size ranging from about 1 nm to about 450 nm and mixing the sizing agent with the nanoalum particle within about 30 minutes after subjecting the aluminum salt to the high energy source.

13. The method of claim 12, wherein the high energy source is at least one of a microfluidizer, an extruder, a sonicator, a high shear mixer, or a homogenizer.

14. The method of claim 12, wherein subjecting the aluminum salt to the high energy source comprises 1 to 10 passes through the high energy source.

15. The method of claim 12, wherein the high energy source is a microfluidizer and the mixture comprising the aluminum salt alone or in the presence of the sizing agent is passed through the microfluidizer about 10 passes.

16. A composition comprising the nanoalum particle of claim 1 and a bioactive agent.

17. The composition of claim 16, wherein more than about 75% of the bioactive agent is associated with the nanoalum particle in the composition as determined by gel electrophoresis.

18. The composition of claim 16, wherein the bioactive agent is a polypeptide, a fusion protein, a full-length protein, a peptide, a peptide mimetic, a polynucleotide, an antigen, a Rig-I agonist, ID97, an adjuvant, a diagnostic agent, a therapeutic agent, or an organism.

19. The composition of claim 16, wherein the composition further comprises an adjuvant selected from the group consisting of a AS-2, monophosphoryl lipid A, 3-de-O-acylated monophosphoryl lipid A, IFA, QS21, CWS, TOM, AGPs, CpG-containing oligonucleotides, Toll-like receptor (TLR) agonists, Leif, saponins, saponin mimetics, biological and synthetic lipid A, imiquimod, gardiquimod, resiquimod, polyI:C, flagellin, GLA, SLA, STING, and combinations thereof.

20. A method of stimulating an immune response in a subject comprising administering the composition of claim 16, to a subject, thereby stimulating an immune response in the subject.

21. The method of claim 20, wherein the immune response is primarily a TH1 immune response, primarily a TH2 immune response, or both a TH1 and a TH2 immune response or the immune response involves activation of B-cells, activation of T cells, production of antibodies, or release of cytokines.

22. A method of delivering a bioactive agent to a cell in a subject comprising administering to the subject a composition comprising (a) the nanoalum particle of claim 1 and (b) a bioactive agent, thereby delivering the bioactive agent to the cell in the subject.

23. A nanoalum particle comprising:
an aluminum salt; and
a sizing agent comprises a PEG linked to a lipid, wherein an average molecular weight of the PEG ranges from about 750 Daltons to about 5000 Daltons;
wherein a size of the nanoalum particle ranges from about 1 nm to about 450 nm, wherein the size of the particles is the Z-average as determined by dynamic light scattering, and wherein a weight ratio of the aluminum salt to the sizing agent is about 1:1-1:3.

* * * * *